(12) United States Patent
Ichimori et al.

(10) Patent No.: US 6,495,604 B1
(45) Date of Patent: Dec. 17, 2002

(54) CYCLOALKENE DERIVATIVES, PROCESS FOR PRODUCING THE SAME, AND USE

(75) Inventors: Yuzo Ichimori, Sakai (JP); Masayuki Ii, Minoo (JP); Katsumi Itoh, Osaka (JP); Tomoyuki Kitazaki, Kobe (JP); Junji Yamada, Hikari (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/622,392

(22) PCT Filed: Mar. 8, 1999

(86) PCT No.: PCT/JP99/01103

§ 371 (c)(1),
(2), (4) Date: Aug. 14, 2000

(87) PCT Pub. No.: WO99/46242

PCT Pub. Date: Sep. 16, 1999

(30) Foreign Application Priority Data

Mar. 9, 1998 (JP) .......................... 10-056492
Oct. 6, 1998 (JP) .......................... 10-284362

(51) Int. Cl.$^7$ ..................... A61K 31/18; A61K 31/41; A61K 31/425; A61K 31/215; A61K 31/275
(52) U.S. Cl. ................. 514/602; 514/359; 514/383; 514/520; 514/521; 514/522; 514/529; 514/530; 514/538; 514/562; 514/601; 514/602; 514/603; 514/604; 514/373; 548/166; 548/250; 548/252; 548/253; 548/255; 548/269.4; 558/418; 560/12; 560/13; 562/430; 564/91; 564/92
(58) Field of Search .................. 560/12, 13; 514/530, 514/538, 359, 373, 383, 520, 521, 522, 529, 562, 601, 602, 603, 604; 548/166, 250, 252, 253, 255, 269.4; 558/418; 562/430; 564/91, 92

(56) References Cited

U.S. PATENT DOCUMENTS

| 5,576,016 A | 11/1996 | Amselem et al. ........... 424/450 |
| 5,635,491 A | 6/1997 | Seki et al. .................. 514/53 |
| 5,814,324 A | 9/1998 | Sato et al. .................. 424/405 |

FOREIGN PATENT DOCUMENTS

| WO | WO99/46242 | 9/1999 |
| WO | WO01/56562 | 8/2001 |

OTHER PUBLICATIONS

Graafland et al. (1981) "Steric Effects in the Intramolecular Carboxyl–Catalyzed Hydrolysis of Sulfonamides." J. Am. Chem. Soc. 103:4490–4494.

Illgen et al. (1996) "3–Hydroperoxy–4,5,6,7– tetrahydro–toluene–2,a–sultims: Preparation and Reactions" Molecules 1:139–141.

B. Schulze et al., "Synthesis of Stable Hydroperoxides of Sultams by Oxidation of Isothiazolium Salts", Tetrahedron, vol. 52, No. 3, pp. 783–790 (1996).

T. Graafland et al., "Structure and Reactivity in Intramolecular Catalysis. Catalysis of Sulfonamide Hydrolysis by the Neighboring Carboxyl Group", Journal of the American Chemical Society, vol. 101, No. 23, pp. 6981–6991 (1979).

Primary Examiner—Peter O'Sullivan
(74) Attorney, Agent, or Firm—Mark Chao; Elaine M. Ramesh

(57) ABSTRACT

The present invention provides a compound represented by the formula:

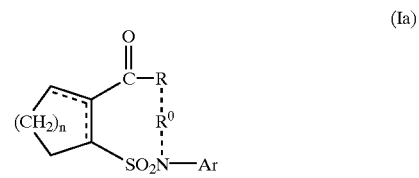

(Ia)

wherein R represents an aliphatic hydrocarbon group optionally having substituents, an aromatic hydrocarbon group optionally having substituents, a heterocyclic group optionally having substituents, a group represented by the formula: OR$^1$ (wherein R$^1$ represents a hydrogen atom or an aliphatic hydrocarbon group optionally having substituents) or a group represented by the formula:

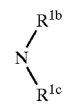

wherein R$^{1b}$ represents a hydrogen atom or an aliphatic hydrocarbon group optionally having substituents, R$^{1c}$ is, same with or different from R$^{1b}$, a hydrogen atom or an aliphatic hydrocarbon group optionally having substituents, R$^0$ represents a hydrogen atom or an aliphatic hydrocarbon group, or R and R$^0$ represents a bond with each other, Ar represents an aromatic hydrocarbon group optionally having substituents,

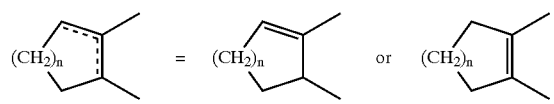

and n is an integer of 1 to 4, or a salt thereof, which is a agent for preventing or treating diseases such as cardiac disease, autoimmune disease, septick shock, etc.

34 Claims, No Drawings

# CYCLOALKENE DERIVATIVES, PROCESS FOR PRODUCING THE SAME, AND USE

This application is the National Stage of International Application No. PCT/JP99/01103, filed Mar. 8, 1999.

TECHNICAL FIELD

The present invention relates to a novel cycloalkene derivative which has an inducible nitric oxide (NO) synthetase-derived nitric oxide production-inhibiting effect and/or an inhibitory effect on the production of inflammatory cytokines such as TNF-α, IL-1, IL-6 and the like, and which is useful as a prophylactic and therapeutic agent against diseases including cardiac diseases, autoimmune diseases, inflammatory diseases, central nervous system diseases, infectious diseases, sepsis, septic shock and the like, a method for producing the same and a use of the same.

BACKGROUND

Nitric oxide (NO) is known to have various important in vivo activities in mammals such as a vasodilating factor in the vascular system [Pharmacol. Rev. Vol. 43, p. 109–142 (1991)], a tumoricidal and bactericidal effect in the immune system [Curr. Opin. Immunol., Vol. 3, p. 65–70 (1991)], and a neurotransmitter in the nervous system [Neuron, Vol. 8, p. 3–11 (1992)]. NO is produced principally from L-arginine by NO synthetase (NOS) and currently is known to exist as three inducible isoforms, namely, neuronal NOS, endothelial NOS and an inducible NOS (iNOS) [Cell, Vol. 70, p. 705–707 (1992)], and the former two are referred to also as constitutive NOS (cNOS) in view of their mode of existence, which is in contrast with the latter iNOS.

cNOS occurs in the vascular endothelial cells and neurons, and is calcium calmodulin dependent and activated by various receptor stimulations to produce a small amount of NO, whereby being considered to contribute to the physiological regulatory effects described above. On the other hand, iNOS is induced in macrophages and a neutrophile by various cytokines and bacterial lipopolysaccharides (LPS) to produce a large amount of NO continuously, which makes it to be believed to have not only the pharmacological effects described above but also cell- and tissue-damaging effects at the site of the production [Immunol. Today, Vol.13, p.157–160 (1992)]. Cells known to express iNOS other than those described above may, for example, be hepatocytes, Kupffer cells, glia cells, vascular smooth muscle cells, vascular endothelial cells, myoendocardium, myocardial cells, mesangial cells, chondrocytes, synovial cells, pancreatic β cells, osteoclasts and the like [FASEB J., Vol.6, p.3051–3064 (1992), Arch. Surg., Vol.128, p.396–401 (1993), J. Biol. Chem., Vol.44, p.27580–27588 (1994), J. Cell. Biochem., Vol.57, p.399–408(1995)], and NO produced in these cells and tissues is known to be involved in various diseases and pathologies. Accordingly, a substance which inhibits the NO production by iNOS inducible cells is considered to be effective as a prophylactic and therapeutic agent against various diseases such as arteriosclerosis, myocarditis, cardiomyopathy, cerebral ischemic failure, Alzheimer's disease, multiple sclerosis, septic shock, chronic rheumatoid arthritis, osteoarthritis, gastric ulcer, duodenal ulcer, ulcerative colitis, diabetes, glomerular nephritis, osteoporosis, pneumonia, hepatitis, psoriasis, graft rejection and pain. From this point of view, several iNOS-inhibiting compounds such as L-arginine analogue [Pharmacol. Rev. Vol.43, p.109–142 (1991)], aminoguanidine [Br. J. Pharmacol., Vol.110, p.963–968 (1993)] and S-ethylisothiourea [J.Biol.Chem., Vol.43, 26669–26676 (1994)] have been reported so far. However, each of these compounds is not satisfactory in terms of it's activity, and has a problematically undesirable inhibitory effect not only on iNOS but also on cNOS which is physiologically active.

On the other hand, cytokines such as TNF-α, IL-1 and IL-6 are secreted from various cells such as monocyte, macrophage, lymphocyte, neutrophile, fibroblast and vascular endothelial cells, and involved widely in inflammation-related biological defense and immune mechanisms [The Cytokine Handbook, 2nd ed., Academic Press Limited (1994), Advances Immunol., Vol.62, p.257–304 (1996)], and thus are referred to as inflammatory cytokines. Since the cells targeted by these cytokines range widely over the inflammatory system, vascular system, central nervous system, hematopoietic system and endocrine system, their biological activities are considered to be diverse, including representative biological activities of TNF-α and IL-1 which were reported to be (1) a pyrogenic activity, (2) an activation and chemotaxis promotion of inflammatory cells such as macrophage and neutrophile, (3) an induction of inflammatory cytokines and acute phase proteins including IL-1, IL-6, IL-8, TNF-α and CSF and (4) an enhancement of the production of various chemical mediators such as NO, $O_2^-$, PAF, prostaglandin, leukotriene and protease as well as those of IL-6 which were reported to be (1) an induction of acute phase proteins, (2) a thrombocyte-increasing activity, (3) a differentiation and an activation of lymphocytes and NK cells and (4) a osteoclast-increasing activity. However, these cytokines, once produced excessively or produced in a wrong site or at a wrong time, exhibit undesirable biological effects, and are proven to be involved in various diseases such as cachexia due to protozoa, bacteria, fungi, viruses and cancers, allergic diseases, chronic rheumatoid arthritis, abscess, graft rejection, anemia, arteriosclerosis, autoimmune disease, diabetes, central nervous system diseases, inflammatory bowel diseases, cardiac failure, hepatitis, hepatocirrhosis, nephritis, osteoporosis, psoriasis, septic shock and the like. From this point of view, substances which have inhibitory effects or antagonistic effects on the production of TNF-α, IL-1 and IL-6 and the like [Eur. J. Immunol., Vol.18, p.951–956 (1991), Immunol., Vol.83, p.262–267 (1994), Proc. Natl. Acad. Sci., Vol.93, p.3967–3971 (1997), J. Immunol., Vol.147, p.1530–1536 (1991), Immunol. Today, Vol.12, p.404–410 (1991)] were reported to be expected to serve as the therapeutic agents against diseases listed above.

DISCLOSURE OF INVENTION

While several therapeutic agents for treating cardiac failure, autoimmune diseases, inflammatory diseases and septic shock have been known, each of them was not excellent in pharmaceutical properties such as efficacy and safety, and thus an objective of the invention is to provide a prophylactic and therapeutic agent against cardiac failure, autoimmune diseases, inflammatory diseases and septic shock which is further improved with regard to the pharmaceutical properties mentioned above.

In view of such circumstances, we made an effort to obtain a prophylactic and therapeutic agent against the diseases listed above which has an inhibitory effect on the NO production and/or the inflammatory cytokine production by an iNOS-inducible cell, and finally have succeeded to synthesize a novel compound represented by the formula:

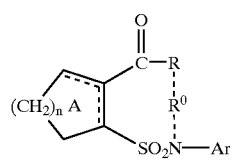
(Iaa)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, ring A is a cycloalkene substituted by 1 to 4 substituents selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, $R^0$ represents a hydrogen atom or an aliphatic hydrocarbon group, or R and $R^0$ represent a bond with each other, Ar represents an aromatic hydrocarbon group optionally having substituents, a group represented by the formula:

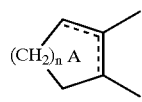

represents a group represented by the formula:

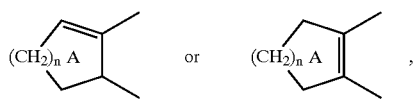

and n is an integer of 1 to 4, or a salt thereof, and a novel compound represented by the formula:

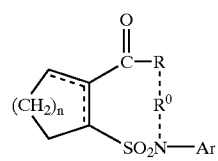
(Ia)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

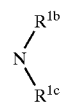

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents), $R^0$ represents a hydrogen atom or an aliphatic hydrocarbon group, or R and $R^0$ represent a bond with each other, Ar represents an aromatic hydrocarbon group optionally having substituents, a group represented by the formula:

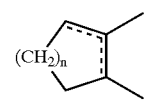

represents a group represented by the formula:

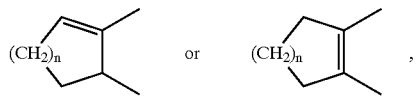

and n is an integer of 1 to 4, provided that when n is 1 or 2, and (i) $R^1$ is a hydrogen atom or an ethyl group, $R^0$ is a methyl group and Ar is a phenyl group, or (ii) R and $R^0$ represent a bond with each other and Ar is a phenyl group, a 2-methylphenyl group, a 4-bromophenyl group, a 4-methoxyphenyl group or a 2,6-dimethylphenyl group, a group represented by the formula:

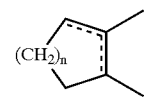

is a group represented by the formula:

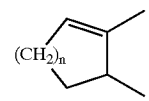

or a salt thereof, which is characterized by a cycloalkene structure having a carboxylate group or a carbonyl group and a sulfonamide group (preferred examples among them include a novel compound represented by the formula:

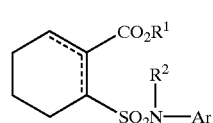
(Id)

wherein $R^2$ represents a hydrogen atom or an aliphatic hydrocarbon group, $R^1$, Ar represent the same meanings as defined above, a group represented by the formula:

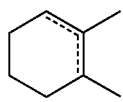

represents a group represented by the formula:

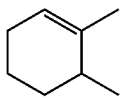 or 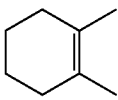

provided that when Ar is a phenyl group, $R^1$ is an ethyl group and $R^2$ is a methyl group, the group represented by the formula:

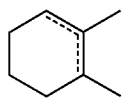

is a group represented by the formula:

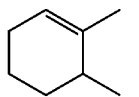, etc.).

Furthermore, the inventors have found that a compound represented by the formula:

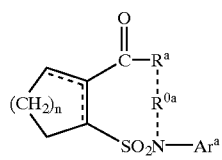 (Ie)

wherein $R^a$ represents an aliphatic hydrocarbon group optionally having substituents, an aromatic hydrocarbon group optionally having substituents, a heterocyclic group optionally having substituents, a group represented by the formula: $OR^{1a}$ (wherein $R^{1a}$ represents a hydrogen atom or an aliphatic hydrocarbon group optionally having substituents) or a group represented by the formula:

wherein $R^{1a}$ represents the same meaning as defined above, $R^{1b}$ is, same with or different from $R^{1a}$, a hydrogen atom or an aliphatic hydrocarbon group optionally having substituents, $R^{0a}$ represents a hydrogen atom or an aliphatic hydrocarbon group, or $R^a$ and $R^{0a}$ represent a bond with each other, $Ar^a$ represents an aromatic hydrocarbon group optionally having substituents, a group represented by the formula:

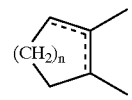

represents a group represented by the formula:

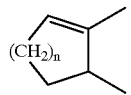 or 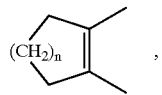, n represents an integer of 1 to 4, or a salt thereof which contains (i) the novel compound represented by the formula (Iaa) or a salt thereof, and (ii) the novel compound represented by the formula (Ia) (preferred examples among them include a compound represented by the formula:

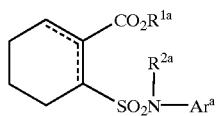 (Ig)

wherein $R^{2a}$ represents a hydrogen atom or an aliphatic hydrocarbon group, $R^{1a}$ and $Ar^a$ represent the same meanings as defined above, the group represented by the formula:

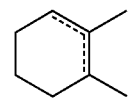

represents a group represented by the formula:

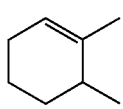 or 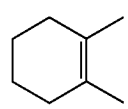

which includes the novel compound (Id) or a salt thereof, etc.) unexpectedly has an excellent NO and/or cytokine production-inhibiting effect and has excellent pharmaceutical properties essential for a prophylactic and therapeutic agent against cardiac failure, autoimmune diseases, inflammatory diseases and septic shock.

It is understood that, in the diseases described above, the inflammatory cytokines such as TNF-α, IL-1 and IL-6 and NO are involved as being complicated with each other rather than as being independent of each other whereby further exacerbating the diseases, and thus a compound having excellent effects, such as an inihibitory effect not only on the NO production but also on the inflammatory cytokine production by an iNOS-inducible cell, can be a more effective prophylactic and therapeutic agent than any conventional agent, resulting in a clinical usefulness.

That is, the present invention relates to:
(1) A compound represented by the formula:

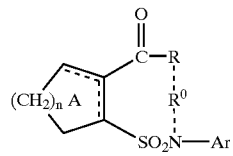
(Iaa)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents), $R^0$ represents a hydrogen atom or an aliphatic hydrocarbon group, or R and $R^0$ represent a bond with each other, ring A is a cycloalkene substituted by 1 to 4 substituents selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

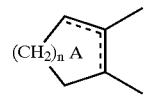

represents a group represented by the formula:

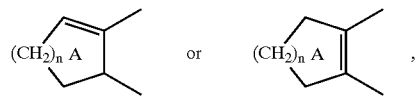

and n is an integer of 1 to 4, or a salt thereof,
(2) A compound represented by the formula:

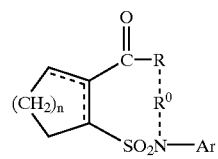
(Ia)

wherein R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, or R and $R^0$ represents a bond with each other, Ar represents an aromatic hydrocarbon group optionally having substituents, a group represented by the formula:

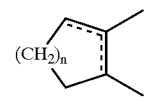

represents a group represented by the formula:

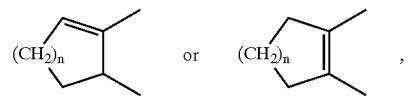

and n is an integer of 1 to 4, provided that when n is 1 or 2 and (i) $R^1$ is a hydrogen atom or an ethyl group, $R^0$ is a methyl group and Ar is a phenyl group or (ii) R and $R^0$ represent a bond with each other and Ar is a phenyl group, a 2-methylphenyl group, a 4-bromophenyl group, a 4-methoxyphenyl group or a 2,6-dimethylphenyl group, a group represented by the formula:

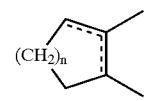

is a group represented by the formula:

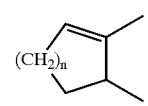

or a salt thereof,
(3) A compound as defined in (2), wherein the compound represented by the formula (Ia) is a compound represented by the formula:

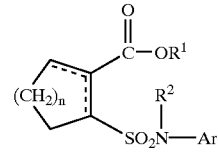
(Ib)

wherein $R^2$ represents a hydrogen atom or an aliphatic hydrocarbon group, $R^1$, Ar, n and the group represented by the formula:

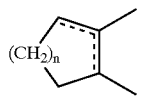

represent the same meanings as defined in (2), provided that when n is 1 or 2, Ar is a phenyl group, $R^1$ is a hydrogen atom or an ethyl group and $R^2$ is a methyl group, the group represented by the formula:

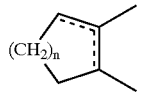

is a group represented by the formula:

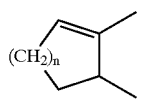

(4) A compound as defined in (2), wherein the compound represented by the formula (Ia) is a compound represented by the formula:

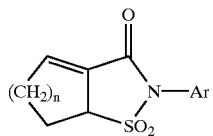

(Ic)

wherein Ar and n represent the same meanings as defined in (2), (5) A compound as defined in (1), wherein the compound represented by the formula (Iaa) is a compound represented by the formula:

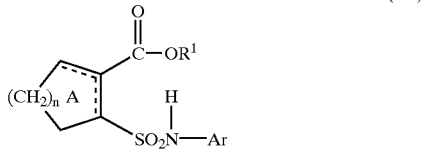

(Ibb)

wherein each symbol represents the same meaning as defined in (1), (6) A compound as defined in (5), wherein the ring A is a cycloalkene substituted by lower alkyl, phenyl or halogen, $R^1$ is a lower alkyl group, Ar is a phenyl group optionally having substituents, and n is 2, (7) A compound as defined in (3), wherein $R^1$ is a lower alkyl group optionally having substituents, (8) A compound as defined in (3), wherein $R^1$ is an ethyl group, (9) A compound as defined in (3), wherein $R^2$ is a hydrogen atom or a lower alkyl group,

(10) A compound as defined in (3), wherein $R^2$ is a hydrogen atom,

(11) A compound as defined in (3), wherein Ar is a phenyl group optionally having substituents,

(12) A compound as defined in (3), wherein Ar is a phenyl group substituted by halogen or/and lower alkyl,

(13) A compound as defined in (3), wherein Ar is a group represented by the formula:

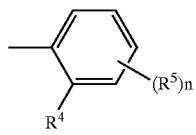

wherein $R^4$ and $R^5$ are same or different and represents a halogen atom or a lower alkyl group, and n is an integer of 0 to 2,

(14) A compound as defined in (3), wherein the halogen atom is a fluoro atom or a chloro atom,

(15) A compound as defined in (3), wherein the group represented by the formula:

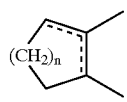

is a group represented by the formula:

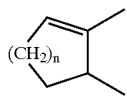

wherein n is the same meaning as defined in (2),

(16) A compound as defined in (3), wherein n is 1 to 3,

(17) A compound as defined in (3), wherein $R^1$ is a lower alkyl group optionally having substituents, $R^2$ is a hydrogen atom or a lower alkyl group, Ar is a phenyl group optionally having substituents, n is 1, 2 or 3,

(18) A compound as defined in (3), wherein $R^1$ is a lower alkyl group optionally having substituents, $R^2$ is a hydrogen atom, Ar is a phenyl group substituted by a halogen atom, n is 2,

(19) A compound as defined in (4), wherein Ar is a phenyl group optionally having substituents, n is 2,

(20) A compound as defined in (2), wherein the compound represented by the formula (Ia) is a compound represented by the formula:

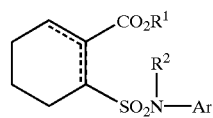

(Id)

wherein $R^1$, $R^2$ and Ar represent the same meanings as defined in (3), a group represented by the formula:

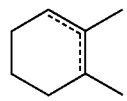

represents a group represented by the formula:

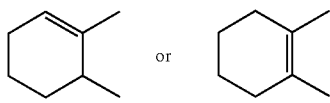

provided that when Ar is a phenyl group, R¹ is a hydrogen atom or an ethyl group and R² is a methyl group, the group represented by the formula:

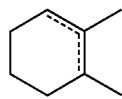

is a group represented by the formula:

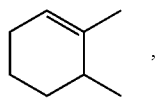,

(21) A compound as defined in (2) which is d-ethyl 6-[N-(2,4-difluorophenyl)sulfamoyl]-1-cyclohexene-1-carboxylate or a salt thereof,
(22) A compound as defined in (2) which is ethyl 6-[N-(2,4-chlorophenyl)sulfamoyl]-1-cyclohexene-1-carboxylate or a salt thereof,
(23) A compound as defined in (2) which is ethyl 6-[N-(2-chloro-4-methylphenyl)sulfamoyl]-1-cyclohexene-1-carboxylate or a salt thereof,
(24) A compound as defined in (2) which is d-ethyl 6-[N-(2-chloro-4-fluorophenyl)sulfamoyl]-1-cyclohexene-1-carboxylate or a salt thereof,
(25) A method for producing a compound as defined in (3) which comprises reacting a compound represented by the formula:

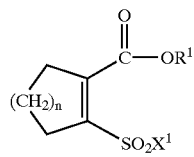 (IIa)

wherein $R^1$ and n represent the same meanings as defined in (3) and $X^1$ represents a leaving group, or a salt thereof with a compound represented by the formula:

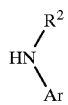 (IIIa)

wherein each symbol represents the same meaning as defined in (3), or a salt thereof,
(26) A method for producing a compound as defined in (4) which comprises subjecting a compound represented by the formula:

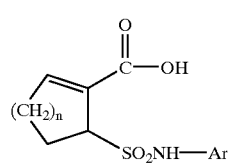 (IIb)

wherein each symbol represents the same meaning as defined in (4), or a salt thereof to a ring-closing reaction,

(27) A method for producing a compound as defined in (20) which comprises reacting a compound represented by the formula:

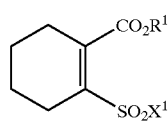 (IIc)

wherein $R^1$ represents the same meanings as defined in (20) and $X^1$ represents a leaving group, or a salt thereof with a compound represented by the formula:

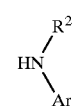 (IIIa)

wherein each symbol represents the same meaning as defined in (20), or a salt thereof,
(28) A pharmaceutical composition which contains a compound represented by the formula:

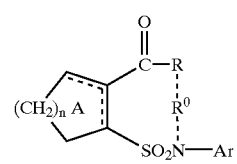 (Iaa)

wherein R represents an aliphatic hydrocarbon group optionally having substituents, an aromatic hydrocarbon group optionally having substituents, a heterocyclic group optionally having substituents, a group represented by the formula: $OR^1$ wherein $R^1$ represents a hydrogen atom or an aliphatic hydrocarbon group optionally having substituents or a group represented by the formula:

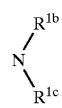

(wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents), $R^0$ represents a hydrogen atom or an aliphatic hydrocarbon group, or R and $R^0$ represents a bond with each other, ring A is a cycloalkene substituted by 1 to 4 substituents selected from (i) an aliphatic hydrocarbon group optionally having substituents, (ii) an aromatic hydrocarbon group optionally having substituents, (iii) a group represented by the formula: $OR^1$ (wherein $R^1$ represents the same meaning as mentioned above) and (iv) a halogen atom, Ar represents an aromatic hydrocarbon group optionally having substituents, a group represented by the formula:

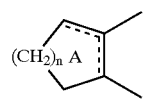

represents a group represented by the formula:

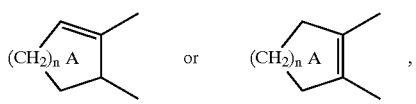

and n is an integer of 1 to 4, or a salt thereof,

(29) A pharmaceutical composition which contains a compound represented by the formula:

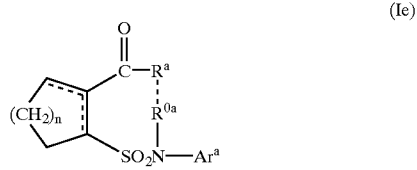

(Ie)

wherein $R^a$ represents an aliphatic hydrocarbon group optionally having substituents, an aromatic hydrocarbon group optionally having substituents, a heterocyclic group optionally having substituents, a group represented by the formula: $OR^{1a}$ (wherein $R^{1a}$ represents a hydrogen atom or an aliphatic hydrocarbon group optionally having substituents) or a group represented by the formula:

(wherein $R^{1a}$ represents the same meaning as defined above, $R^{1b}$ is, same with or different from $R^{1a}$, a hydrogen atom or an aliphatic hydrocarbon group optionally having substituents, $R^{0a}$ represents a hydrogen atom or an aliphatic hydrocarbon group, or $R^a$ and $R^{0a}$ represent a bond with each other, $Ar^a$ represents an aromatic hydrocarbon group optionally having substituents, a group represented by the formula:

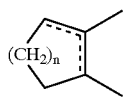

represents a group represented by the formula:

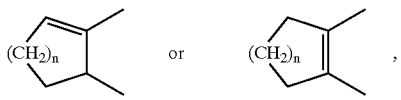

n represents an integer of 1 to 4, or a salt thereof,

(30) A pharmaceutical composition which contains a compound represented by the formula:

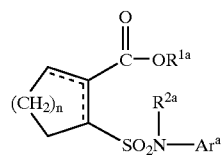

(If)

wherein $R^{2a}$ represents a hydrogen atom or an aliphatic hydrocarbon group, $R^{1a}$, $Ar^a$, n and the group represented by the formula:

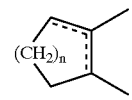

represent the same meanings as defined in (29), or a salt thereof,

(31) A pharmaceutical composition which contains a compound represented by the formula:

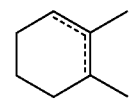

(Ig)

wherein $R^{1a}$, $R^{2a}$ and $Ar^a$ represent the same meaning as defined in (30) and the group represented by the formula:

is a group represented by the formula:

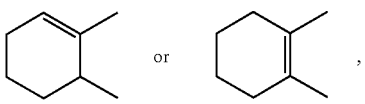

(32) The pharmaceutical composition as defined in any one of (28) to (31) which is an agent for inhibiting nitric oxide and/or cytokine production,

(33) The pharmaceutical composition as defined in (32) which is an agent for preventing or treating cardiac disease, autoimmune disease or septic shock,

(34) Use of the compound represented by the formula (Iaa) or (Ie) for manufacturing an agent for inhibiting nitric oxide and/or cytokine production,

(35) A method for inhibiting nitric oxide and/or cytokine production in mammals which comprises administrating to a subject in need an effective amount of the compound represented by the formula (Iaa) or (Ie),

(36) Use of the compound represented by the formula (Iaa) or (Ie) for manufacturing an agent for preventing or treating cardiac disease, autoimmune disease or septic shock,

(37) A method for preventing or treating cardiac disease, autoimmune disease or septic shock in mammals which comprises administrating to a subject in need an effective amount of the compound represented by the formula (Iaa) or (Ie),

(38) A pro-drug of the compound as defined in (1) or (2),

(39) A pharmaceutical composition which contains the pro-drug as defined in (38), and so on.

In the specification, R represents an aliphatic hydrocarbon group optionally having substituents, an aromatic hydrocarbon group optionally having substituents, a heterocyclic group optionally having substituents, a group represented by the formula: $OR^1$ (wherein $R^1$ represents a hydrogen atom or an aliphatic hydrocarbon group optionally having substituents) or a group represented by the formula:

wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, or R forms a bond with $R^0$, and among them the group represented by the formula: $OR^1$ (wherein $R^1$ represents the same meaning as defined above) is preferred.

And, $R^a$ represents an aliphatic hydrocarbon group optionally having substituents, an aromatic hydrocarbon group optionally having substituents, a heterocyclic group optionally having substituents, a group represented by the formula: $OR^{1a}$ (wherein $R^{1a}$ represents a hydrogen atom or an aliphatic hydrocarbon group optionally having substituents) or a group represented by the formula:

(wherein $R^{1a}$ represents the same meaning as defined above, $R^{1b}$ is, same with or different from $R^{1a}$, a hydrogen atom or an aliphatic hydrocarbon group optionally having substituents), or form a bond with $R^{0a}$, and among them the group represented by the formula: $OR^1$ (wherein $R^1$ represents the same meaning as defined above) is preferred.

When R and $R^0$ represent a bond with each other, the compound represented by the formula (Iaa) can be represented by the formula:

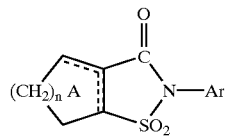

(Ihh)

wherein each symbol represents the same meanings, and specifically can be represented by the formula:

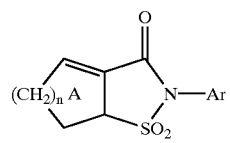

(Icc)

wherein each symbol represents the same meanings, or the formula:

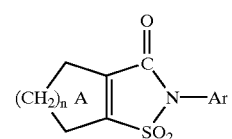

(Iii)

wherein each symbols represents the same meanings.

When R and $R^0$ represent a bond with each other, the compound represented by the formula (Ia) can be represented by the formula:

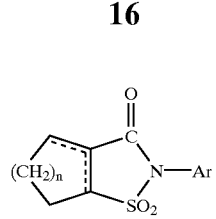

(Ih)

wherein each symbols represents the same meanings, and specifically can be represented by the formula:

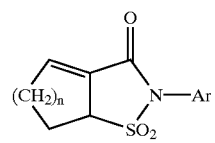

(Ic)

wherein each symbols represents the same meanings, or the formula:

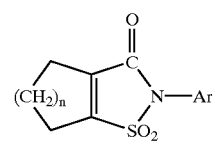

(Ii)

wherein each symbols represents the same meanings.

When $R^a$ and $R^{0a}$ represent a bond with each other, the compound represented by the formula (Ie) can be represented by the formula:

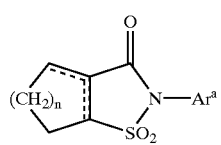

(Ij)

wherein each symbols represents the same meanings, and specifically can be represented by the formula:

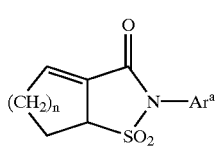

(Ik)

wherein each symbols represents the same meanings, or the formula:

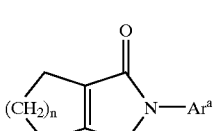

(Im)

wherein each symbols represents the same meanings.

When R is a group represented by the formula: $OR^1$ (wherein $R^1$ represents the same meaning as defined above), the compound represented by the formula (Iaa) can be represented by the formula:

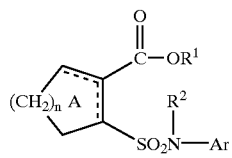
(Ibb)

wherein each symbols represents the same meanings, and specifically can be represented by the formula:

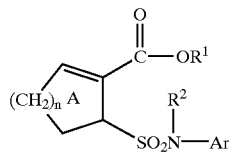
(Inn)

wherein each symbols represents the same meanings, or the formula:

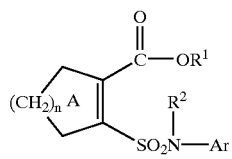
(Ioo)

wherein each symbols represents the same meanings.

When R is a group represented by the formula: $OR^1$ (wherein $R^1$ represents the same meaning as defined above), the compound represented by the formula (Ia) can be represented by the formula:

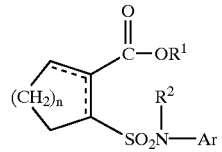
(Ib)

wherein each symbols represents the same meanings, and specifically can be represented by the formula:

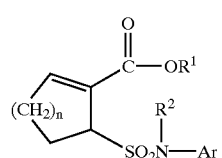
(In)

wherein each symbols represents the same meanings, or the formula:

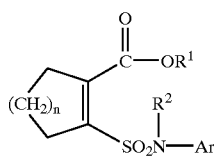
(Io)

wherein each symbols represents the same meanings.

When $R^a$ is a group represented by the formula: $OR^{1a}$ (wherein $R^{1a}$ represents the same meaning as defined above), the compound represented by the formula (Ie) can be represented by the formula:

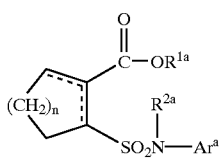
(If)

wherein each symbols represents the same meanings, and specifically can be represented by the formula:

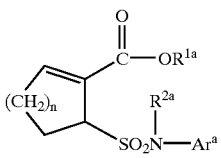
(Ip)

wherein each symbols represents the same meanings, or the formula:

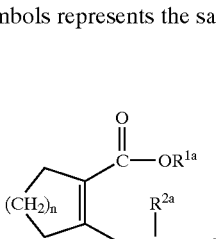
(Iq)

wherein each symbols represents the same meanings.

As the compound represented by the formula (Iaa), the compound represented by the formula (Icc) or the formula (Inn) is preferred, as the compound represented by the formula (Ia), the compound represented by the formula (Ic) or the formula (In) are preferred, and as the compound represented by the formula (Ie), the compound represented by the formula (Ik) or the formula (Ip) are preferred, Similarly, the compound represented by the formula (Id) can be represented by the formula:

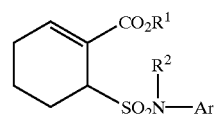
(Ir)

wherein each symbols represents the same meanings, or the formula:

$$\text{(Is)}$$

[cyclohexene structure with CO$_2$R$^1$ and R$^2$-SO$_2$N-Ar substituents]

wherein each symbols represents the same meaning, and the compound represented by the formula (Ig) can be represented by the formula:

$$\text{(It)}$$

[cyclohexene structure with CO$_2$R$^{1a}$ and R$^{2a}$-SO$_2$N-Ar$^a$ substituents]

wherein each symbols represents the same meanings, or the formula:

$$\text{(Iu)}$$

[cyclohexene structure with CO$_2$R$^{1a}$ and R$^{2a}$-SO$_2$N-Ar$^a$ substituents]

wherein each symbols represents the same meanings.

As the compound represented by the formula (Id), the compound represented by the formula (Ir) is preferred, as the compound represented by the formula (Ig), the compound represented by the formula (It) is preferred.

In the compound represented by the formula (Ia), when n is 1 or 2, and (i) $R^1$ is a hydrogen atom or an ethyl group, $R^0$ is a methyl group and Ar is a phenyl group, or (ii) R and $R^0$ represent a bond with each other and Ar is a phenyl group, a 2-methylphenyl group, a 4-bromophenyl group, a 4-methoxyphenyl group or a 2,6-dimethylphenyl group, a group represented by the formula:

[cyclic structure with (CH$_2$)$_n$]

is a group represented by the formula:

[cyclic structure with (CH$_2$)$_n$].

Furthermore, when n is 1 to 4, and (i) $R^1$ is a hydrogen atom or a lower alkyl group optionally having substituents, $R^0$ is a lower alkyl group optionally having substituents, and Ar is a phenyl group optionally having substituents, or (ii) R and $R^0$ represent a bond with each other and Ar is a phenyl group optionally having substituents, a group represented by the formula:

[cyclic structure with (CH$_2$)$_n$]

may be a group represented by the formula:

[cyclic structure with (CH$_2$)$_n$].

In the compound represented by the formula (Ib), when n is 1 or 2, $R^1$ is a hydrogen atom or an ethyl group, $R^0$ is a methyl group, and Ar is a phenyl group, a group represented by the formula:

[cyclic structure with (CH$_2$)$_n$]

is a group represented by the formula:

[cyclic structure with (CH$_2$)$_n$].

Furthermore, when n is 1 to 4, and $R^1$ is a hydrogen atom or a lower alkyl group optionally having substituents, $R^0$ is a lower alkyl group optionally having substituents, and Ar is a phenyl group optionally having substituents, a group represented by the formula:

[cyclic structure with (CH$_2$)$_n$]

is a group represented by the formula:

[cyclic structure with (CH$_2$)$_n$].

As the "aliphatic hydrocarbon group" of the "aliphatic hydrocarbon group optionally having substituents" represented by R, $R^1$, $R^{1a}$, $R^{1b}$, $R^{1c}$, and the "aliphatic hydrocarbon group" represented by $R^0$, $R^{0a}$, $R^2$, $R^{2a}$, for example, an alkyl group, a cycloalkyl group, a cycloalkylalkyl group, an alkenyl group, an alkynyl group, etc. are preferred.

As the alkyl group, for example, a linear or branched alkyl group having 1 to 20 carbons (e.g., a methyl group, an ethyl group, a n-propyl group, an isopropyl group, a n-butyl group, an isobutyl group, a sec-butyl group, a tert-butyl group, a pentyl group, a hexyl group, a heptyl group, an octyl group, an nonyl group, a decyl group, a dodecyl group, etc.), etc. are preferred, and particularly, for example, a lower alkyl group having 1 to 6 carbons (e.g., a methyl group, an ethyl group, a n-propyl group, an isopropyl group, a n-butyl group, an isobutyl group, a sec-butyl group, a tert-butyl group, etc.), etc. are preferred.

As the cycloalkyl group, for example, a cycloalkyl group having 3 to 10 carbons (e.g., a cyclopropyl group, a cyclobutyl group, a cyclopentyl group, a cyclohexyl group, a cycloheptyl group, a cyclooctyl group, etc.), etc. are preferred, and particularly, for example, a cycloalkyl group having 3 to 6 carbons (e.g., a cyclopropyl group, a cyclobutyl group, a cyclopentyl group, a cyclohexyl group, etc.), etc. are preferred.

As the cycloalkylalkyl group, for example, a cycloalkylalkyl group having 4 to 12 carbons (e.g., a cyclopropylmethyl group, a cyclopentylmethyl group, a cyclohexylmethyl group, a cycloheptylmethyl group, etc.), etc. are preferred, and particularly, for example, a cycloalkylalkyl group having 4 to 8 (particularly, 4 to 7) carbons (e.g., a cyclopropylmethyl group, a cyclopentylmethyl group, a cyclohexylmethyl group, etc.), etc. are preferred.

As the alkenyl group, for example, a lower alkenyl group having 3 to 6 carbons (e.g., a propenyl group, a butenyl group, a pentenyl group, etc.), and particularly, for example, a lower alkenyl group having 3 or 4 carbons (e.g., a propenyl group, a butenyl group, etc.), etc. are preferred.

As the alkynyl group, for example, a lower alkynyl group having 3 to 6 carbons (e.g., a propynyl group, a butynyl group, a pentynyl group, etc.), and particularly, for example, a lower alkenyl group having 3 or 4 carbons (e.g., a propynyl group, a butynyl group, etc.), etc. are preferred.

As the "substituents" of the above mentioned "aliphatic hydrocarbon group optionally having substituents", for example, a heterocyclic group, an oxo group, a hydroxy group, a $C_{1-6}$ alkoxy group, a $C_{3-10}$ (particularly, $C_{3-6}$) cycloalkyloxy group, a $C_{6-10}$ aryloxy group, a $C_{7-19}$ (particularly, $C_{7-12}$) aralkyloxy group, a heterocyclic oxy group, a $C_{1-6}$ alkylthio group (the sulfur atom may be oxidized), a $C_{3-10}$ (particularly, $C_{3-6}$) cycloalkylthio group (the sulfur atom may be oxidized), a $C_{6-10}$ arylthio group (the sulfur atom may be oxidized), a $C_{7-19}$ (particularly, $C_{7-12}$) aralkyloxy group (the sulfur atom may be oxidized), a heterocyclic thio group, a heterocyclic sulfinyl group, a heterocyclic sulfonyl group, a nitro group, a halogen atom, a cyano group, a carboxyl group, a $C_{1-10}$ (particularly, $C_{1-6}$) alkoxy-carbonyl group, a $C_{3-6}$ cycloalkyloxy-carbonyl group, a $C_{6-10}$ aryloxy-carbonyl group, a $C_{7-19}$ (particularly, $C_{7-12}$) aralkyloxy-carbonyl group, a heterocyclic oxycarbonyl group, a $C_{6-10}$ aryl-carbonyl group, $C_{1-6}$ alkanoyl group, $C_{3-5}$ alkenoyl group, a $C_{6-10}$ aryl-carbonyloxy group, a $C_{2-6}$ alkanoyloxy group, a $C_{3-5}$ alkenoyloxy group, a carbamoyl group optionally having substituents, a thiocarbamoyl group optionally having substituents, a carbamoyloxy group optionally having substituents, a $C_{1-6}$ alkanoylamino group, a $C_{6-10}$ aryl-carbonylamino group, a $C_{1-10}$ (particularly, $C_{1-6}$) alkoxy-carboxamide group, a $C_{6-10}$ aryloxy-carboxamide group, a $C_{7-19}$ (particularly, $C_{7-12}$) aralkyloxy-carboxamide group, a $C_{1-10}$ (particularly, $C_{1-6}$) alkoxy-carbonyloxy group, a $C_{6-10}$ aryloxy-carbonyloxy group, a $C_{7-19}$ (particularly, $C_{7-12}$) aralkyloxy-carbonyloxy group, a $C_{3-10}$ particularly, $C_{3-6}$)cycloalkyloxy-carbonyloxy group, an ureido group optionally having substituents, a $C_{6-10}$ aryl group optionally having substituents, etc. are used.

These substituents are substituted at substitutable positions in the above mentioned "aliphatic hydrocarbon group", and the substituents are not limited to one and may be same or different and a few numbers (2 to 4).

As the "$C_{1-6}$ alkoxy group", for example, a methoxy group, an ethoxy group, a n-propoxy group, an isopropoxy group, a n-butoxy group, a tert-butoxy group, a n-pentyloxy group, a n-hexyloxy group, etc. are used, as the "$C_{3-10}$ cycloalkyloxy group", for example, a cyclopropyloxy group, a cyclohexyloxy group, etc. are used, as the "$C_{6-10}$ aryloxy group", for example, a phenoxy group, a naphthyloxy group, etc. are used, as the "$C_{7-19}$ aralkyloxy group", for example, a benzyloxy group, a 1-phenylethyloxy group, a 2-phenylethyloxy group, a benzhydryloxy group, a 1-naphthylmethyloxy group, etc. are used, as the "$C_{1-6}$ alkylthio group (the sulfur atom may be oxidized)", for example, a methylthio group, an ethylthio group, a n-propylthio group, a n-butylthio group, a methylsulfinyl group, a methylsulfonyl group, etc. are used, as the "$C_{3-10}$ cycloalkylthio group (the sulfur atom may be oxidized)", for example, a cyclopropylthio group, a cyclohexylthio group, a cyclopentylsulfinyl group, a cyclohexylsulfonyl group, etc. are used, as the "$C_{6-10}$ arylthio group (the sulfur atom may be oxidized)", for example, a phenylthio group, a naphthylthio group, a phenylsulfinyl group, a phenylsulfonyl group, etc. are used, as the "$C_{9-19}$ aralkylthio group (the sulfur atom may be oxidized)", for example, a benzylthio group, a phenylethylthio group, a benzhydrylthio group, a benzylsulfinyl group, a benzylsulfonyl group, etc. are used, as the "halogen atom", for example, a fluorine atom, a chlorine atom, a bromine atom, an iodine atom, etc. are used, as the "$C_{1-10}$ alkoxy-carbonyl group", for example, a methoxycarbonyl group, an ethoxycarbonyl group, a n-propoxycarbonyl group, an isopropoxycarbonyl group, a n-butoxycarbonyl group, a isobutoxycarbonyl group, a tert-butoxycarbonyl group, etc. are used, as the "$C_{3-6}$ cycloalkyloxycarbonyl group", for example, a cyclopropyloxycarbonyl group, a cyclopentyloxycarbonyl group, a cyclohexyloxycarbonyl group, a norbornyloxycarbonyl group, etc. are used, as the "$C_{6-10}$ aryloxy-carbonyl group", for example, a phenoxycarbonyl group, a naphthyloxycarbonyl group, etc. are used, as the "$C_{7-19}$ aralkyl-oxycarbonyl group", for example, a benzyloxycarbonyl group, a benzhydryloxycarbonyl group, a 2-phenethyloxycarbonyl group, etc. are used, as the "$C_{6-10}$ aryl-carbonyl group", for example, a benzoyl group, a naphthoyl group, a phenylacetyl group, etc. are used, as the "$C_{1-6}$ alkanoyl group", for example, a formyl group, an acetyl group, a propionyl group, a butyryl group, a valeryl group, a pivaloyl group, etc. are used, as the "$C_{3-5}$ alkenoyl group", for example, an acryloyl group, a crotonoyl group, etc. are used, as the "$C_{6-10}$ aryl-carbonyloxy group", for example, a benzoyloxy group, a naphthoyloxy group, a phenylacetoxy group, etc. are used, as the "$C_{2-6}$ alkanoyloxy group", for example, an acetoxy group, a propionyloxy group, a butyryloxy group, a valeryloxy group, a pivaloyloxy group, etc. are used, as the "$C_{3-5}$ alkenoyl group", for example, an acryloyloxy group, a crotonoyloxy group, etc. are used.

As the "carbamoyl group optionally having substituents", for example, a carbamoyl group or a cyclicaminocarbonyl group, which may be substituted by 1 or 2 substituents selected from $C_{1-4}$ alkyl (e.g., methyl, ethyl, etc.), phenyl, $C_{1-7}$ acyl (e.g., acetyl, propionyl, benzoyl, etc.), $C_{1-4}$ alkoxyphenyl (e.g., methoxyphenyl, etc.), etc. and specifically for example a carbamoyl group, a N-methylcarbamyl group, a N-ethylcarbamoyl group, a N,N-dimethylcarbamoyl group, a N,N-diethylcarbamoyl group, a N-phenylcarbamoyl group, a N-acetylcarbamoyl group, a N-benzoylcarbamoyl group, a N-(p-methoxyphenyl)carbamoyl group, a 1-pyrrolydinylcarbonyl group, a piperazinocarbonyl group, a 1-piperazinylcarbonyl group, a morpholinocarbamoyl group, etc. are used.

As the "thiocarbamoyl group optionally having substituents", for example, a thiocarbamoyl group which may be substituted by 1 or 2 substituents selected from $C_{1-4}$ alkyl (e.g., methyl, ethyl, etc.), phenyl, etc. and specifically for example a thiocarbamoyl group, a N-methylthiocarbamoyl group, a N-phenylthiocarbamoyl group, etc. are used.

As the "carbamoyloxy group optionally having substituents", for example, a carbamoyloxy group which may be substituted by 1 or 2 substituents selected from $C_{1-4}$ alkyl (e.g., methyl, ethyl, etc.), phenyl, etc. and specifically for example a carbamoyloxy group, a N-methylcarbamoyloxy group, a N,N-dimethylcarbamoyloxy group, a N-ethylcarbamoyloxy group, a N-phenylcarbamoyloxy group, etc. are used.

As the "$C_{1-6}$ alkanoylamino group", for example, an acetoamide group, a propionamide group, a butyroamide group, a valeroamide group, a pivaloamide group, etc. are used, as the "$C_{6-10}$ aryl-carbonylamino group", for example, a benzamide group, a naphthoamide group, a phthalimide group, etc. are used, as the "$C_{1-10}$ alkoxy-carboxamide group", for example, a methoxycarboxamide ($CH_3OCONH-$) group, an ethoxycarboxamide group, a tert-butoxycarboxamide group, etc. are used, as the "$C_{6-10}$ aryloxy-carboxamide group", for example, a phenoxycarboxamide ($C_6H_5OCONH-$) group, etc. are used, as the "$C_{7-10}$ aralkyloxy-carboxamide group", for example, a benzyloxycarboxamide ($C_6H_5CH_2OCONH-$) group, a benzhydryloxycarboxamide group, etc. are used, as the "$C_{1-10}$ alkoxy-carbonyloxy group", for example, a methoxycarbonyloxy group, an ethoxycarbonyloxy group, a n-propoxycarbonyloxy group, an isopropoxycarbonyloxy group, a n-butoxycarbonyloxy group, a tert-butoxycarbonyloxy group, a n-pentyloxycarbonyloxy group, a n-hexyloxycarbonyloxy group, etc. are used, as the "$C_{6-10}$ aryloxy-carbonyloxy group", for example, a phenoxycarbonyloxy group, a naphthyloxycarbonyloxy group, etc. are used, as the "$C_{2-19}$ aralkyloxy-carbonyloxy group", for example, a benzyloxycarbonyloxy group, a 1-phenylethyloxycarbonyloxy group, a 2-phenylethyloxycarbonyloxy group, a benzhydryloxycarbonyloxy group, etc. are used, and as the "$C_{3-10}$ cycloalkyloxy-carbonyloxy group", for example, a cyclopropyloxycarbonyloxy group, a cyclohexyloxycarbonyloxy group, etc. are used.

As the "ureido group optionally having substituents", for example, an ureido group optionally substituted by 1 to 3 substituents selected from a $C_{1-4}$ alkyl group (e.g., a methyl group, an ethyl group, etc.), a phenyl group, etc. are used, and for example an ureido group, a 1-methylureido group, a 3-methylureido group, a 3,3-dimethylureido group, a 1,3-dimethylureido group, a 3-phenylureido group, etc. used.

When a heterocyclic group, a heterocyclic oxy group, a heterocyclic thio group, a heterocyclic sulfinyl group, a heterocyclic sulfonyl group or a heterocyclicoxycarbonyl group are used as the "substituents" of the "aliphatic hydrocarbon group optionally having substituents", the heterocyclic group represents a group formed by excluding one hydrogen atom which binds to the heterocycle, and it represents, for example, a 5- to 8-membered cyclic (preferably 5- to 6-membered cyclic) group containing 1 to a few, preferably 1 to 4 hetero atoms such as a nitrogen atom (optionally oxidized), an oxygen atom, a sulfur atom, etc., or a condensed cyclic group thereof. As these heterocyclic groups, for example, a pyrrolyl group, a pyrazolyl group, an imidazolyl group, a 1,2,3-triazolyl group, a 1,2,4-triazolyl group, a tetrazolyl group, a furyl group, a thienyl group, an oxazolyl group, an isooxazolyl group, a 1,2,3-oxadiazolyl group, a 1,2,4-oxadiazolyl group, a 1,2,5-oxadiazolyl group, a 1,3,4-oxadiazolyl group, a thiazolyl group, an isothiazolyl group, a 1,2,3-thiadiazolyl group, a 1,2,4-thiadiazolyl group, a 1,2,5-thiadiazolyl group, a 1,3,4-thiadiazolyl group, a pyridyl group, a pyridazinyl group, a pyrimidinyl group, a pyrazinyl group, an indolyl group, a pyranyl group, a thiopyranyl group, a dioxynyl group, a dioxolyl group, a quinolyl group, a pyrido[2,3-d]pyrimidinyl group, 1,5-, 1,6-, 1,7-, 1,8-, 2,6- or 2,7-naphthyridyl group, a thieno[2,3-d]pyridyl group, a benzopyranyl group, a tetrahydrofuryl group, a tetrahydropyranyl group, a dioxolanyl group, a dioxanyl group, etc. are used.

These heterocyclic groups may be substituted at possible positions by 1 to 3 substituents selected by from $C_{1-4}$ alkyl (e.g., methyl, ethyl, etc.), hydroxy, oxo, $C_{1-4}$ alkoxy (e.g., methoxy, ethoxy, etc.), etc.

As the "$C_{6-10}$ aryl group" the "$C_{6-10}$ aryl group optionally having substituents", for example, a phenyl group, a naphthyl group, etc. are used. The $C_{6-10}$ aryl group may be substituted at a substitutable position by a substituent selected from the those listed as a "substituent" (except for an optionally substituted $C_{6-10}$ aryl group) of the "aliphatic hydrocarbon optionally having substituents" described above. Such a substituent is substituted at a substitutable position in a $C_{6-10}$ aryl group, and the number of such substituents is not limited to one, and, the same or different, more than one (2 to 4) substituents may exist.

In the "aliphatic hydrocarbon group optionally having substituents", the substituent together with the aliphatic hydrocarbon group may form an optionally substituted fused ring group, and as these condensed ring groups, an indanyl group, a 1,2,3,4-tetrahydronaphthyl group, etc. are used. This condensed ring group may be substituted at a substitutable position by a substituent selected from the those listed as a "substituent" of the "aliphatic hydrocarbon optionally having substituents" described above. Such a substituent is substituted at a substitutable position in a fused ring group, and the number of such substituents is not limited to one, and, the same or different, more than one (2 to 4) substituents may exist.

As R, $R^1$, $R^{1a}$, $R^{1b}$, $R^{1c}$, for example, a lower alkyl group having 1 to 6 carbon atoms (e.g., a methyl group, an ethyl group, a n-propyl group, an isopropyl group, a n-butyl group, an isobutyl group, a t-butoxycarbonylmethyl group, a hydroxyethyl group and the like) optionally having substituents, and of them a methyl group, an ethyl group, a n-propyl group, an isopropyl group, a n-butyl group, an isobutyl group, etc. are preferably used. Particularly, a methyl group, an ethyl group, a n-propyl group and the like, etc. are prefered, and an ethyl group is preferred particularly.

As $R^2$, $R^{2a}$, for example, a hydrogen atom, a lower alkyl group having 1 to 6 carbon atoms (e.g., a methyl group, an ethyl group, a n-propyl group, an isopropyl group, a n-butyl group, an isobutyl group, a t-butoxycarbonylmethyl group, a hydroxyethyl group and the like), etc. are preferably used, and a hydrogen atom, a methyl group, etc. are preferably used and particularly a hydrogen atom, etc. are preferably used.

As the "aromatic hydrocarbon group" of the "aromatic hydrocarbon group optionally having substituents" represented by Ar, $Ar^a$, for example, an aromatic hydrocarbon group having 6 to 14 carbon atoms (e.g., a phenyl group, a naphthyl group, a biphenyl group, an anthryl group, an indenyl group and the like) and the like, and particularly an aryl group having 6 to 10 carbon atoms and the like (e.g., phenyl and naphthyl groups) are preferred and a phenyl group and the line are particularly preferred.

As the "substituent" of the "aromatic hydrocarbon group optionally having substituents" represented by Ar, $Ar^a$, for example, a halogen atom (e.g., fluorine, chlorine, bromine, iodine and the like), a lower ($C_{1-4}$) alkyl group (e.g., a methyl group, an ethyl group, a propyl group, a butyl group and the like), a lower ($C_{1-4}$) alkoxy group (e.g., a methoxy group, an ethoxy group, a propoxy group, a butoxy group and the like), a lower ($C_{1-4}$) alkoxycarbonyl group (e.g., a methoxycarbonyl group, an ethoxycarbonyl group, a propoxycarbonyl group, a butoxycarbonyl group and the like), a carboxyl group, a nitro group, a cyano group, a hydroxyl group, an acylamino group (e.g., an alkanoylamino group having 1 to 4 carbon atoms such as an acetylamino group, a propionylamino group, a butyrylamino group and the like), a cycloalkyl group having 3 to 6 carbon atoms (e.g., a cyclopropyl group, a cyclopentyl group and the like), an aryl group having 6 to 10 carbon atoms (e.g., a phenyl group, a naphthyl group, an indenyl group and the like), a halogeno-lower ($C_{1-4}$) alkyl group (e.g., a trifluoromethyl group, a trifluoroethyl group and the like), a halogeno-lower ($C_{1-4}$) alkoxy group (e.g., a trifluoromethoxy group, a 1,1,2,2-tetrafluoroethoxy group, a 2,2,3,3,3-pentafluoropropoxy group and the like), a lower ($C_{1-4}$) alkylthio group (e.g., a methylthio group, an ethylthio group, a propionylthio group and the like), a lower ($C_{1-4}$) alkylsulfonyl group (e.g., a methanesulfonyl group, an ethanesulfonyl group, a propanesulfonyl group and the like), a lower ($C_{1-4}$) alkanoyl group (e.g., a formyl group, an acetyl group, a propionyl group and the like), a 5-membered aromatic heterocyclic group (e.g., a 1,2,3-triazolyl group, a 1,2,4-triazolyl group, a tetrazolyl group, a thiazolyl group, an isothiazolyl group, an oxazolyl group, an isooxyazolyl group, a thiadiazolyl group, a thienyl group, a furyl group and the like), a carbamoyl group, a lower ($C_{1-4}$) alkyl-carbamoyl group (e.g., a methylcarbamoyl group, a dimethylcarbamoyl group, a propionylcarbamoyl group and the like), a lower ($C_{1-4}$) alkoxy-carbonyl-lower ($C_{1-4}$) alkyl-carbamoyl group (e.g., a butoxycarbonylmethylcarbamoyl group, an ethoxycarbonylmethylcarbamoyl group and the like), a 1,3-diacylguanidino-lower ($C_{1-4}$) alkyl group and the like (e.g., 1,3-diacetylguanidinomethyl, 1,3-bis-t-butoxycarbonylguanidinomethyl and the like) are used, and a halogen atom (e.g., fluorine, chlorine, bromine, iodine atoms and the like), a lower ($C_{1-4}$) alkyl group and the like (e.g., a methyl group, an ethyl group, a propyl group, a butyl group and the like) are preferably used, and a fluorine atom, a chlorine atom and a methyl group are more preferably used.

These substituents are substituted at substitutable positions in the aromatic hydrocarbon group, and the number of the substituents is preferably 1 to 5, more preferably 1 to 3, most preferably 1 to 2. When two or more of such substituents are present, they may be the same or different.

Typically, as Ar or $Ar^a$, for example, a phenyl group, a halogenophenyl group, a lower ($C_{1-4}$) alkylphenyl group, a lower ($C_{1-4}$) alkoxyphenyl group, a lower ($C_{1-4}$) alkoxycarbonylphenyl group, a carboxylphenyl group, a nitrophenyl group, a cyanophenyl group, a halogeno-lower ($C_{1-4}$) alkylphenyl group, a halogeno-lower ($C_{1-4}$) alkoxyphenyl group, a lower ($C_{1-4}$) alkanoylphenyl group, a 5-membered aromatic heterocycle-substituted phenyl group, a lower ($C_{14}$) alkoxy-carbonyl-lower ($C_{1-4}$) alkyl-carbamoylphenyl group, 1,3-diacylguanidino-lower ($C_{1-4}$) alkylphenyl group, a halogen- and lower ($C_{1-4}$) alkoxy-substituted phenyl a group, a halogen- and lower ($C_{1-4}$) alkoxycarbonyl-substitutedphenyl group, a halogen- and cyano-substituted phenyl group, a halogen- and 5-membered aromatic heterocycle-substituted phenyl group, a halogen- and lower ($C_{1-4}$) alkoxycarbonyl-lower ($C_{1-4}$) alkyl-carbamoyl-substituted phenyl group and the like are used.

As Ar or $Ar^a$, a halogenophenyl group, a lower ($C_{1-4}$) alkylphenyl group, a halogen- and lower ($C_{1-4}$) alkoxycarbonyl-substituted phenyl and the like are preferably used.

As Ar or $Ar^a$, a group represented by formula:

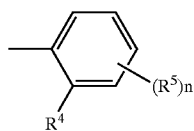

wherein $R^4$ and $R^5$ is the same or different and each represents a halogen atom or a lower alkyl group, and n is an integer of 0 to 2, with one in which at least one of $R^4$ and $R^5$ is a halogen atom being further preferred.

As the halogen atom represented by $R^4$ and $R^5$, a fluorine atom or a chlorine atom is preferred.

As the halogenophenyl group, for example, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorphenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorohenyl group and the like are used.

As the lower ($C_{1-4}$) alkylphenyl group, a 2-ethylphenyl group, a 2,6-diisopropylphenyl group and the like are preferably used, and as the lower ($C_{1-4}$) alkoxyphenyl group, for example, a 4-methoxyphenyl group and the like are preferably used.

As the halogenophenyl group, for example, a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 2-fluorophenyl group, a 2-chlorophenyl group, a 3-fluorophenyl group, a 3-chlorophenyl group, a 4-fluorophenyl group, a 4-chlorophenyl group, a 2-fluoro-4-chlorophenyl group, a 2-chloro-4-fluorophenyl group, a 4-bromo-2-fluorophenyl group, a 2,3,4-trifluorophenyl group, a 2,4,5-trifluorophenyl group, a 2,4,6-trifluorophenyl group and the like are used.

As the lower ($C_{1-4}$) alkanoylphenyl group, for example, a 2-acetylphenyl group and the like are preferably used, and as the 5-membered aromatic heterocycle-substituted phenyl, for example, a 4-(2H-1,2,3-triazol-2-yl)phenyl group, a 4-(2H-tetrazol-2-yl)phenyl group, a 4-(1H-tetrazol-1-yl) phenyl group, a 4-(1H-1,2,3-triazol-1-yl)phenyl group and the like are preferably used, and as the lower ($C_{1-4}$) alkoxy-carbonyl-lower ($C_{1-4}$) alkyl-carbamoylphenyl group, for example, a 4-(N-ethoxycarbonylmethylcarbamoyl)phenyl group and the like are preferably used, and as the 1,3-diacylguanidino-lower ($C_{1-4}$) alkylphenyl group, for example, a 4-(1,3-bis-t-butoxycarbonylguanidinomethyl) phenyl group and the like are preferably used.

As the phenyl group substituted by halogen and lower ($C_{1-4}$) alkyl, for example, a 2-fluoro-4-methylphenyl group, a 2-chloro-4-methylphenyl group, a 4-fluoro-2-methylphenyl group and the like are preferably used, and as the phenyl group substituted by halogen and lower ($C_{1-4}$) alkoxycarbonyl, for example, a 2-chloro-4-methoxycarbonylphenyl group and the like are preferably used, and the phenyl group substituted by halogen and cyano, for example, a 2-chloro-4-cyanophenyl group and the like are preferably used, and as the phenyl group substituted by halogen and 5-membered aromatic heterocycle, for example, a 2-fluoro-4-(1H-1,2,4-triazol-1-yl)phenyl group and the like are preferably used, and as the phenyl group substituted by halogen and lower ($C_{1-4}$) alkoxycarbonyl-lower ($C_{1-4}$) alky-carbamoyl, for example, a 2-chloro-4-(N-t-butoxycarbonylmethylcarbamoyl)phenyl group, a 2-chloro-4-(N-ethoxycarbonylmethylcarbamoyl)phenyl group and the like are preferably used.

More specifically, as Ar or $Ar^a$, a phenyl group, a phenyl group substituted with 1 to 3 (particularly 1 to 2) halogen atoms (e.g., a 2,3-difluorophenyl group, a 2,3-dichlorophenyl group, a 2,4-difluorophenyl group, a 2,4-dichlorophenyl group, a 2,5-difluorophenyl group, a 2,5-dichlorophenyl group, a 2,6-difluorophenyl group, a 2,6-dichlorophenyl group, a 3,4-difluorophenyl group, a 3,4-dichlorophenyl group, a 3,5-difluorophenyl group, a 3,5-dichlorophenyl group, a 4-bromo-2-fluorophenyl group, a 2-fluorophenyl group, a 2-chlorophenyl group, a 3-fluorophenyl group, a 3-chlorophenyl group, a 4-fluorophenyl group, a 4-chlorophenyl group, a2-fluoro-4-chlorophenyl group, a 2-chloro-4-fluorophenyl group, a 2,3,4-trifluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferred. Of them, a phenyl group substituted with 1 to 3 (particularly 1 to 2) halogen atoms (e.g., a 2,3-dichlorophenyl group, a 2,4-difluorophenyl group, a 2,4-dichlorophenyl group, a 2,6-dichlorophenyl group, a 2-fluorophenyl group, a 2-chlorophenyl group, a 3-chlorophenyl group, a 2-chloro-4-fluorophenyl group, a 2,4,5-trifluorophenyl group and the like), a phenyl group substituted by halogen and lower ($C_{1-4}$) alkyl (e.g., a 2-chloro-4-methylphenyl group, a 4-fluoro-2-methylphenyl group and the like), etc. are preferred. Particularly, a 2,4-difluorophenyl group, a 2-chlorophenyl group, a 2-chloro-4-fluorophenyl group, a 2-chloro-4-methylphenyl group and the like are preferred, and a 2,4-difluorophenyl group, a 2-chloro-4-fluorophenyl group and the like are preferred.

In this specification, the ring A represents (i) an aliphatic hydrocarbon group optionally having substituents, (ii) an aromatic hydrocarbon group optionally having substituents, (iii) a group represented by formula $OR^1$ (wherein $R^1$ is as defined above) and (iv) a cycloalkene substituted by 1 to 4 halogen atoms, and (i) an aliphatic hydrocarbon group optionally having substituents, (ii) an aromatic hydrocarbon group optionally having substituents and (iv) a cycloalkene substituted by 1 to 4 halogen atoms are preferred.

These substituents are substituted on substitutable carbon atoms in a ring A, and when the ring A is substituted by two or more of such substituents, the substituents may be the same or different. A single carbon atom may be substituted by two substituents and different carbon atoms may be substituted by two or more substituents.

As the "aliphatic hydrocarbon group optionally having substituents" as a substituent on the ring A, for example, the same those as the "aliphatic hydrocarbon group optionally having substituents" represented by R, $R^1$, $R^{1a}$, $R^{1b}$, $R^{1c}$ described above may be used.

As the "aromatic hydrocarbon group optionally having substituents" as a substituent on the ring A, for example, the same those as the "aromatic hydrocarbon group optionally having substituents" represented by Ar or $Ar^a$ described above may be used.

As the "heterocyclic group optionally having substituents" as a substituent on the ring, for example, the same thise ents" as the "heterocyclic group" which is a "substituent" on the "aliphatic hydrocarbon group optionally having substituents" represented by R, $R^1$, $R^{1a}$, $R^{1b}$, $R^{1c}$.

As the substituents for the ring A, 1 or 2 $C_{1-6}$ alkyl group (e.g., a $C_{1-4}$ alkyl group such as a methyl group, a tert-butyl group, etc.), a phenyl group, a halogen atom (e.g., florine, chlorine, bromine, iodine, etc.), etc. are preferably used.

The group represented by the formula:

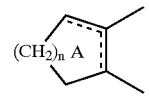

wherein n represents the same meaning as defined above, represents a group represented by the formula:

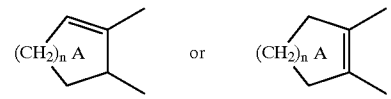

wherein n represents the same meaning as defined above, and preferably a group represented by the formula:

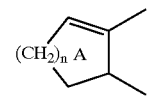

The group represented by the formula:

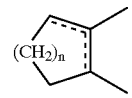

wherein n represents the same meaning as defined above, represents a group represented by the formula:

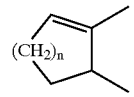

wherein n represents the same meaning as defined above, and preferably a group represented by the formula:

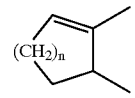

And, the group represented by the formula:

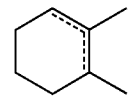

represents a group represented by the formula:

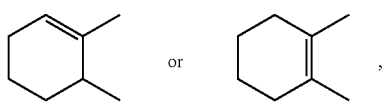

and preferably a group represented by the formula:

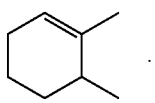

As the integer of 1 to 4 represented by n, 1 to 3 is preferred and 2 is more preferred.

As the compound represented by the formula (Iaa), the compound represented by the formula (Ibb) is preferred, and as the compound represented by the formula (Ia), the compound represented by the formula (Ib) is preferred.

As the compound represented by the formula (Ibb), the compound represented by the formula (Inn) is preferred, and as the compound represented by the formula (Ib), the compound represented by the formula (In) is preferred.

As the compound (Ibb), (Ib), a compound wherein $R^1$ is a lower alkyl group optionally having substituents, $R^2$ is a hydrogen atom or a lower alkyl group, Ar is a phenyl group optionally having substituents, n is 1, 2 or 3 is preferred, and a compound wherein $R^1$ is a lower alkyl group optionally having substituents, $R^2$ is a hydrogen atom, Ar is a phenyl group substituted by a halogen atom, n is 2 is more preferred, As the compound represented by the formula (Icc), (Ic), a compound wherein Ar is a phenyl group optionally having substituents, n is 2 is preferred.

As the leaving group represented by $X^1$, for example, a halogen atom (e.g., chlorine, bromine, iodine, etc.), etc. are preferred and a chlorine atom is more preferred.

When the compounds represented by formulae (Iaa), (Ibb), (Icc), (Ia), (Ib), (Ic), (Id), (Ie), (If) and (Ig) have stereoisomers, any of such stereoisomers and mixtures thereof are included in the invention.

When a compound represented by formula (Iaa) is a compound represented by formula (Icc) or (Inn), when a compound represented by formula (Ia) is a compound represented by formula (Ic) or (In), when a compound represented by formula (Ie) is a compound represented by formula (Ik) or (Ip), when a compound represented by formula (Id) is a compound represented by formula (Ir), and when a compound represented by formula (Ig) is a compound represented by formula (It), then each compound can exist as an optical isomer with regard to the asymmetric carbon atom in a cycloalkene or cyclohexene ring, and any of such optical isomers and mixtures thereof are included in the invention.

A compound represented by formula (Ia) may preferably be d-ethyl 6-[N-(2,4-difluorophenyl)sulfamoyl]-1-cyclohexene-1-carboxylate, ethyl 6-[N-(2-chlorophenyl)sulfamoyl]-1-cyclohexene-1-carboxylate, ethyl 6-[N-(2-chloro-4-methylphenyl)sulfamoyl]-1-cyclohexene-1-carboxylate or d-ethyl 6-[N-(2-chloro-4-fluorophenyl)sulfamoyl]-1-cyclohexene-1-carboxylate as well as a salt thereof.

In the above mentioned formulae, methods for producing a compound represented by the formula:

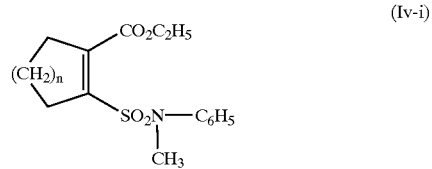

(Iv-i)

wherein n is 1 or 2, and a compound represented by the formula:

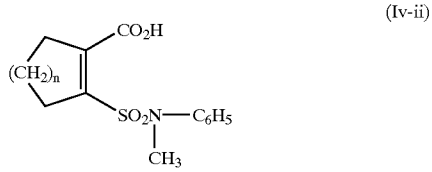

(Iv-ii)

wherein n is 1 or 2, are reported in Journal of American Chemical Society, Vol.101, pp6981–6991 (1979).

And, a method for producing a compound represented by the formula:

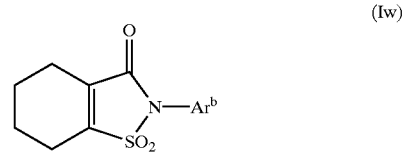

(Iw)

wherein $Ar^b$ is a phenyl group, a 2-methylphenyl group, a 4-bromophenyl group, a 4-methoxyphenyl group or a 2,6-dimethylphenyl group, is reported in Tetrahedron, Vol.52, pp783–790 (1996).

A method for producing an inventive compound (Ia), (Ib) or (Ic) or a salt thereof is discussed below.

While the following description of a production method may be applicable not only to an inventive compound (Ia), (Ib) or (Ic) but also to a salt thereof, the following description may sometimes employ a simple expression, i.e, Compound (Ia), (Ib) or (Ic). An inventive compound (Iaa), (Ibb) or (Icc) or a salt thereof can also be produced similarly.

While a method for producing Compound (Ia) wherein R is represented by formula $OR^1$ wherein $R^1$ is as defined above is described below, a compound wherein R is an optionally substituted aliphatic hydrocarbon group, an optionally substituted aromatic hydrocarbon group, an optionally substituted heterocyclic group, a group represented by the formula:

wherein each symbol is as defined above may also be produced similarly.

Compound (Ia) of the invention wherein R is represented by the formula $OR^1$ wherein $R^1$ is as defined above and $R^0$ is a hydrogen atom or an aliphatic hydrocarbon group, i.e., Compound (Ib), typically Compounds (In) and (Io) can, for example, be produced by reacting a compound represented by the formula:

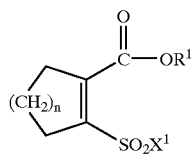
(IIa)

wherein each symbol is as defined above or a salt thereof with a compound represented by the formula:

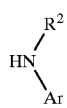
(IIIa)

wherein each symbol is as defined above or a salt thereof, or by subjecting a product obtained by a reaction of Compound (IIa) or a salt thereof with Compound (IIIa) or a salt thereof to a hydrolysis known per se.

During the process of the reaction of Compound (IIa) with Compound (IIIa), a group of Compound (IIa) represented by the formula:

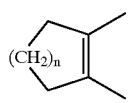

wherein n is as defined above may be isomerized into a group represented by the formula:

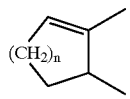

wherein n is as defined above, resulting in the production of a compound (Ib) wherein a group represented by the formula:

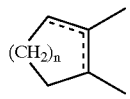

wherein n is as defined above is a group represented by the formula:

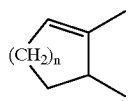

wherein n is as defined above, i.e., a compound represented by the formula (In).

A reaction of Compound (IIa) or a salt thereof with Compound (IIIa) or a salt thereof can be performed in the absence or presence of a base in a solvent which does not affect the reaction adversely or using no solvent. In this reaction, the amount of Compound (IIIa) or a salt used is preferably about 1 to about 5 times (molar ratio), more preferably about 1 to about 2 times (molar ratio) that of Compound (IIa) or a salt thereof. The base which can be employed may, for example, be an inorganic base (e.g., sodium hydride, potassium hydride, sodium hydroxide and the like), an organic base (e.g., triethylamine, pyridine, diisopropylethylamine and the like), preferably an organic base such as triethylamine. The amount of a base, when used, is preferably about 0.5 to about 5 times (molar ratio), more preferably about 0.9 to about 2 times (molar ratio) that of Compound (IIa).

A solvent employed in the reaction of Compound (IIa) with Compound (IIIa) which does not affect the reaction adversely may, for example, be a sulfoxide (e.g., dimethyl sulfoxide and the like), an ether (e.g., diethyl ether, tetrahydrofuran, dioxane and the like), a nitrile (e.g., acetonitrile and the like), an aromatic hydrocarbon (e.g., benzene, toluene, xylene and the like), a halogenated hydrocarbon (e.g., dichloromethane, chloroform, 1,2-dichloroethane and the like), an ester (e.g., ethyl acetate), an amide (e.g., dimethylformamide, acetamide, dimethylacetamide, 1,3-dimethyl-2-imidazolidinone, 1-methyl-2-pyrrolidone and the like) and the like. Any of these solvent may be employed alone or in combination of two or more in an appropriate ratio.

A reaction of Compound (IIa) with Compound (IIIa) is performed at a temperature preferably of about −10° C. to 100° C., more preferably about 0° C. to 60° C. The reaction times range from about 0.5 to about 50 hours, preferably about 0.5 hours to about 30 hours.

Compound (In) and Compound (Io) which are the products of this reaction may be produced each as a single compound or in a mixture. When $R^2$ in Compound (Io) is a hydrogen atom, a ring closure reaction may proceed under some reaction and/or isolation conditions, resulting in a compound represented by the formula (Ii).

Compound (Ib) of the invention wherein $R^2$ is an "optionally substituted aliphatic hydrocarbon group" can, for example, be produced by reacting a compound represented by the formula:

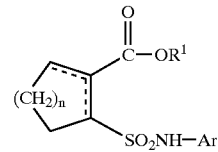
(Ix)

wherein each symbol is as defined above or a salt thereof with a compound represented by the formula:

$$R^{2b}-X^2 \qquad (IIIb)$$

wherein $X^2$ is a leaving group (e.g., a halogen atom (e.g., chlorine, bromine, iodine atoms and the like) or a group represented by the formula $-O_3SR^3$ wherein $R^3$ is a lower alkyl group having 1 to 4 carbon atoms or an optionally substituted phenyl group, and $R^{2b}$ is an optionally substituted aliphatic hydrocarbon group and the like, or by subjecting a product obtained by a reaction of Compound (Ix) or a salt thereof with Compound (IIIa) or a salt thereof to a hydrolysis known per se.

A reaction of Compound (Ix) or a salt thereof with Compound (IIIb) can be performed in the absence or presence of a base in a solvent which does not affect the reaction adversely or using no solvent. In this reaction, the amount of Compound (IIIb) used is preferably about 1 to about 5 times (molar ratio), more preferably about t to about 2 times (molar ratio) that of Compound (Ix). The base which can be employed may, for example, be an inorganic base (e.g., potassium carbonate, sodium hydride, potassium hydride, sodium hydroxide and the like), an organic base (e.g., triethylamine, pyridine, diisopropylethylamine and the like). The amount of a base, when used, is preferably about 0.5 to about 5 times (molar ratio), more preferably about 0.9 to about 2 times (molar ratio) that of Compound (Ix).

A solvent employed in the reaction of Compound (Ix) with Compound (IIIb) which does not affect the reaction adversely may, for example, be a sulfoxide (e.g., dimethyl sulfoxide and the like), an ether (e.g., diethyl ether, tetrahydrofuran, dioxane and the like), a nitrile (e.g., acetonitrile and the like), an aromatic hydrocarbon (e.g., benzene, toluene, xylene and the like), a halogenated hydrocarbon (e.g., dichloromethane, chloroform, 1,2-dichloroethane and the like), an ester (e.g., ethyl acetate), an amide (e.g., dimethylformamide, acetamide, dimethylacetamide, 1,3-dimethyl-2-imidazolidinone, 1-methyl-2-pyrrolidone and the like) and the like. Any of these solvent may be employed alone or in combination of two or more in an appropriate ratio.

A reaction of Compound (Ix) with Compound (IIb) is performed at a temperature preferably of about −10° C. to 100° C., more preferably about 0° C. to 60° C. The reaction times range from about 0.1 to about 50 hours, preferably about 0.5 hours to about 10 hours.

Compound (Ib) of the invention wherein $R^1$ is an "optionally substituted aliphatic hydrocarbon group" can, for example, be produced by reacting a compound represented by the formula:

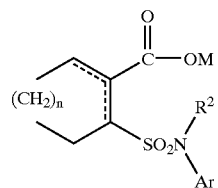

(Iy)

wherein M is a hydrogen atom or an alkaline metal (e.g., lithium, sodium, potassium and the like, and each of the other symbols is as defined above or a salt thereof with a compound represented by the formula:

$R^1$—$X^2$  (IIIc)

wherein each symbol is as defined above or a salt thereof.

A reaction of Compound (Iy) with Compound (IIIc) can be performed in the absence or presence of a base in a solvent which does not affect the reaction adversely or using no solvent. In this reaction, the amount of Compound (IIIc) used is preferably about 1 to about 10 times (molar ratio), more preferably about 1 to about 5 times (molar ratio) that of Compound (Iy). The base which can be employed may, for example, be an inorganic base (e.g., sodium hydride, potassium hydride, sodium hydroxide and the like), an organic base (e.g., triethylamine, pyridine, diisopropylethylamine and the like). The amount of a base, when used, is preferably about 0.5 to about 5 times (molar ratio), more preferably about 0.9 to about 2 times (molar ratio) that of Compound (Iy).

A solvent employed in the reaction of Compound (Iy) with Compound (IIIc) which does not affect the reaction adversely may, for example, be a sulfoxide (e.g., dimethyl sulfoxide and the like), an ether (e.g., diethyl ether, tetrahydrofuran, dioxane and the like), a nitrile (e.g., acetonitrile and the like), an aromatic hydrocarbon (e.g., benzene, toluene, xylene and the like), a halogenated hydrocarbon (e.g., dichloromethane, chloroform, 1,2-dichloroethane and the like), an ester (e.g., ethyl acetate), an amide (e.g., dimethylformamide, acetamide, dimethylacetamide, 1,3-dimethyl-2-imidazolidinone, 1-methyl-2-pyrrolidone and the like) and the like. Any of these solvent may be employed alone or in combination of two or more in an appropriate ratio.

A reaction of Compound (Iy) with Compound (IIIc) is performed at a temperature preferably of about −10° C. to 150° C., more preferably about 0° C. to 120° C. The reaction times ranges from about 0.5 to about 50 hours, preferably about 0.5 hours to about 30 hours.

Compound (Ib) of the invention wherein $R^1$ is a lower ($C_{1-4}$) alkyl group can be produced by reacting a compound represented by the formula:

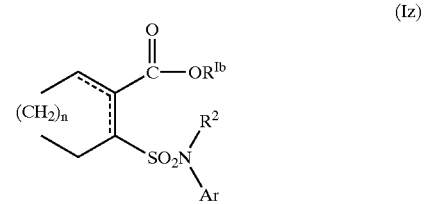

(Iz)

wherein $R^{1b}$ is a hydrogen atom of a lower ($C_{1-6}$) alkyl group, and each of the other symbols is as defined above or a salt thereof with a compound represented by the formula:

$R^{1c}$—OH  (IIId)

wherein $R^{1c}$ is a lower ($C_{1-6}$) alkyl group.

A reaction of Compound (Iz) with Compound (IIId) can be performed in the presence of an acid in a solvent which does not affect the reaction adversely or using no solvent. In this reaction, Compound (IIId) is used in excess of Compound (Iz), usually in an amount greater by about 10 to about 300 times (molar ratio). The acid which can be employed may for example be an inorganic acid (e.g., sulfuric acid, hydrochloric acid, phosphoric acid and the like) or an organic acid (e.g., toluenesulfonic acid, benzenesulfonic acid, methanesulfonic acid and the like), and the amount used is preferably about 0.001 to about 50 times (molar ratio), more preferably about 0.1 to about 5 times (molar ratio) that of Compound (Iz).

A solvent employed in the reaction of Compound (Iz) with Compound (IIId) which does not affect the reaction adversely may, for example, be a sulfoxide (e.g., dimethyl sulfoxide and the like), an ether (e.g., diethyl ether, tetrahydrofuran, dioxane and the like), a nitrile (e.g., acetonitrile and the like), an aromatic hydrocarbon (e.g., benzene, toluene, xylene and the like), a halogenated hydrocarbon (e.g., dichloromethane, chloroform, 1,2-dichloroethane and the like), an amide (e.g., dimethylformamide, acetamide, dimethylacetamide, 1,3-dimethyl-2-imidazolidinone, 1-methyl-2-pyrrolidone and the like) and the like. Any of these solvent may be employed alone or in combination of two or more in an appropriate ratio.

A reaction of Compound (Iz) with Compound (IIId) is performed at a temperature preferably of about 0° C. to 150° C., more preferably about 10° C. to 120° C. The reaction times range from about 1 to about 300 hours, preferably about 10 hours to about 200 hours. Compound (Ia) of the invention wherein R and R0 together form a bond and a group represented by the formula:

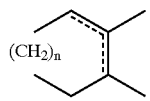

wherein n is as defined above is a group represented by the formula:

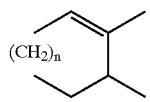

wherein n is as defined above, i.e., Compound (Ic) can, for example, be produced by subjecting a compound represented by the formula:

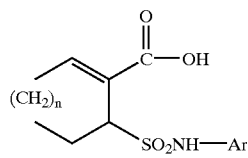

(IIb)

wherein each symbol is as defined above or a salt thereof to a ring closure reaction. Such a ring closure reaction can usually be performed by a procedure employed for dehydrating a carboxyl group and an amino group to condense into an amido bond, such as one described in "Izumiya et.al., Basics and Expeiments of Peptide Synthesis, Maruzen (1985)".

More typically, such a ring closure reaction can be performed by bringing Compound (IIb) into contact with a condensing agent in a solvent which does not affect the reaction adversely in the presence or absence of a base and in the presence and absence of an additive.

A solvent employed in this reaction which does not affect the reaction adversely may, for example, be a sulfoxide (e.g., dimethyl sulfoxide and the like), an ether (e.g., diethyl ether, tetrahydrofuran, dioxane and the like), a nitrile (e.g., acetonitrile and the like), an aromatic hydrocarbon (e.g., benzene, toluene, xylene and the like), a halogenated hydrocarbon (e.g., dichloromethane, chloroform, 1,2-dichloroethane and the like), an ester (e.g., ethyl acetate and the like), an amide (e.g., dimethylformamide, acetamide, dimethylacetamide, 1,3-dimethyl-2-imidazolidinone, 1-methyl-2-pyrrolidone and the like) and the like. Any of these solvent may be employed alone or in combination of two or more in an appropriate ratio.

Such a base may, for example, be an organic base (e.g., triethylamine, pyridine, diisopropylamine and the like) and the like. The amount of a base, when used, is preferably about 0.01 to about 100 times (molar ratio), more preferably about 0.1 to about 10 times (molar ratio) that of Compound (IIb).

The additive which can be employed as described above may, for example, be an active esterificating agent (e.g., 1-hydroxybenzotriazole, N-hydroxysuccinimide and the like). The amount of an additive, when used, is preferably about 0.01 to about 100 times (molar ratio), more preferably about 0.1 to about 10 times (molar ratio) that of Compound (IIb).

A condensing agent may, for example, be N,N'-dicyclohexycarbodiimide, 1-ethyl-3-(3-dimethylaminopropyl)carbodiimide, diethyl cyanophosphate, diphenylphosphorylazide and carbonyldiimidazole, with N.N'-dicyclohexylcarbodiimide and diethyl cyanophosphate being preferred particularly. The amount of a condensing agent, when used, is preferably about 0.01 to about 100 times (molar ratio), more preferably about 0.1 to about 10 times (molar ratio) that of Compound (IIb). The reaction temperature is preferably about −10° C. to 100° C., more preferably about 0° C. to 50° C. The reaction times range from about 0.5 to about 50 hours, preferably about 0.5 hours to about 30 hours.

An inventive Compound (Iaa), (Ibb), (Icc), (Ia), (Ib) or (Ic) thus obtained can be isolated and purified by a method known per se such as extraction, condensation, neutralization, filtration, crystallization, recrystallization, chromatography and the like.

When an inventive Compound (Iaa), (Ibb), (Icc), (Ia), (Ib) or (Ic) thus obtained is a compound which is a mixture of the two compounds in each of which a group represented by the formula:

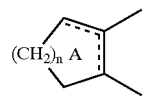

wherein n is as defined above is a group represented by the formula:

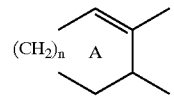

wherein n is as defined above and is a group represented by the formula:

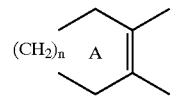

wherein n is as defined above, respectively, then the separation may be conducted by a known isomer separation method such as silica gel chromatography using ethyl acetate/water as an eluent, an octadecyl column chromatography using methanol/water/acetic acid, and the like.

Also when a product is a mixture of the two compounds in each of which a group represented by the formula:

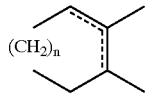

wherein n is as defined above is a group represented by the formula:

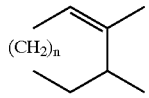

wherein n is as defined above, and a group represented by the formula:

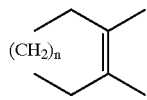

wherein n is as defined above, respectively, then the separation may similarly be accomplished.

A prodrug for an inventive Compound (Iaa) or (Ia) is a compound which is converted into Compound (Iaa) or (Ia) under a physiological condition as a result of a reaction with an enzyme or gastric acid, thus a compound undergoing an enzymatic oxidation, reduction or hydrolyzation to form Compound (Iaa) or (Ia) and a compound hydrolyzed by gastric acid to form Compound (Iaa) or (Ia). A prodrug for Compound (Iaa) or (Ia) may, for example, be a compound obtained by subjecting an amino group in Compound (Iaa) or (Ia) to an acylation, alkylation or phosphorylation (e.g., a compound obtained by subjecting an amino group in Compound (Iaa) or (Ia) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation); a compound obtained by subjecting a hydroxy group in Compound (Iaa) or (Ia) to an acylation, alkylation, phosphorylation and boration (e.g., a compound obtained by subjecting a hydroxy group in Compound (Iaa) or (Ia) to an acetylation, palmitoylation, propanoylation, pivaloylation, succinylation, fumarylation, alanylation and dimethylaminomethylcarbonylation); a compound obtained by subjecting a carboxyl group in Compound (Iaa) or (Ia) to an esterification or amidation (e.g, a compound obtained by subjecting a carboxyl group in Compound (Iaa) or (Ia) to an ethylesterification, phenylesterification, carboxymethylesterification, dimethylaminomethylesterification, pivaloyloxymethylesterification, ethoxycarbonyloxyethylesterification, phthalidylesterification, (5-methyl-2-oxo-1,3-dioxolen-4-yl)methylesterification, cyclohexyloxycarbonylethyl-esterification and methylamidation) and the like. Any of these compounds can be produced from Compound (Iaa) or (Ia) by a method known per se.

A prodrug for Compound (Iaa) or (Ia) may also be one which is converted into Compound (Iaa) or (Ia) under a physiological condition, such as those described in "IYAKUHIN no KAIHATSU (Development of Pharmaceuticals)", Vol.7, Design of Molecules, p.163–198, Published by HIROKAWA SHOTEN (1990).

Alternatively, an inventive Compound (Iaa), (Ibb), (Icc), (Ia), (Ib) or (Ic) or Compound (Ie) may, for example, be converted into a salt with an inorganic base, organic base, inorganic acid, organic acid, basic or acidic amino acid. A salt with an inorganic base may, for example, be an alkaline metal salt such as sodium and potassium salts, an alkaline earth metal salt such as calcium and magnesium salts, aluminum and ammonium salts, and a salt with an organic base may, for example, be a salt with trimethylamine, triethylamine, pyridine, picoline, ethanolamine, diethanolamine, triethanolamine, dicyclohexylamine or N,N'-dibenzylethylenediamine. A salt with an inorganic acid may, for example, be a salt with hydrochloric acid, hydrobromic acid, nitric acid, sulfuric acid or phosphoric acid, and a salt with an organic acid may, for example, be a salt with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. A salt with a basic amino acid may, for example, be a salt with arginine, lysine or ornithine, and a salt with acidic amino acid may, for example, be a salt with aspartic acid or glutamic acid.

Furthermore, a prodrug for an inventive Compound in (Iaa) or (Ia) may also be converted into a similar salt.

An inventive Compound (Iaa), (Ibb), (Icc), (Ia), (Ib) or (Ic) or Compound (Ie) may be a hydrate or an anhydride, and a prodrug for an inventive Compound (Iaa) or (Ia) may also be a hydrate or an anhydride.

Furthermore, an inventive Compound (Iaa), (Ibb), (Icc), (Ia), (Ib) or (Ic) or Compound (Ie) may be labeled with a radioisotope (e.g. , $^3$H, $^{14}$C, $^{35}$S, $^{225}$I and the like), and a prodrug for an inventive Compound (Iaa) or (Ia) may also be labeled similarly.

When an asymmetric carbon atom is present in a cycloalkene ring in an inventive Compound (Iaa), (Ibb), (Ia) or (Ib), Compound (Inn), (Icc), (In) or (Ic) can, for example, be present as any of at least two stereoisomers (optical isomers) as discribed above, which can be produced separately if necessary.

For example, a single isomer represented by the formula:

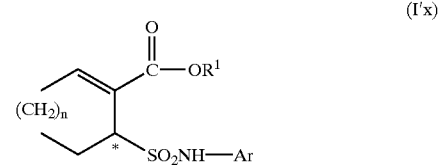

(I'x)

wherein each symbol is as defined above, or by the formula:

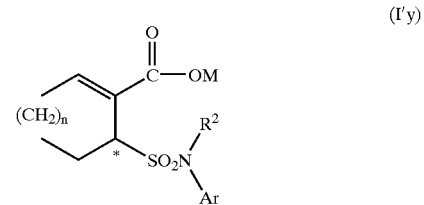

(I'y)

wherein each symbol is as defined above, or by the formula:

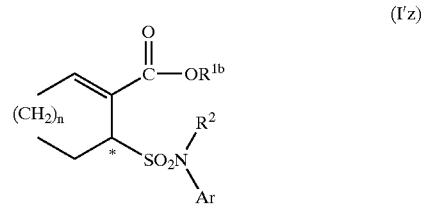

(I'z)

wherein each symbol is as defined above, in which a group represented by the formula:

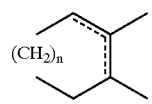

wherein n is as defined above in a starting Compound (Ix), (Iy) or (iz) is a group represented by the formula:

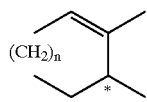

wherein n is as defined above and * represents a single steric configuration of the designated carbon atom or a single isomer of a compound represented by the formula (IIb), i.e., a compound represented by the formula:

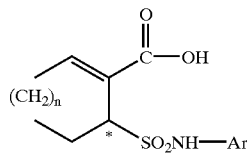

(II'b)

wherein each symbol is as defined above can be employed to perform the reaction described above to obtain a single isomer of inventive Compound (In) or (Ic).

When Compound (Inn), (Icc), (In) or (Ic) is a mixture of two or more isomers, an ordinary separation method, such as a method in which a salt with an optically active acid (e.g., camphorsulfonic acid and the like) or an optically active base (e.g., 1-methylbenzylamine and the like) is formed, various chromatographic methods (e.g., a liquid chromatography on an optically active column) and a fractional recrystalization may be employed to resolve into discrete isomers.

A compound represented by the formula (IIa), (IIIa), (Ix), (IIIb), (Iy), (IIIc), (Iz), (IIb), (I'x), (I'y), (I'z) or (II'b) can also be used as a salt, and such salt of each of these compounds may be any of the salts which do not affect the reaction adversely, such as a salt with an inorganic base, organic base, inorganic acid, organic acid, basic or acidic amino acid. A salt with an inorganic base may, for example, be an alkaline metal salt such as sodium and potassium salts, an alkaline earth metal salt such as calcium and magnesium salts, aluminum and ammonium salts, and a salt with an organic base may, for example, be a salt with trimethylamine, triethylamine, pyridine, picoline, ethanolamine, diethanolamine, triethanolamine, dicyclohexylamine or N,N'-dibenzylethylenediamine. A salt with an inorganic acid may, for example, be a salt with hydrochloric acid, hydrobromic acid, nitric acid, sulfuric acid or phosphoric acid, and a salt with an organic salt may, for example, be a salt with formic acid, acetic acid, trifluoroacetic acid, fumaric acid, oxalic acid, tartaric acid, maleic acid, citric acid, succinic acid, malic acid, methanesulfonic acid, benzenesulfonic acid or p-toluenesulfonic acid. A salt with a basic amino acid may, for example, be a salt with arginine, lysine or ornithine, and a salt with acidic amino acid may, for example, be a salt with aspartic acid or glutamic acid.

Compound (IIe) which is a starting compound (IIa) in the invention wherein $R^1$ is ethyl and $X^1$ is a chlorine atom may, for example, be produced by a method represented by the following scheme.

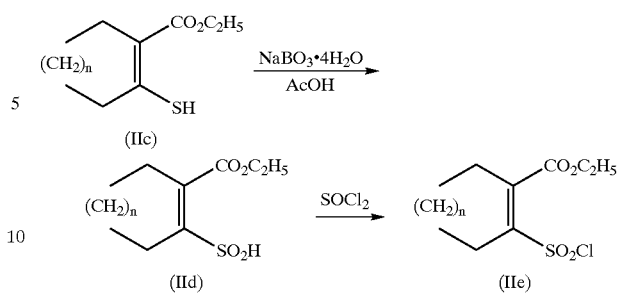

A method for producing a starting Compound (IIc) in this scheme is known per se, and may, for example, be in accordance with the description in Tetrahedron, Vol.28, p.5923 (1972) and Vol.30, p.3753 (1974) or analogous methods.

A method for producing a compound (IIa) wherein $R^1$ is ethyl, $X^1$ is a chlorine atom and wherein n is 1 represented by the formula:

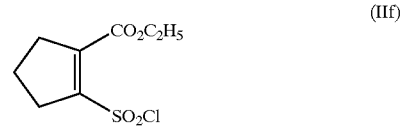

(IIf)

and wherein n is 2 represented by the formula:

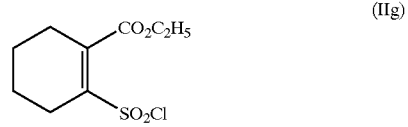

(IIg)

is known per se, and may, for example, be in accordance with the description in Journal of the American Chemical Society, Vol.101, p.6981 (1979) or analogous methods.

A method for producing a compound (IIa) wherein $R^1$ is methyl, $X^1$ is a chlorine atom and n is 2 represented by the formula:

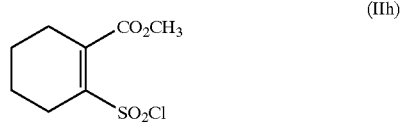

(IIh)

is known per se, and may, for example, be in accordance with the description in Bioorganic and Medicinal Chemistry Letters, Vol.5, p.325 (1995) or analogous methods.

In order to produce other compounds encompassed in a starting Compound (IIa), a method described above or analogous methods can be employed.

A starting Compound (IIb) or (Iy) in the invention can, for example, be produced by a method represented by the following schemes.

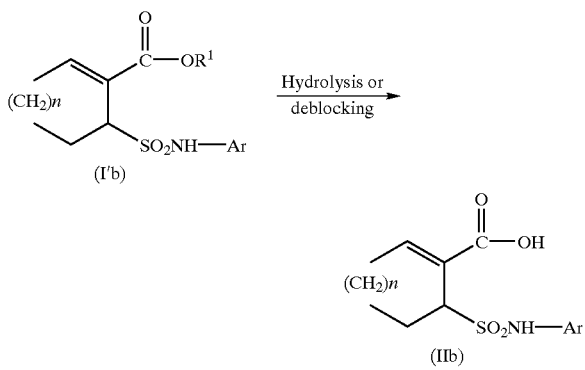

wherein each symbol is as defined above, and

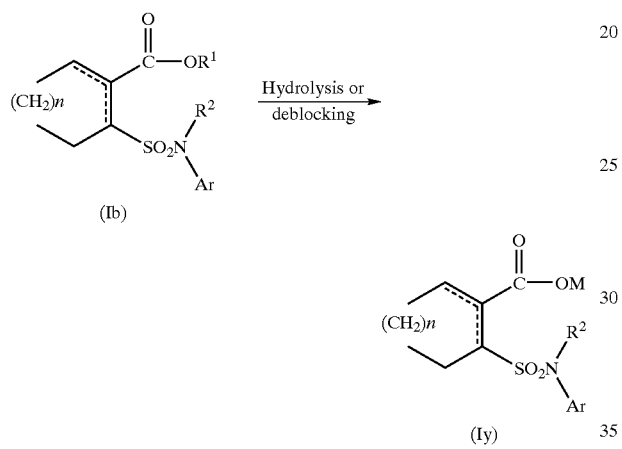

wherein each symbol is as defined above.

A method for producing Compound (Iy) wherein M is a hydrogen atom, $R^2$ is a methyl group, Ar is a phenyl group, n is 2 and a group represented by the formula:

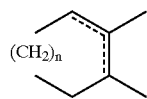

is a group represented by the formula:

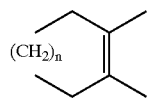

which is a compound represented by the formula:

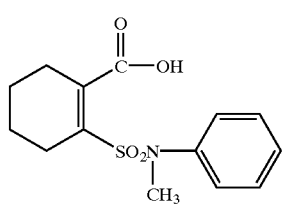

is known per se, and may be in accordance with the description in Journal of the American Chemical Society, Vol.101, p.6981 (1979) or analogous methods.

A starting compound or an intermediate obtained as described above can be isolated and purified from a reaction mixture by a method known per se, such as extraction, concentration, neutralization, filtration, crystallization, recrystallization, column chromatography, thin layer chromatography and the like. It may also be used directly in the next step without any isolation.

When a resultant starting material or an intermediate is a mixture of the two compounds in each of which a group represented by the formula:

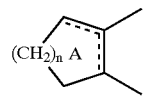

wherein n is as defined above is a group represented by the formula:

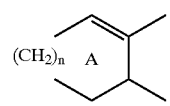

wherein n is as defined above and is a group represented by the formula:

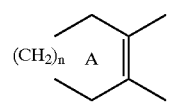

wherein n is as defined above, respectively, then the separation may be conducted by a known isomer separation method such as silica gel chromatography using ethyl acetate/water as an eluent, an octadecyl column chromatography using methanol/water/acetic acid as an eluent, and the like.

Also when a product is a mixture of the two compounds in each of which a group represented by the formula:

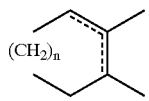

wherein n is as defined above is a group represented by the formula:

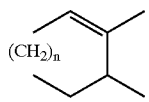

wherein n is as defined above and is a group represented by the formula:

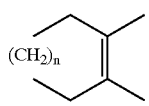

wherein n is as defined above, respectively, then the separation may similarly be accomplished.

Since an inventive Compound (Iaa) or Compound (Ie) has a low toxicity, an nitric oxide (NO) production-inhibiting effect and an inhibitory effect on the production of an inflammatory cytokine such as TNF-α, IL-1 and IL-6, it is useful as a therapeutic and/or prophylactic agent in a mammal (e.g., cat, cattle, dog, horse, goat, monkey, human and the like) against heart disease, autoimmune disease, inflammatory disease, central nervous system disease, infectious disease, sepsis, septic shock including ichorrhemia, endotoxin shock, exotoxin shock, cardiac deficiency, shock, hypotension, rheumatoid arthritis, osteoarthritis, gastritis, ulcerative colitis, peptic ulcer, stress-induced gastric ulcer, Crohn's disease, autoimmune disease, post-transplant tissue failure and rejection, postischemic re-perfusion failure, acute coronary microvascular embolism, shock-induced vascular embolism (disseminated intravascular coagulation (DIC) and the like), ischemic cerebral disorder, arterial sclerosis, malignant anemia, Fanconi's anemia, drepanocythemia, pancreatitis, nephrose syndrome, nephritis, renal failure insulin-dependent diabetes, insulin-independent diabetes, hepatic porphyria, alcoholism, Parkinson's disease, chronic leukemia, acute leukemia, tumor, myeloma, side effects of anticancer agents, infantile and adult respiratory distress syndrome, pulmonary emphysema, dementia, Alzheimer's disease, multiple sclerosis, vitamin E deficiency, aging, sunburn, muscular dystrophy, myocarditis, cardiomyopathy, myocardial infarction, sequela of myocardial infaction, osteoporosis, pneumonia, hepatitis, psoriasis, pain, cataract, influenza infection, malaria, human immunodeficiency virus (HIV) infection, radiation-induced failure, burn, in vitro fertilization efficiency, hypercalcemia, tonic spondylitis, osteopenia, bone Behcet's disease, osteomalacia, fracture, acute bacterial meningitis, Helicobactor pylori infection, invasive staphylococcal infection, tuberculosis, systemic mycosis, herpes simplex virus infection, varicella-helpes zoster virus infection, human papilloma virus infection, acute viral encephalitis, encephalitis, asthma, atopic dermatitis, allergic rhinitis, reflux esophargitis, fever, hyper cholesteremia, hyperglycemia, hyperlipidemia, diabetic complication, diabetic renal disease, diabetic neuropathy, diabetic retinopathy, gout, gastric atony, hemorrhoid, systemic lupus erythematosus, spinal damage, insomnia, schizophrenia, epilepsy, cirrhosis, hepatic failure, instable angina, valvular disease, dialysis-induced thrombocytopenia, acute ischemic cerebral apoplexy, acute cerebral thrombosis, cancer metastasis, urinary bladder cancer, mammary cancer, uterine cervical cancer, colon cancer, gastric cancer, ovarian cancer, prostatic cancer, parvicellular pulmonary cancer, non-parvicellular pulmonary cancer, malignant melanoma, Hodgkin's disease, non-Hodgkin lymphoma and the like.

When an inventive Compound (Iaa) or Compound (Ie) is administered to a human, it is given safely as it is or in a mixture with an appropriate pharmacologically acceptable carrier, excipient and diluent, in a dosage form such as an oral formulation (e.g., powder, granlue, tablet, capsule and the like), a parenteral formulation (e.g., injection formulation, dermal formulation (e.g., nasal formulation, percutaneous formulation and the like), suppository (e.g., rectal suppository and vaginal suppository and the like) as well as other oral or parenteral pharmaceutical composition.

Any of these formulations may be produced by any method known per se which is employed ordinarily for producing a pharmaceutical formulation. The amount of an inventive Compound (Iaa) or Compound (Ie) to be incorporated into a formulation may vary depending on the dosage forms, and is preferably about 10 to 95% by weight in an oral formulation described above and about 0.001 to about 95% by weight in a parenteral formulation described above.

For example, an injection formulation can be produced by formulating an inventive Compound (Iaa) or Compound (Ie) together with a solubilizing agent (e.g., β-cyclodextrin and the like), a dispersant (e.g.,, Tween 80 (ATLASPOWDER USA), HCO60 (NIKKO CHEMICALS), carboxymethyl cellulose, sodium alginate and the like), a preservative (e.g., methylparaben, propylparaben, benzyl alcohol, chlorobutanol and the like), an isotonic agent (e.g., sodium chloride, glycerin, sorbitol, glucose and the like) into an aqueous injection formulation in accordance with an ordinary method, or by suspending or emulsifying an active ingredient in a vegetable oil (e.g., olive oil, sesame oil, peanut oil, cottonseed oil, corn oil and the like) and propylene glycol to form an oil-based injection formulation.

An oral formulation can be produced by compressing an inventive Compound (Iaa) or Compound (Ie) together with an excipient (e.g., lactose, sucrose, starch and the like), a disintegrant (e.g., starch, calcium carbonate and the like), a binder (e.g., starch, gum arabic, carboxymethyl cellulose, polyvinyl pyrrolidone, hydroxypropyl cellulose and the like) or a glidant (e.g., talc, magnesium stearate, polyethylene glycol 6000 and the like) as appropriate followed by a coating process known per se for the purpose of masking a taste, forming an enteric coat, or achieving a sustained release. Such coating may, for example, be hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (ROHME, Germany, a copolymer of methacrylic acid and acrylic acid), a dye (e.g., titanium oxide, iron oxide red and the like) as appropriate.

An inventive Compound (Iaa) or Compound (Ie) can also be employed as a dermal formulation in the form of a solid or semi-solid or a liquid.

For example, a solid dermal formulation may be an inventive Compound (Iaa) or Compound (Ie) as it is or in a mixture with an excipient (e.g., glycol, mannitol, starch, microcrystalline cellulose and the like), a thickening agent (e.g., natural gums, cellulose derivatives, acrylic acid polymers and the like) which is then converted into a powder composition. A semi-solid dermal formulation may be produced by a standard method in the form of an aqueous or oil-based gel or ointment. A liquid dermal formulation may be produced by a method employed for producing an injection formulation or an analogous method in the form of an oil-based or aqueous suspension.

A solid, semi-solid or liquid dermal formulation may be supplemented also with a pH modifier (e.g., carbonated water, phosphoric acid, citric acid, hydrochloric acid, sodium hydroxide and the like), an antiseptic (e.g., p-oxybenzoates, chlorobutanol, benzalkonium chloride and the like) and the like, as appropriate. Typically, a vaseline or a lanolin is used as a formulation base, per 1 g of which about 0.1 to 100 mg of an inventive Compound (Iaa) or Compound (Ie) is contained to form an ointment.

An inventive Compound (Iaa) or Compound (Ie) may be formulated also as an oil-based or aqueous solid or semi-solid or liquid suppository. An oil-based suppository base may, for example, be a higher fatty glyceride (e.g., cocoa butter, WITEPSOL (DYNAMIT NOBEL) and the like), a middle fatty acid (e.g., MYGLYOL (DYNAMIT NOBEL) and the like), or a vegetable oil (e.g., sesame oil, soybean oil, cottonseed oil and the like) and the like as appropriate. An aqueous base may, for example, be a polyethylene glycols or a propylene glycol, and an aqueous gel base may, for example, be a natural gum, a cellulose derivative, a vinyl polymer, an acrylic polymer and the like.

While the dose of an inventive Compound (Iaa) or Compound (Ie) may vary depending on the patient's age, body weight and condition, the dosage form, the mode and the period of the treatment, it may, for example, be generally about 0.01 to about 1000 mg/kg, preferably about 0.01 to about 100 mg/kg, more preferably about 0.1 to about 100 mg/kg, most preferably about 0.1 to about 50 mg/kg, and particularly about 1.5 to about 30 mg/kg per day in a patient having a sepsis (adult weighing about 60 kg), said daily dose being given orally or parenterally all at once or in portions during a day. It is a matter of course that a lower daily dose may be sufficient or an excessive dose may be required since the dose may vary depending on various factors as discussed above.

BEST MODE FOR CARRYING OUT THE INVENTION

The present invention is further described with referring to Reference Examples, Examples, Preparation Examples and Experiments, which are not intended to restrict the invention.

A $^1$H NMR spectrum was determined by a VARIAN GEMINI 200 (200 MHz) spectrometer using tetramethyl silane as an internal standard and represented as the entire δ values in ppm. The number in a bracket when a solvent mixture was employed is the volume ratio of each mixture. A % is a % by weight unless otherwise specified. The ratio of the solvents in a chromatography on silica gel is the volume ratio of the solvents to be admixed.

A more polar diastereomer means a diastereomer having a smaller Rf value when determined by a normal phase thin layer chromatography under a same condition (for example using ethyl acetate/hexane as an eluent), which a less polar diastereomer means a diastereomer having a larger Rf value in such determination.

The meanings of the abbreviations as used in the Examples are as follows:

s: singlet d: doublet: t: triplet q: quartet DD: double doublet tt: triple triplet m: multiplet br: broad J: coupling constant

EXAMPLES

Reference Example 1

Sodium peroxyborate tetrahydrate (22.3 g) was admixed with acetic acid (120 ml) and heated to 50 to 55° C. and then a solution of ethyl 2-mercapto-1-cyclohexene-1-carboxylate (9.0 g) in acetic acid (15 ml) was added dropwise over 2 hours. The mixture was stirred at 50 to 55° C. for 3 hours and then at 80 to 85° C. for 5 hours and concentrated under reduced pressure. The residue was combined with acetonitrile (200 ml) and stirred at room temperature for 3 hours and the resultant insolubles were filtered off. The insolubles were washed with acetonitrile (50 ml) and the filtrate and the washing were combined and concentrated under reduced pressure, and the resultant residue was dissolved in acetonitrile (150 ml) and stirred at room temperature for 2 hours. The resultant insolubles were filtered off, and the filtrate was concentrated under reduced pressure. The residue was combined with diisopropyl ether (300 ml) and the powder which precipitated was isolated by filtration to obtain ethyl 2-sulfo-1-cyclohexene-1-carboxylate as a white powder (18.8 g) containing inorganic substances.

$^1$H-NMR (DMSO-$d_6$) δ: 1.17 (3H, t, J=7 Hz), 1.53 (4H, br), 2.08–2.09 (2H, m), 2.22–2.24 (2H, m), 3.99 (2H, q, J=7 Hz).

Reference Example 2

Sodium peroxyborate tetrahydrate (74.3 g) was admixed with acetic acid (400 ml) and heated to 50 to 55° C. and then a solution of ethyl 2-mercapto-1-cyclohexene-1-carboxylate (30.0 g) in acetic acid (50 ml) was added dropwise over 2 hours. The mixture was stirred at 50 to 55° C. for 3 hours and then at 80 to 85° C. for 5 hours and concentrated under reduced pressure. The residue was combined with acetonitrile (660 ml) and stirred at room temperature for 1 hour and the resultant insolubles were filtered off. The insolubles were washed with acetonitrile (50 ml) and the filtrate and the washing were combined and concentrated under reduced pressure, and the resultant residue was dissolved in acetonitrile (500 ml) and stirred at room temperature for 2 hours. The resultant insolubles were filtered off, and the filtrate was concentrated under reduced pressure. The residue was combined with diisopropyl ether (1000 ml) and the powder which precipitated was isolated by filtration to obtain ethyl 2-sulfo-1-cyclohexene-1-carboxylate as a white powder (55 g) containing inorganic substances. This was treated dropwise with thionyl chloride (150 ml) at 0° C. over 1 hour and then stirred at 80 to 85° C. for 20 hours. The mixture was evaporated under reduced pressure to dryness and the residue was partitioned between ethyl acetate (300 ml) and a dilute brine (400 ml) and the aqueous layer was extracted with ethyl acetate (200 ml). The ethyl acetate layers were combined and washed with saturated brine (200 mL) and dried over anhydrous sodium sulfate. The solvent was evaporated off to obtain a residue, which was purified by flash chromatography on silica gel column (eluent: ethyl acetate/hexane=1/8→ethyl acetate/hexane=1/5) to yield ethyl 2-chlorosulfonyl-1-cyclohexene-1-carboxylate (21.5 g) as yellow crystals.

$^1$H-NMR (CDCl$_3$) δ: 1.38 (3H, t, J=7.0 Hz), 1.70–1.89 (4H, m), 2.52–2.67 (4H, m), 4.30 (2H, q, J=7.0 Hz).

% Calculated for $C_9H_3ClO_4S$: C, 42.77; H,5.18;

% Found: C, 42.73; H,5.15.

Melting point 31.5 to 32.5 ° C.

Reference Example 3

Sodium peroxyborate tetrahydrate (10.6 g) was admixed with acetic acid (57 ml) and heated to 50 to 55° C. and then a solution of ethyl 2-mercapto-1-cyclopentene-1-carboxylate (3.9 g, synthesized in accordance with Tetrahedron, Vol.30, p.3753 (1974)) in acetic acid (7 ml) was added dropwise over 2 hours. The mixture was stirred at 50 to 55° C. for 3 hours and then at 80 to 85° C. for 5 hours and concentrated under reduced pressure. The residue was combined with acetonitrile (100 ml) and stirred at room temperature for 12 hours and the resultant insolubles were filtered off. The insolubles were washed with acetonitrile (10 ml) and the filtrate and the washing were combined and concentrated under reduced pressure, and the resultant residue was dissolved in acetonitrile (70 ml) and stirred at room temperature for 2 hours. The resultant insolubles were filtered off, and the filtrate was concentrated under reduced pressure. The residue was combined with diisopropyl ether (20 ml) and the pellet which precipitated was isolated by a filtration to obtain ethyl 2-sulfo-1-cyclopentene-1-carboxylate as a white powder (7.8 g) containing inorganic substances. This (1.0 g) was dissolved in thionyl chloride (3 ml) and then stirred at 80 to 90° C. for 15 hours. The mixture was evaporated under reduced pressure to dryness and the residue was dissolved in ethyl acetate (50 ml). The resultant aqueous solution was washed successively with water (50 ml) and saturated brine (50 ml) and then dried over anhydrous sodium sulfate. The solvent was evaporated off to obtain a residue, which was purified by flash chromatography on silica gel column (eluent: ethyl acetate/hexane=1/5) to yield ethyl 2-chlorosulfonyl-1-cyclopentene-1-carboxylate (153.7 mg) as a yellow oil.

$^1$H-NMR (CDCl$_3$) δ: 1.35 (3H, t, J=7.0 Hz), 2.18 (2H, quintet, J=8.0 Hz), 2.92–3.08 (4H, m), 4.33 (2H, q, J=7.0 Hz).

Reference Example 4

Sodium peroxyborate tetrahydrate (6.8 g) was admixed with acetic acid (37 ml) and heated to 50 to 55° C. and then a solution of ethyl 2-mercapto-1-cycloheptene-1-carboxylate (3.0 g, synthesized in accordance with Tetrahedron, Vol.30, p.3753 (1974)) in acetic acid (15 ml) was added dropwise over 1 hour. The mixture was stirred at 50 to 55° C. for 3 hours and then at 80 to 85° C. for 5 hours and concentrated under reduced pressure. The residue was combined with acetonitrile (100 ml) and stirred at room temperature for 3 hours and the resultant insolubles were filtered off. The insolubles were washed with acetonitrile (10 ml) and the filtrate and the washing were combined and concentrated under reduced pressure, and the resultant residue was dissolved in acetonitrile (70 ml) and stirred at room temperature for 1 hour. The resultant insolubles were filtered off, and the filtrate was concentrated under reduced pressure. The residue was combined with diisopropyl ether (100 ml) and the pellet which precipitated was isolated by a filtration to obtain ethyl 2-sulfo-1-cycloheptene-1-carboxylate as a white powder (3.4 g) containing inorganic substances. This (1.5 g) was dissolved in thionyl chloride (4 ml) and then stirred at 80 to 90° C. for 15 hours. The mixture was evaporated under reduced pressure to dryness and the residue was dissolved in ethyl acetate (30 ml). The solution obtained was washed with saturated brine (30 ml×2) and then dried over anhydrous sodium sulfate. The solvent was evaporated off to obtain a residue, which was purified by flash chromatography on silica gel column (eluent: ethyl acetate/hexane=1/8) to yield ethyl 2-chlorosulfonyl-1-cycloheptene-1-carboxylate (590 mg) as a brown oil.

$^1$H-NMR (CDCl$_3$) δ: 1.34 (3H, t, J=7.4 Hz), 1.60–2.00 (6H, m), 2.40–2.90 (4H, m), 4.29 (2H, q, J=7.4 Hz).

Reference Example 5

A solution of ethyl 6-[N-(4-chloro-2-fluorophenyl)sulfamoyl]-1-cyclohexene-1-carboxylate obtained in Example 1 (Compound 1, 210 mg) in acetonitrile (29 ml) was admixed with a 1N aqueous solution of sodium hydroxide (29 ml) and the mixture was stirred at 55° C. for 12 hours. The mixture was concentrated under reduced pressure and the residue was purified by CHP-20P column chromatography (eluent: water→methanol/water=1/1). The effluent was concentrated under reduced pressure and the residue was dissolved in water (5 ml) and lyophilized to yield sodium 6-[N-(4-chloro-2-fluorophenyl)sulfamoyl]-1-cyclohexene-1-carboxylate (43 mg) as a white powder.

$^1$H-NMR (D$_2$O) δ: 1.65–2.40 (6H, m), 4.55 (1H, d, J=3.0 Hz), 6.86 (1H, t, J=3.4 Hz), 7.19–7.33 (2H, m), 7.50 (1H, t, J=9.0 Hz).

% Calculated for C$_{13}$H$_{12}$ClFNO$_4$SNa.H$_2$O : C, 41.78; H, 3.78; N, 3.75

% Found: C, 41.52; H, 3.55; N, 3.84.

SIMS: 356 (MH$^+$)

Reference Example 6

2,4-Difluoronitrobenzene (8.0 g) was dissolved in N,N-dimethylformamide (110 ml) and the solution was admixed with 1H-1,2,4-triazole (3.47 g) and potassium carbonate (6.95 g) and the mixture was stirred under a nitrogen atmosphere at 70° C. for 20 hours. The reaction mixture was diluted with ethyl acetate and washed with water. The aqueous layer was extracted with ethyl acetate, and the ethyl acetate layers were combined and washed 5 times with water and then with saturated brine, and then dried over magnesium sulfate. The solvent was distilled off under reduced pressure, and the residue was purified by column chromatography on silica gel (ethyl acetate/hexane=1:1.3). A desired fraction was concentrated under reduced pressure and the residue was crystallized from a mixture of ethyl acetate and diisopropyl ether to yield 1-(3-fluoro-4-nitrophenyl)-1H-1,2,4-triazole (5.29 g) as yellow powdery crystals.

$^1$H-NMR (CDCl$_3$) δ: 7.32–7.42 (2H, m), 8.13 (1H, dd, J=9.8 Hz, 5.0 Hz), 8.15 (1H, s), 8.43 (1H, s).

% Calculated for C$_8$H$_5$FN$_4$O$_2$: C, 46.16; H, 2.42; N, 26.92

% Found: C, 45.98; H, 2.43; N, 26.85.

Melting point: 90 to 91° C.

Reference Example 7

1-(3-Fluoro-4-nitrophenyl)-1H-1,2,4-triazole (3.06 g) was dissolved in ethanol (100 ml) and admixed with 10% Pd/C (50% water, 612 mg) and then stirred under a hydrogen atmosphere at room temperature for 1 hour. After filtering the catalyst off, the filtrate was concentrated under reduced pressure. The residue was diluted with ethyl acetate, and the resultant solution as washed successively with water and saturated brine, and dried over magnesium sulfate. The solvent was distilled off under reduced pressure, and the residue was purified by column chromatography on silica gel (ethyl acetate/hexane=1:2). A desired fraction was concentrated under reduced pressure and the residue was crystallized from a mixture of ethyl acetate and diisopropyl ether to yield 1-(4-amino-3-fluorophenyl)-1H-1,2,4-triazole (1.68 g) as yellow powdery crystals.

$^1$H-NMR (CDCl$_3$) δ: 4.41 (2H, br), 6.78–6.85 (1H, m), 6.96–7.05 (2H, m), 8.16 (1H, s), 8.37 (1H, s).

% Calculated for C$_8$H$_7$FN$_4$: C, 53.93; H, 3.96; N, 31.45

% Found: C, 54.07; H, 3.82; N, 31.55.

Melting point: 103 to 104° C.

Reference Example 8

Methyl 4-amino-3-chlorobenzoate (5.65 g; synthesized in accordance with Synthesis, 1985, 669) was dissolved in tetrahydrofuran (112 ml) and admixed with a solution of sodium hydrogen carbonate (7.67 g) in water (84.8 ml) and benzyl chloroformate (39.1 ml) and the mixture was stirred under a nitrogen atmosphere at room temperature for 22.5 hours. The reaction mixture was extracted with ethyl acetate and the ethyl acetate layer was washed three times with water and then twice with saturated brine. The ethyl acetate layer was dried over magnesium sulfate and then the solvent was distilled off under reduced pressure, and then the residue was purified by column chromatography on silica gel (ethyl acetate/hexane=1:7). A desired fraction was concentrated under reduced pressure and the residue was crystallized from a mixture of ethyl acetate and diisopropyl ether to yield methyl 4-benzyloxycarbonylamino-3-chlorobenzoate (7.51 g) as white crystals.

$^1$H-NMR (CDCl$_3$) δ: 3.91 (3H, s), 5.25 (2H, s), 7.38–7.44 (6H, m), 7.95 (1H, dd, J=8.8 Hz, 2.0 Hz), 8.06 (1H, d, J=2.0 Hz), 8.33 (1H, d, J=8.8 Hz).

% Calculated for C$_{16}$H$_{14}$ClNO$_4$: C, 60.10; H. 4.41; N, 4.38

% Found: C, 60.21; H, 4.42; N, 4.22.

Melting point: 107.5 to 108.5° C.

Reference Example 9

Potassium t-butoxide (24.7 g) was dissolved in dimethylsulfoxide (221 ml) and admixed with methyl 4-benzyloxycarbonylamino-3-chlorobenzoate (4.52 g) and the mixture was stirred at room temperature for 25 minutes. The reaction mixture was poured into water (200 ml), which was then acidified with 1N hydrochloric acid (225 ml) and then extracted with ethyl acetate. The ethyl acetate layer was washed successively with water and saturated brine, and dried over magnesium sulfate. The solvent was distilled off under reduced pressure, and the residue was purified by column chromatography on silica gel (ethyl acetate/hexane=2:5). A desired fraction was concentrated under reduced pressure to obtain 4-benzyloxycarbonylamino-3-chlorobenzoic acid (2.47 g) as a white powder.

$^1$H-NMR (d$_6$-DMSO) δ: 3.34 (1H, br), 5.20 (2H, s), 7.34–7.47 (5H, m), 7.86 (1H, s), 7.87 (1H, s), 7.93 (1H, s), 9.40 (1H, s).

% Calculated for C$_{15}$H$_{12}$ClNO$_4$: C, 58.93; H, 3.96; N, 4.58

% Found: C, 58.85; H, 3.93; N, 4.55.

Melting point: 181.5 to 182.5° C.

Reference Example 10

4-Benzyloxycarbonylamino-3-chlorobenzoic acid (0.80 g) was dissolved in N,N-dimethylformamide (24.0 ml) and admixed at room temperature with t-butyl glycinate (0.44 g) and triethylamine (0.77 ml). Diethyl cyanophosphate (0.43 ml) was added with ice-cooling, and the mixture was stirred under a nitrogen atmosphere at room temperature for 30 minutes. The reaction mixture was diluted with ethyl acetate and washed with water. The ethyl acetate layer was separated and the aqueous layer was extracted with ethyl acetate. The ethyl acetate layers were combined and washed three times with water and then twice with saturated brine, and then dried over magnesium sulfate. The solvent was distilled off under reduced pressure, and the residue was crystallized from a mixture of ethyl acetate and diisopropyl ether to yield t-butyl N-(4-benzyloxycarbonylamino-3-chlorobenzoyl) glycinate (0.93 g) as white crystals.

$^1$H-NMR (CDCl$_3$) δ: 1.51 (9H, s), 4.12 (2H, d, J=5.0 Hz), 5.24 (2H, s), 6.58 (1H, t, J=5.0 Hz), 7.37–7.45 (6H, m), 7.68 (1H, dd, J=8.6 Hz, 2.0 Hz), 7.89 (1H, d, J=2.0 Hz), 8.32 (1H, d, J=8.6 Hz).

% Calculated for C$_{21}$H$_{23}$ClN$_2$O$_5$: C, 60.22; H, 5.53; N, 6.69

% Found: C, 60.27; H, 5.50; N, 6.69.

Melting point: 163 to 164° C.

Reference Example 11 t-Butyl N-(4-benzyloxycarbonylamino-3-chlorobenzoyl) glycinate (0.80 g) was dissolved in tetrahydrofuran (30 ml) and then admixed with 10% Pd/C (50% water, 160 mg) and then stirred under a hydrogen atmosphere at room temperature for 1.5 hours. The catalyst was filtered off and the filtrate was diluted with ethyl acetate and washed three times with water and twice with saturated brine. The ethyl acetate layer was dried over magnesium sulfate and the solvent was distilled off under reduced pressure. The residue was purified by column chromatography on silica gel (ethyl acetate/hexane=1:1). A desired fraction was concentrated under reduced pressure and the residue was crystallized from a mixture of diisopropyl ether and hexane to yield t-butyl N-(4-amino-3-chlorobenzoyl)glycinate (0.49 g) as white crystals.

$^1$H-NMR (CDCl$_3$) δ: 1.50 (9H, s), 4.11 (2H, d, J=5.0 Hz), 4.38 (2H, s), 6.47 (1H, m), 6.75 (1H, d, J=8.4 Hz), 7.54 (1H, dd, J=8.4 Hz, 2.0 Hz), 7.77 (1H, d, J=2.0 Hz).

% Calculated for C$_{13}$H$_{17}$ClN$_2$O$_3$: C, 54.84; H, 6.02; N, 9.84.

% Found: C, 54.56; H, 5.85; N, 9.54.

Melting point: 116 to 117° C.

Reference Example 12

A solution of ethyl 6-[N-(2, 4-difluorophenyl)sulfamoyl]-1-cyclohexene-1-carboxylate obtained in Example 3 (Compound 3, 2.5 g) in acetonitrile (288 ml) was admixed with a 1N aqueous solution of sodium hydroxide (228 ml) and the mixture was stirred at 55° C. for 12 hours. The mixture was concentrated under reduced pressure and the residue was purified by CHP-20P column chromatography (eluent: water→methanol/water=1/1). The eluent was concentrated under reduced pressure and the residue was dissolved in water (10 ml) and lyophilized to yield sodium 6-[N-(2,4-difluorophenyl)sulfamoyl]-1-cyclohexene-1-carboxylate (0.50 g) as white crystals.

$^1$H-NMR (d$_6$-DMSO) δ: 1.50–1.65 (2H, m), 1.78–2.41 (4H, m), 4.13 (1H, d, J=4 Hz), 6.88–6.98 (2H, m), 7.09–7.20 (1H, m), 7.42 (1H, dt, J=9.0 Hz, 6.2 Hz).

% Calculated for C$_{13}$H$_{12}$F$_2$NO$_4$SNa.H$_2$O: C, 43.70; H, 3.95; N, 3.92

% Found: C, 44.17; H, 3.86; N, 3.57.

SIMS: 340 (MH$^+$)

Sodium 6-[N-(2,4difluorophenyl)sulfamoyl]-1-cyclohexene-1-carboxylate (0.48 g) was dissolved in water (100 ml) and adjusted at pH 1 to 2 with 1N HCl and then extracted with ethyl acetate (100 ml). The ethyl acetate layer was washed with water (100 ml×2) and dried over anhydrous magnesium sulfate and then the solvent was distilled off under reduced pressure. The residue was crystallized from diisopropyl ether to obtain 6-[N-(2,4-difluorophenyl) sulfamoyl]-1-cyclohexene-1-carboxylic acid (0.44 g) as white powdery crystals.

$^1$H-NMR (d$_6$-DMSO) δ: 1.56–1.78 (2H, m), 2.00–2.41 (4H, m), 4.31 (1H, d, J=4.2 Hz), 7.08 (2H, br), 7.26–7.37 (1H, m), 7.44–7.56 (1H, m), 9.80 (1H, br), 12.38 (1H, br).

% Calculated for C$_{13}$H$_{13}$F$_2$NO$_4$S: C, 49.21; H, 4.13; N, 4.41

% Found: C, 49.47; H. 4.16; N, 4.62.

SIMS: 317 (M$^+$)

Reference Example 13

Ethyl 2-oxo-5-phenylcyclohexane carboxylate (57.5 g) (synthesized in accordance with Chemical & Pharmaceutical Bulletin, Vol.20, p.277 (1972)) was subjected to a procedure described in Tetrahedron, Vol.30, p.3753 (1974) to yield ethyl 2-mercapto-5-phenyl-1-cyclohexene-1-carboxylate (29.3 g) as pale yellow powdery crystals.

$^1$H-NMR (CDCl$_3$) δ: 1.27 (3H, t, J=7.2 Hz), 1.76–2.05 (2H, m), 2.28–2.91 (5H, m), 4.10 (1H, s), 4.21 (2H, q, J=7.2 Hz), 7.19–7.38 (5H, m).

% Calculated for C$_{15}$H$_{18}$O$_2$S: C, 68.67; H, 6.92

% Found: C, 68.86; H, 6.82.

Reference Example 14

Sodium peroxyborate tetrahydrate (35.2 g) was admixed with acetic acid (200 ml) and heated to 50 to 55° C. and then a solution of ethyl 2-mercapto-5-phenyl-1-cyclohexene-1-carboxylate synthesized in Reference Example 13 (20 g) in acetic acid (200 ml) was added dropwise over 2 hours. The mixture was stirred at 50 to 55° C. for 3 hours and then at 80 to 85° C. for 5 hours and concentrated under reduced pressure. The residue was combined with acetonitrile (500 ml) and stirred at room temperature for 1 hour and the resultant insolubles were filtered off. The insolubles were washed with acetonitrile (20 ml) and the filtrate and the washing were combined and concentrated under reduced pressure, and the resultant residue was dissolved in a mixture of acetonitrile (500 ml) and methanol (500 ml) and stirred at room temperature for 2 hours. The resultant insolubles were filtered off, and the filtrate was concentrated under reduced pressure. The residue was combined with diisopropyl ether (500 ml) and the pellet which precipitated was isolated by a filtration to obtain ethyl 5-phenyl-2-sulfo-1-cyclohexene-1-carboxylate as a white powder (40.4 g) containing inorganic substances.

This (10 g) was treated dropwise with thionyl chloride (30 ml) at 0° C. over 1 hour and then stirred at 85 to 90° C. for 7 hours. The solution was evaporated under reduced pressure to dryness and the residue was dissolved in ethyl acetate (50 ml). The solution obtained was washed successively with water (50 ml) and saturated brine (50 ml) and then dried over anhydrous sodium sulfate. The solvent was evaporated off to obtain a residue, which was purified by flash chromatography on silica gel column (eluent: ethyl acetate/hexane=1/8) to yield ethyl 2-chlorosulfonyl-5-phenyl-1-cyclohexene-1-carboxylate (4.8 g) as pale yellow crystals.

$^1$ H-NMR (CDCl$_3$) δ: 1.35 (3H, t, J=7.4 Hz), 1.85–2.02 (1H, m), 2.14–2.26 (1H, m), 2.56–3.02 (5H, m), 4.31 (2H, q, J=7.4 Hz), 7.19–7.40 (5H, m).

Reference Example 15

Ethyl 5-t-butyl-2-oxocyclohexene carboxylate (50.7 g) [synthesized in accordance with Collect. Czech. Chem. Commun., 1976, 41, 2928] was subjected to a procedure described in Tetrahedron, Vol.30, p.3753 (1974) to yield ethyl 5-t-butyl-2-mercapto-1-cyclohexene-1-carboxylate (39.6 g) as yellow oil.

$^1$H-NMR (CDCl$_3$) δ: 0.90 (9H, s), 1.22–1.34 (1H, m), 1.32 (3H, t, J=7.2 Hz), 1.75–2.03 (3H, m), 2.40–2.67 (3H, m), 3.91 (1H, s), 4.24 (2H, q, J=7.2 Hz).

% Calculated for C$_{13}$H$_{22}$O$_2$S: C, 64.42; H, 9.15

Found: C, 64.47; H, 9.29.

Reference Example 16

Sodium peroxyborate tetrahydrate (38.2 g) was admixed with acetic acid (270 ml) and heated to 50 to 55° C. and then a solution of ethyl 5-t-butyl-2-mercapto-1-cyclohexene-1-carboxylate (20.1 g) synthesized in Reference Example 15 in acetic acid (31 ml) was added dropwise over 2 hours. The mixture was stirred at 50 to 55° C. for 3 hours and then at 80 to 85° C. for 7.5 hours and concentrated under reduced pressure. The residue was combined with acetonitrile (445ml) and stirred at room temperature for 3.5 hours and the resultant insolubles were filtered off. The insolubles were washed with acetonitrile (110 ml) and the filtrate and the washing were combined and concentrated under reduced pressure, and the resultant residue was dissolved in acetonitrile (320 ml) and stirred at room temperature for 15 hours. The resultant insolubles were filtered off, and the filtrate was concentrated under reduced pressure. The residue was combined with diisopropyl ether (250 ml) and the pellet which precipitated was isolated by a filtration and concentrated under reduced pressure to obtain ethyl 5-t-butyl-2-sulfo-1-cyclohexene-1-carboxylate as yellow oil (17.6 g) containing inorganic substances. This (16.4 g) was treated dropwise with thionyl chloride (49.2 ml) at 0° C. over 0.5 hours and then stirred at 80 to 90° C. for 7 hours. The solution was evaporated under reduced pressure to dryness and the residue was partitioned between ethyl acetate (200 ml) and dilute brine (240 ml) and the aqueous layer was extracted with ethyl acetate (100 ml). The combined ethyl acetate layers were washed with saturated brine (120 ml) and then dried over anhydrous sodium sulfate. The solvent was evaporated off to obtain a residue, which was purified by column chromatography on silica gel (eluent: ethyl acetate/hexane=1/10), and a desired fraction was concentrated under reduced pressure. The residue was crystallized from hexane to yield ethyl 5-t-butyl-2-chlorosulfonyl-1-cyclohexene-1-carboxylate (7.4 g) as a white crystals.

$^1$H-NMR (CDCl$_3$) δ: 0.92 (9H, s), 1.22–1.46 (2H, m), 1.36 (3H, t, J=7.2 Hz), 2.04–2.35 (2H, m), 2.45–2.65 (2H, m), 2.79–2.92 (1H, m), 4.31 (2H, q, J=7.2 Hz).

% Calculated for C$_{13}$H$_{21}$ClO$_4$S: C, 50.56; H, 6.85

Found: C, 50.47; H, 6.74.

Reference Example 17

Ethyl 5,5-dimethyl-2-oxocyclohexene carboxylate (31.2 g) [synthesized in accordance with J. Org. Chem., 1953, 18, 661] was subjected to a procedure described in Tetrahedron, Vol.30, p.3753 (1974) to yield ethyl 5,5-dimethyl-2-mercapto-1-cyclohexene-1-carboxylate (29.9 g) as yellow oil.

$^1$H-NMR (CDCl$_3$) δ: 0.95 (6H, s), 1.31 (3H, t, J=7.0 Hz), 1.43 (2H, t, J=6.4 Hz), 2.14 (2H, t, J=2.0 Hz), 2.45–2.55 (2H, m), 3.88 (1H, s), 4.22 (2H, q, J=7.0 Hz).

% Calculated for C$_{11}$H$_{18}$O$_2$S: C, 61.64; H, 8.47

Found: C, 61.40; H, 8.68.

Reference Example 18

Sodium peroxyborate tetrahydrate (46.3 g) was admixed with acetic acid (270 ml) and heated to 50 to 55° C. and then a solution of ethyl 5,5-dimethyl-2-mercapto-1-cyclohexene-1-carboxylate (20.2 g) synthesized in Reference Example 17 in acetic acid (30 ml) was, added dropwise over 2 hours. The mixture was stirred at 50 to 55° C. for 3 hours and then at 80 to 85° C. for 8 hours and concentrated under reduced pressure. The residue was combined with acetonitrile (450 ml) and stirred at room temperature for 4 hours and the resultant insolubles were filtered off. The insolubles were washed with acetonitrile (120 ml) and the filtrate and the washing were combined and concentrated under reduced pressure, and the resultant residue was dissolved in acetonitrile (330 ml) and stirred at room temperature for 15 hours. The resultant insolubles were filtered off, and the filtrate was concentrated under reduced pressure. The residue was combined with diisopropyl ether (300 ml) and the powder which precipitated was isolated by a filtration to yield ethyl 5,5- dimethyl-2-sulfo-1-cyclohexene-1-carboxylate as an orange oil (26.5 g) containing inorganic substances. This (26.3 g) was dissolved in thionyl chloride (79 ml) and then stirred at 80 to 90° C. for 7.5 hours. The solution was evaporated under reduced pressure to dryness and the residue was dissolved in ethyl acetate (150 ml). The solution thus obtained was combined with dilute brine (200 ml) and partitioned, and then the ethyl acetate layer was washed twice with saturated brine (100 ml) and then dried over anhydrous sodium sulfate. The solvent was evaporated off to obtain a residue, which was purified by column chromatography on silica gel (eluent: ethyl acetate/hexane=1/8) to yield ethyl 2-chlorosulfonyl-5, 5-dimethyl-1-cyclohexene-1-carboxylate (12.4 g) as a brown oil.

$^1$H-NMR (CDCl$_3$) δ: 1.02 (6H, s), 1.34 (3H, t, J=7.2 Hz), 1.61 (2H, t, J=6.6 Hz), 2.31 (2H, t, J=2.4 Hz), 2.64–2.72 (2H, m), 4.30 (2H, q, J=7.2 Hz).

% Calculated for $C_{11}H_{17}ClO_4S$: C, 47.06; H, 6.10

% Found: C, 47.46; H, 6.10.

Example 1

Ethyl 2-sulfo-1-cyclohexene-1-carboxylate (7.11 g) obtained in Reference Example 1 was dissolved in thionyl chloride (21.0 ml) and heated under reflux for 14 hours and then the reaction mixture was evaporated under reduced pressure to dryness. The residue was subjected three times to the procedure involving an addition of hexane (30 ml) followed by an evaporation under reduced pressure to dryness to yield ethyl 2-chlorosulfonyl-1-cyclohexene-1-carboxylate. This was combined with ethyl acetate (20 ml) and the resultant mixture was added to a mixture consisting of 4-chloro-2-fluoroaniline (3.64 g), triethylamine (3.41 ml) and ethyl acetate (54 ml), and then stirred at room temperature for 18 hours. The reaction mixture was partitioned between ethyl acetate (50 ml) and water (200 ml). The ethyl acetate layer was washed with dilute brine (100 ml×3) and dried over anhydrous magnesium sulfate, and then the solvent was distilled off. The residue was combined with diisopropyl ether (8 ml) and the crystals which precipitated was isolated by filtration. The crystals thus obtained were washed with ethyl acetate (8 ml) to yield ethyl 6-[N-(4-chloro-2-fluorophenyl)sulfamoyl]-1-cyclohexene-1-carboxylate (Compound 1; 1.60 g) as colorless needle-like crystals. The mother liquor and the wash were combined and subjected to silica gel chromatography (eluent: ethyl acetate/hexane=1/5→1/4) and the effluent was concentrated under reduced pressure, and the residue was crystallized from ethyl acetate—diisopropyl ether to yield the second crop of Compound 1 (1.41 g).

$^1$H-NMR (DMSO-d$_6$) δ: 1.10 (3H, t, J=7.2 Hz), 1.57–1.82 (2H, m), 1.98–2.44 (4H, m), 4.02 (2H, q, J=7.2 Hz), 4.32 (1H, d, J=4.4Hz), 7.12 (1H, t, J=3.4 Hz), 7.23–7.31 (1H, m), 7.45–7.54 (2H, m), 10.04 (1H, s).

% Calculated for $C_{15}H_{17}ClFNO_4S$: C, 49.79; H, 4.74; N, 3.87.

% Found C, 49.93; H, 4.72; N, 4.09.

Example 2

To a solution of ethyl 6-[N-(4-chloro-2-fluorophenyl) sulfamoyl]-1-cyclohexene-1-carboxylate (Compound 1; 250 mg) obtained in Example 1 was 1.60 g) in N,N-dimethylformamide (2.5 ml), methyl iodide (118 mg), potassium carbonate (191 mg) were added and the mixture was stirred at room temperature for 1 hour. The reaction mixture was diluted with ethyl acetate (30 ml), washed with water (30 ml×2) and dried over anhydrous magnesium sulfate, and then the solvent was distilled off. The residue was purified by silica gel chromatography (eluent: ethyl acetate/hexane= 1/4) to yield ethyl 6-[N-(4-chloro-2-fluorophenyl)-N-methylsulfamoyl]-1-cyclohexene-1-carboxylate (Compound 2; 250 mg) as a colorless oil.

$^1$H-NMR (DMSO-d$_6$) δ: 1.17 (3H, t, J=7.2 Hz), 1.56–2.44 (6H, m), 3.19 (3H, s), 4.12 (2H, q, J=7.2 Hz), 4.64 (1H, d, J=4.4 Hz), 7.16 (1H, t, J=3.6 Hz), 7.33–7.39 (1H, m), 7.54–7.62 (2H, m).

% Calculated for $C_{16}H_{19}ClFNO_4S$: C, 51.13; H, 5.10; N, 3.73

% Found: C, 50.91; H, 5.10; N, 3.64.

Example 3

Ethyl 2-sulfo-1-cyclohexene-1-carboxylate (2.0 g) obtained in Reference Example 1 was dissolved in thionyl chloride (5.9 ml) and heated under reflux for 14 hours and then the reaction mixture was evaporated under reduced pressure to dryness. The residue was subjected three times to the procedure involving an addition of hexane (10 ml) followed by an evaporation under reduced pressure to dryness to yield ethyl 2-chlorosulfonyl-1-cyclohexene-1-carboxylate. This was combined with ethyl acetate (15 ml) and the resultant mixture was added to a mixture consisting of 2,4-difluoroaniline (1.29 g), triethylamine (2.0 ml) and ethyl acetate (10 ml) with ice-cooling, and then stirred with ice-cooling for 30 minutes and then at room temperature for 20 hours. The reaction mixture was diluted with ethyl acetate (100 ml) and washed with dilute brine (150 ml×3) and dried over anhydrous magnesium sulfate, and then the solvent was distilled off. The residue was combined with diisopropyl ether (6 ml) and the crystals which precipitated were isolated by a filtration to yield ethyl 6-[N-(2,4-difluorophenyl)sulfamoyl]-1-cyclohexene-1-carboxylate (Compound 3; 0.61 g) as colorless needle-like crystals.

$^1$H-NMR (DMSO-d$_6$) δ: 1.07 (3H, t, J=7.2 Hz), 1.46–1.82 (2H, m), 1.97–2.50 (4H, m), 4.01 (2H, q, J=7.2 Hz), 4.28 (1H, d, J=4.8 Hz), 7.04–7.15 (2H, m), 7.29–7.54 (2H, m), 9.86 (1H, brs).

% Calculated for $C_{15}H_{17}F_2NO_4S$: C, 52.17; H, 4.96; N, 4.06

% Found.: C, 52.27; H, 4.84; N, 3.98

Example 4

Ethyl 2-sulfo-1-cyclohexene-1-carboxylate (0.67 g) obtained in Reference Example 1 was dissolved in thionyl chloride (2.0 ml) and heated under reflux for 8 hours and then the reaction mixture was evaporated under reduced pressure to dryness. The procedure involving an addition of hexane (8 ml) followed by an evaporation under reduced pressure to dryness was repeated three times to yield ethyl 2-chlorosulfonyl-1-cyclohexene-1-carboxylate. This was combined with ethyl acetate (5 ml) and the resultant mixture was added to a mixture consisting of 2,6-diisopropylaniline (0.89 g), triethylamine (0.70 ml) and ethyl acetate (8 ml) with ice-cooling, and then stirred with ice-cooling for 30 minutes and then at room temperature for 20 hours. The reaction mixture was diluted with ethyl acetate (20 ml) and washed with water (40 ml) and dilute brine (40 ml×3) and dried over anhydrous magnesium sulfate, and then the solvent was distilled off. The residue was purified by silica gel chromatography (eluent: ethyl acetate/hexane=1/20→1/9) to yield ethyl 6-[N-(2,6-diisopropylphenyl)sulfamoyl]-1-cyclohexene-1-carboxylate (Compound 4; 0.12 g) as a colorless oil.

$^1$H-NMR (DMSO-d$_6$) δ: 0.99 (3H, t, J=7.2 Hz), 1.15 (12H, d, J=6.6 Hz), 1.58–2.60 (6H, m), 3.39–3.52 (2H, m), 3.97 (2H, q, J=7.2 Hz), 4.38 (1H, d, J=5.4 Hz), 7.05 (1H, br), 7.15–7.31 (3H, m), 8.96 (1H, s).

Example 5

Ethyl 2-sulfo-1-cyclohexene-1-carboxylate (1.0 g) obtained in Reference Example 1 was dissolved in thionyl chloride (3.0 ml) and heated under reflux for 8 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (10 ml) and the resultant mixture was added to a mixture consisting of 4-nitroaniline (0.69 g), triethylamine (0.70 ml) and ethyl acetate (8 ml) with ice-cooling, and then stirred with ice-cooling for 30 minutes and then at room temperature for 14 hours. The reaction mixture was diluted with ethyl acetate (60 ml) and washed with a dilute brine (50 ml×3) and dried over anhydrous magnesium sulfate, and then the solvent was distilled off. The residue was purified by silica gel chromatography (eluent: ethyl acetate/hexane=1/2) and then crystallized from diisopropyl ether to yield ethyl 6-[N-(4-nitrophenyl) sulfamoyl]-1-cyclohexene-1-carboxylate (Compound 5; 90 mg) as pale yellow powdery crystals.

$^1$H-NMR (DMSO-d$_6$) δ: 1.13 (3H, t, J=7 Hz), 1.60–1.85 (2H, m), 1.96–2.46 (4H, m), 3.90–4.16 (2H, m), 4.46 (1H, d, J=5 Hz), 7.21 (1H, t, J=3 Hz), 7. 38 (2H, d, J=9 Hz), 8.22 (2H, d, J=9Hz), 10.92 (1H, s).

% Calculated for C$_{15}$H$_{18}$N$_2$O$_6$S: C, 50.84; H, 5.12; N, 7.90

% Found: C, 50.80; H, 4.99; N, 7.93

Example 6

Ethyl 2-sulfo-1-cyclohexene-1-carboxylate (0.67 g) obtained in Reference Example 1 was dissolved in thionyl chloride (2.0 ml) and heated under reflux for 8 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (12 ml) and the resultant mixture was added to a mixture consisting of aniline (0.28 g), triethylamine (0.42 ml) and ethyl acetate (4 ml) with ice-cooling, and then stirred with ice-cooling for 30 minutes and then at room temperature for 13 hours. The reaction mixture was diluted with ethyl acetate (50 ml) and washed with water (50 ml) and 0.2 N HCl (50 ml) and water (50 ml×2) and dried over anhydrous magnesium sulfate, and then the solvent was distilled off. The residue was purified by silica gel chromatography (eluent: ethyl acetate/hexane= 1/4), and the first effluent was concentrated under reduced pressure and the residue was purified by chromatography on octadecyl (ODS) column (eluent: methanol/water=7/3). The effluent was concentrated under reduced pressure to precipitate crystals which were collected by filtration to yield ethyl 2-(N-phenylsulfamoyl)-1-cyclohexene-1-carboxylate (Compound 7; 37 mg) as colorless powdery crystals. The second effluent was also concentrated under reduced pressure and the resultant residue was purified by an ODS column chromatoghraphy (eluent: methanol/water=7/3). The effluent was concentrated under reduced pressure and the residue was crystallized from methanol—water to yield ethyl 6-(N-phenylsulfamoyl)-1-cyclohexene-1-carboxylate (Compound 6; 56 mg) as colorless needle-like crystals.

Compound 6: $^1$H-NMR (DMSO-d$_6$) δ: 1.14 (3H, t, J=7.2 Hz), 1.55–1.74 (2H, m), 1.98–2.42 (4H, m), 3.97–4.12 (2H, m), 4.32 (1H, d, J=4.8 Hz), 7.02–7.35 (6H, m), 10.03 (1H, brs).

% Calculated for C$_{15}$H$_{19}$NO$_4$S: C, 58.23; H, 6.19; N, 4.53

% Found: C, 58.28; H, 6.19; N, 4.55

Compound 7: $^1$H-NMR (DMSO-d$_6$) δ: 1.23 (3H, t, J=7 Hz), 1.54 (4H, br), 2.25 (4H, br), 4.14 (2H, q, J=7 Hz), 7.02–7.32 (5H, m), 10.13 (1H, brs).

% Calculated for C$_{15}$H$_{19}$NO$_4$S: C, 58.23; H, 6.19; N, 4.53

% Found: C, 57.94; H, 6.10; N, 4.52.

Example 7

Ethyl 2-sulfo-1-cyclohexene-1-carboxylate (2.0 g) obtained in Reference Example 1 was dissolved in thionyl chloride (5.0 ml) and heated under reflux for 14 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (30 ml) and washed with dilute brine (30 ml×2) and saturated brine (20 ml) and dried over anhydrous magnesium sulfate, and the solvent was distilled off under reduced pressure. The resultant oil was stirred together with a solution of 4-chloro-2-fluoroaniline (0.55 g) in N,N-dimethylformamide (5 ml) at room temperature for 18 hours. The reaction mixture was combined with ice-water (100 ml) and ethyl acetate (100 ml) and partitioned. The ethyl acetate layer was washed with water (80 ml×2) and dried over anhydrous magnesium sulfate and then the solvent was distilled off. The residue was purified by silica gel chromatography (eluent: ethyl acetate/hexane=1/4) and crystallized from diisopropyl ether to yield ethyl 2-[N-(4-chloro-2-fluorophenyl)sulfamoyl]-1-cyclohexene-1-carboxylate (Compound 9; 44 mg) as a colorless powdery crystals.

$^1$H-NMR (DMSO-d$_6$) δ1.06 (3H, t, J=7.2 Hz), 1.62 (4H, br), 2.25 2H, br), 2.39 (2H, 3.95 (2H, q, J=7.2 Hz), 7.23–7.37 (2H, m), 7.47–7.52 (1H, m), 10.11 (1H, s).

% Calculated for C$_{15}$H$_{17}$ClFNO$_4$S: C, 49.79; H, 4.74; N, 3.87

% Found: C, 49.84; H, 4.76; N, 3.92.

Example 8

Ethyl 2-sulfo-1-cyclohexene-1-carboxylate (0.67 g) obtained in Reference Example 1 was dissolved in thionyl chloride (2.0 ml) and heated under reflux for 8 hours and then the reaction mixture was evaporated under reduced pressure to dryness. The procedure involving an addition of hexane (8 ml) followed by an evaporation under reduced pressure to dryness was repeated three times to yield ethyl 2-chlorosulfonyl-1-cyclohexene-1-carboxylate. This was combined with ethyl acetate (10 ml) and the resultant mixture was added to a mixture consisting of 4-methoxyaniline (0.37 g), triethylamine (0.42 ml) and ethyl acetate (4 ml) with ice-cooling, and then stirred with ice-cooling for 30 minutes and then at room temperature for 13 hours. The reaction mixture was diluted with ethyl acetate (60 ml) and washed with dilute brine (80 ml), a 10% aqueous solution of phosphoric acid (50 ml) and dilute brine (50 ml×2) and dried over anhydrous magnesium sulfate, and then the solvent was distilled off. The residue was purified by silica gel chromatography (eluent: ethyl acetate/hexane =1/2) and the effluent was concentrated to dryness and the residue was crystallized from ethyl acetate—diisopropyl ether to yield 2-(4-methoxyphenyl)-4,5,6,7-tetrahydro-1,2-benzoisothiazole-3(2H)-one 1,1-dioxide (Compound 67, 40 mg) as colorless needle-like crystals. The mother liquor was concentrated and purified by ODS column chromatography (eluent: methanol/water=7/3) and then the effluent was concentrated under reduced pressure to yield ethyl 2-[N-(4-methoxyphenyl)sulfamoyl]-1-cyclohexene-1-carboxylate (Compound 8; 15 mg) as a colorless powder.

Compound 8: $^1$H-NMR (DMSO-$d_6$) δ: 1.18 (3H, t, J=7.0 Hz), 1.54, 1.56 (4H, br), 2.25 (4H, br), 3.72 (3H, s), 4.08 (2H, q, J=7.0 Hz), 6.86 (2H, d, J=8 Hz), 7.07 (2H, d, J=8 Hz), 9.79 (1H, brs). Compound 67: $^1$H-NMR (CDCl$_3$) δ: 1.70–1.88 (4H, m), 2.41–2.60 (4H, m), 3.82 (3H, s), 7.11 (2H, d, J=9.0 Hz), 7.31 (2H, d, J=9.0 Hz).

% Calculated for $C_{14}H_{15}NO_4S$: C, 57.32; H, 5.15; N, 4.77

% Found: C, 57.41; H, 5.01; N, 4.78.

Example 9

Ethyl 2-sulfo-1-cyclohexene-1-carboxylate (0.83 g) obtained in Reference Example 1 was dissolved in thionyl chloride (2.4 ml) and heated under reflux for 8 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (10 ml) and the resultant mixture was added to a mixture consisting of 2-fluoroaniline (0.40 g), triethylamine (0.50 ml) and ethyl acetate (5 ml) with ice-cooling, and then stirred with ice-cooling for 30 minutes and then at room temperature for 14 hours. The reaction mixture was diluted with ethyl acetate (30 ml) and washed with water (30 ml). The ethyl acetate layer was washed with 0.5 N HCl (30 ml) and water (30 ml×2), and dried over anhydrous magnesium sulfate, and then the solvent was distilled off. The residue was purified by silica gel chromatography (eluent: ethyl acetate/hexane=1/4) and then crystallized from diisopropyl ether to yield ethyl 6-[N-(2-fluorophenyl)sulfamoyl]-1-cyclohexene-1-carboxylate (Compound 10; 303 mg) as colorless needle-like crystals.

$^1$H-NMR (DMSO-$d_6$) δ1.07 (3H, t, J=7.2 Hz), 1.58–1.82 (2H, m), 2.05–2.46 (4H, m), 4.01 (2H, q, J=7.2 Hz), 4.32 (1H, d, J=4.6 Hz), 7.09–7.32 (4H, m), 7.44–7.54 (1H, m),9.91 (1H, brs).

% Calculated for $C_{15}H_{18}FNO_4S$: C, 55.03; H, 5.54; N, 4.28.

% Found: C, 55.09; H, 5.44; N, 4.33.

Example 10

Ethyl 2-sulfo-1-cyclohexene-1-carboxylate (1.0 g) obtained in Reference Example 1 was dissolved in thionyl chloride (3.0 ml) and heated under reflux for 14 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (12 ml) and the resultant mixture was added to a mixture consisting of 3-fluoroaniline (0.48 g), triethylamine (0.60 ml) and ethyl acetate (6 ml) with ice-cooling, and then stirred with ice-cooling for 30 minutes and then at room temperature for 25 hours. The reaction mixture was diluted with ethyl acetate (50 ml) and washed with water (50 ml) and 0.5 N HCl (50 ml) and water (50 ml×2) and dried over anhydrous magnesium sulfate, and then the solvent was distilled off. The residue was purified by silica gel chromatography (eluent: ethyl acetate/hexane=1/3), and the first effluent was distilled off under reduced pressure and the residue was crystallized from diisopropyl ether to yield ethyl 6-[N-3-fluorophenyl]sulfamoyl]-1-cyclohexene-1-carboxylate (Compound 11; 250 mg) as white powdery crystals.

$^1$H-NMR (DMSO-$d_6$) δ: 1.16 (3H, t, J=7.0 Hz), 1.60–1.80 (2H, m), 2.00–2.33 (4H, m), 3.98–4.15 (2H, m), 4.37 (1H, d, J=4.8 Hz), 6.87 (1H, dt, J=8.4 Hz, 2.2 Hz), 7.00–7.17 (1H, dt, J=8.4 Hz, 7.0 Hz), 10.33 (1H, brs).

% Calculated for $C_{15}H_{18}FNO_4S$: C, 55.03; H, 5.54; N, 4.28.

% Found: C, 55.09; H, 5.44; N, 4.33.

Example 11

Ethyl 2-sulfo-1-cyclohexene-1-carboxylate (0.72 g) obtained in Reference Example 1 was dissolved in thionyl chloride (2.1 ml) and heated under reflux for 5 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (10 ml) and the resultant mixture was added to a mixture consisting of 4-fluoroaniline (0.34 g), triethylamine (0.43 ml) and ethyl acetate (4 ml) with ice-cooling, and then stirred with ice-cooling for 30 minutes and then at room temperature for 40 hours. The reaction mixture was diluted with ethyl acetate (30 ml) and washed with water (30 ml) and 0.5 N HCl (30 ml) and water (30 ml×2) and dried over anhydrous magnesium sulfate, and then the solvent was distilled off. The residue was purified by silica gel chromatography (eluent: ethyl acetate/hexane=1/4), and the first effluent was distilled off under reduced pressure and the residue was crystallized from diisopropyl ether to yield 2-(4-fluorophenyl)-4,5,6,7-tetrahydro-1,2-benzoisothiazol-3(2H)-one 1,1-dioxide (Compound 68; 33 mg) as white powdery crystals. The second effluent was also distilled off under reduced pressure and the resultant residue was crystallized from ethyl acetate-diisopropyl ether to obtain white powdery crystals. This was purified by ODS column chromatoghraphy (eluent: methanol/water=7/3), and the effluent was concentrated under reduced pressure to precipitate crystals which was then collected by a filtration to yield ethyl 6-[N-(4-fluorophenyl)sulfamoyl]-1-cyclohexene-1-carboxylate (Compound 12; 36 mg) as colorless needle-like crystals. The mother liquor obtained when the first effluent was crystallized from ethyl acetate-diisopropyl ether was concentrated under reduced pressure and then purified by ODS column chromatoghraphy (eluent: methanol/water=7/3) to yield ethyl 2-[N-(4-fluorophenyl)sulfamoyl)-1-cyclohexene-1-carboxylate (Compound 18; 25 mg) as colorless powdery crystals.

Compound 12: $^1$H-NMR (DMSO-$d_6$) δ: 1.14 (3H, t, J=7.2 Hz), 1.55–1.77 (2H, m) , 1.98–2.44 (4H, m) , 3.97–4.13 (2H, m), 4.28 (1H, d, J=4.2 Hz), 7.10–7.28 (5H, m), 10.03 (1H, brs).

% Calculated for $C_{15}H_{18}NO_4S$: C, 55.03; H, 5.54; N, 4.28.

% Found: C, 54.69; H, 5.43; N, 4.38.

Compound 18: $^1$H-NMR (DMSO-$d_6$) δ: 1.20 (3H, t, J=7.2 Hz), 1.54 (4H, br) , 2.25 (4H, br), 4.11 (2H, q, J=7.2 Hz), 7.12 (2H, s), 7.16 (2H, s), 10.11 (1H, brs).

% Calculated for $C_{15}H_{18}NO_4S$: C, 55.03; H, 5.54; N, 4.28.

% Found: C, 55.07; H, 5.35; N, 4.33.

Compound 68: $^1$H-NMR (DMSO-$d_6$) δ: 1.75–1.88 (4H, m), 2.42–2.64 (4H, m), 7.40–7.49 (4H, m).

% Calculated for $C_{13}H_{12}FNO_3S$: C, 55.51; H, 4.30; N, 4.98.

% Found: C, 55.44; H, 4.24; N, 4.94.

Example 12

Ethyl 2-sulfo-1-cyclohexene-1-carboxylate (1.0 g) obtained in Reference Example 1 was dissolved in thionyl chloride (3.0 ml) and heated under reflux for 12 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (14 ml) and the resultant mixture was added to a mixture consisting of 2,6-difluoroaniline (0.56 g), triethylamine (0.60 ml) and ethyl acetate (6 ml) with ice-cooling, and then stirred with ice-cooling for 30 minutes and then at room temperature for 64 hours. The reaction mixture was diluted with ethyl acetate (80 ml) and washed with water (100 ml). The ethyl acetate layer was washed with 0.5 N HCl (100 ml×2) and a dilute brine (100 ml×3) and dried over anhydrous magnesium sulfate, and then the solvent was distilled off. The residue was purified by silica gel chromatography (eluent: ethyl acetate/hexane=1/3) and then crystallized from diisopropyl ether to yield ethyl 6-[N-(2,6-difluorophenyl)sulfamoyl]-1-cyclohexene-1-carboxylate (Compound 13; 135 mg) as colorless powdery crystals.

$^1$H-NMR (DMSO-$d_6$) δ: 1.00 (3H, t, J=7.0 Hz), 1.59–1.88 (2H, m), 2.08–2.56 (4H, m), 3.97 (2H, dq, J=7.0 Hz, 1.4 Hz), 4.39 (1H, d, J=5.0 Hz), 7.07–7.25 (3H, m), 7.34–7.50 (1H, m), 9.70 (1H, brs).

% Calculated for $C_{15}H_{17}F_2NO_4S$: C, 52.17; H, 4.96; N, 4.06.

% Found: C, 51.76; H, 4.88; N, 4.04.

Example 13

Ethyl 2-sulfo-1-cyclohexene-1-carboxylate (1.0 g) obtained in Reference Example 1 was dissolved in thionyl chloride (3.0 ml) and heated under reflux for 9 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (14 ml) and the resultant mixture was added to a mixture consisting of 2,3-difluoroaniline (0.56 g), triethylamine (0.60 ml) and ethyl acetate (6 ml) with ice-cooling, and then stirred with ice-cooling for 30 minutes and then at room temperature for 15 hours. The reaction mixture was diluted with ethyl acetate (80 ml) and washed with water (100 ml). The ethyl acetate layer was washed with 1 N HCl (100 ml×2) and dilute brine (100 ml×3) and dried over anhydrous magnesium sulfate, and then the solvent was distilled off. The residue was purified by silica gel chromatography (eluent: ethyl acetate/hexane=1/4) and then crystallized from diisopropyl ether to yield ethyl 6-[N-(2,3-difluorophenyl)sulfamoyl]-1-cyclohexene-1-carboxylate (Compound 14; 310 mg) as colorless powdery crystals.

$^1$H-NMR (DMSO-$d_6$) δ: 1.10 (3H, t, J=7.0 Hz), 1.58–1.83 (2H, m), 1.98–2.43 (4H, m), 4.02 (2H, q, J=7.0 Hz), 4.38 (1H, d, J=4.4 Hz), 7.13–7.36 (4H, m), 10.22 (1H, s).

% Calculated for $C_{15}H_{17}F_2NO_4S$: C, 52.17; H, 4.96; N, 4.06.

% Found: C, 52.18; H, 4.88; N, 4.11.

Example 14

Ethyl 2-sulfo-1-cyclohexene-1-carboxylate (1.0 g) obtained in Reference Example 1 was dissolved in thionyl chloride (3.0 ml) and heated under reflux for 24 hours and then the reaction mixture was evaporated under reduced pressure to dryness. The procedure involving an addition of hexane (10 ml) followed by an evaporation under reduced pressure to dryness was repeated three times to yield ethyl 2-chlorosulfonyl-1-cyclohexene-1-carboxylate. This was combined with ethyl acetate (14 ml) and the resultant mixture was added to a mixture consisting of 2,5-difluoroaniline (0.56 g), triethylamine (0.60 ml) and ethyl acetate (6 ml) with ice-cooling, and then stirred with ice-cooling for 30 minutes and then at room temperature for 22 hours. The reaction mixture was diluted with ethyl acetate (80 ml) and washed with water (100 ml). The ethyl acetate layer was washed with 1 N HCl (100 ml×2) and dilute brine (100 ml×3) and dried over anhydrous magnesium sulfate, and then the solvent was distilled off. The residue was purified by silica gel chromatography (eluent: ethyl acetate/hexane=1/4) and then crystallized from diisopropyl ether to yield ethyl 6-[N-(2,5-difluorophenyl)sulfamoyl]-1-cyclohexene-1-carboxylate (Compound 15; 200 mg) as colorless powdery crystals.

$^1$H-NMR (DMSO-$d_6$) δ: 1.13 (3H, t, J=7.0 Hz), 1.58–1.82 (2H, m), 2.05–2.43 (4H, m), 4.04 (2H, q, J=7.0 Hz), 4.38 (1H, d, J=3.6 Hz), 6.95–7.07 (1H, m), 7.13–7.18 (1H, m), 7.25–7.39 (2H, m), 10.24 (1H, brs).

% Calculated for $C_{15}H_{17}F_2NO_4S$: C, 52.17; H, 4.96; N, 4.06.

% Found: C, 52.23; H, 4.86; N, 4.11.

Example 15

Ethyl 2-sulfo-1-cyclohexene-1-carboxylate (1.0 g) obtained in Reference Example 1 was dissolved in thionyl chloride (3.0 ml) and heated under reflux for 23 hours and then the reaction mixture was evaporated under reduced pressure to dryness. The procedure involving an addition of hexane (10 ml) followed by evaporation under reduced pressure to dryness was repeated three times to yield ethyl 2-chlorosulfonyl-1-cyclohexene-1-carboxylate. This was combined with ethyl acetate (14 ml) and the resultant mixture was added to a mixture consisting of 3,4-difluoroaniline (0.56 g), triethylamine (0.60 ml) and ethyl acetate (6 ml) with ice-cooling, and then stirred with ice-cooling for 30 minutes and then at room temperature for 21 hours. The reaction mixture was diluted with ethyl acetate (80 ml) and washed with water (100 ml). The ethyl acetate layer was washed with 1 N HCl (100 ml×2) and dilute brine (100 ml×3) and dried over anhydrous magnesium sulfate, and then the solvent was distilled off. The residue was purified by silica gel chromatography (eluent: ethyl acetate/hexane=1/4) and then crystallized from diisopropyl ether to yield ethyl 6-[N-(3,4-difluorophenyl)sulfamoyl]-1-cyclohexene-1-carboxylate (Compound 16; 170 mg) as colorless powdery crystals.

$^1$H-NMR (DMSO-$d_6$) δ: 1.16 (3H, t, J=7.0 Hz), 1.58–1.80 (2H, m), 1.98–2.42 (4H, m), 3.99–4.15 (2H, m), 4.34 (1H, d, J=3.6 Hz), 6.96–7.04 (1H, m), 7.13–7.29 (2H, m), 7.41 (1H, dt, J=10.6 Hz, 9.0 Hz), 10.29 (1H, brs).

% Calculated for $C_{15}H_{17}F_2NO_4S$: C, 52.17; H, 4.96; N, 4.06.

% Found: C, 52.29; H, 4.78; N, 4.04.

Example 16

Ethyl 2-sulfo-1-cyclohexene-1-carboxylate (1.0 g) obtained in Reference Example 1 was dissolved in thionyl chloride (3.0 ml) and heated under reflux for 17 hours and then the reaction mixture was evaporated under reduced pressure to dryness. The procedure involving an addition of hexane (10 ml) followed by evaporation under reduced pressure to dryness was repeated three times to yield ethyl 2-chlorosulfonyl-1-cyclohexene-1-carboxylate. This was combined with ethyl acetate (14 ml) and the resultant mixture was added to a mixture consisting of 3,5-difluoroaniline (0.56 g), triethylamine (0.60 ml) and ethyl acetate (6 ml) with ice-cooling, and then stirred with ice-cooling for 30 minutes and then at room temperature for 21 hours. The reaction mixture was diluted with ethyl acetate (80 ml) and washed with water (100 ml). The ethyl acetate layer was washed with 1 N HCl (100 ml×2) and dilute brine (100 ml×3) and dried over anhydrous magnesium sulfate, and then the solvent was distilled off. The residue was purified by silica gel chromatography (eluent: ethyl acetate/hexane=1/3) and then crystallized from diisopropyl ether to yield ethyl 6-[N-(3,5-difluorophenyl)sulfamoyl]-1-cyclohexene-1-carboxylate (Compound 17; 250 mg) as colorless powdery crystals.

$^1$H-NMR (DMSO-$d_6$) δ: 1.18 (3H, t, J=7.0 Hz), 1.58–1.82 (2H, m), 1.96–2.44 (4H, m), 3.99–4.16 (2H, m), 4.42 (1H, d, J=4.8 Hz), 6.83–6.95 (3H, m), 7.18 (1H, t, J=4 Hz), 10.59 (1H, brs).

% Calculated for $C_{15}H_{17}F_2NO_4S$: C, 52.17; H, 4.96; N, 4.06.

Found: C, 52.22; H, 5.01; N, 4.12.

Example 17

Ethyl 6-[N-(2,4-difluorophenyl)sulfamoyl]-1-cyclohexene-1-carboxylate (Compound 3, 200 mg) obtained in Example 3 was resolved by high pressure liquid chromatography (CHIRALPAK AD; eluent: hexane/ethanol=9/1) into two optical isomers to yield 1-ethyl 6-[N-(2,4-difluorophenyl)sulfamoyl]-1-cyclohexene-1-carboxylate (Compound 19, 62 mg) and d-ethyl 6-[N-(2,4-difluorophenyl)sulfamoyl]-1-cyclohexene-1-carboxylate (Compound 20, 51 mg) each as a white powder.

Compound 19 (40 mg) was crystallized from diisopropyl ether (2 ml) to obtain white powdery crystals (26 mg) of Compound 19.

$^1$H-NMR ($d_6$-DMSO) δ: 1.07 (3H, t, J=7.2 Hz), 1.58–1.82 (2H, m), 1.98–2.44 (4H, m), 4.01 (2H, q, J=7.2 Hz), 4.28 (1H, d, J=4.6 Hz), 7.04–7.15 (2H, m), 7.28–7.54 (2H, m), 9.85 (1H, s).

% Calculated for $C_{15}H_{17}F_2NO_4S$: C, 52.17; H, 4.96; N, 4.06.

% Found: C, 52.20; H, 4.85; N, 4.20.

$[α]^{20}_D$ −105.7° (c=0.5, in methanol).

Compound 20 (35 mg) was crystallized from diisopropyl ether (2 ml) to obtain white powdery crystals (18 mg) of Compound 20.

$^1$H-NMR ($d_6$-DMSO) δ: 1.07 (3H, t, J=7.2 Hz), 1.58–1.82 (2H, m), 1.98–2.44 (4H, m), 4.01 (2H, q, J=7.2 Hz), 4.28 (1H, d, J=4.6 Hz), 7.05–7.15 (2H, m), 7.28–7.55 (2H, m), 9.86 (1H, brs).

% Calculated for $C_{15}H_{17}F_2NO_4S$: C, 52.17; H, 4.96; N, 4.06.

% Found: C, 52.10; H, 4.83; N, 4.21.

$[α]^{20}_D$ +105.9° (c=0.5, in methanol).

Example 18

Ethyl 2-sulfo-1-cyclohexene-1-carboxylate (2.0 g) obtained in Reference Example 1 was dissolved in thionyl chloride (6 ml) and heated under reflux for 15 hours and then the reaction mixture was evaporated under reduced pressure to dryness. The procedure involving an addition of hexane (10 ml) followed by an evaporation under reduced pressure to dryness was repeated three times to yield ethyl 2 2-chlorosulfonyl-1-cyclohexene-1-carboxylate. This was combined with ethyl acetate (20 ml) and the resultant mixture was added to a mixture consisting of ethyl anthranylate (1.42 g), triethylamine (1.20 ml) and ethyl acetate (12 ml) with ice-cooling, and then stirred with ice-cooling for 30 minutes and then at room temperature for 70 hours. The reaction mixture was diluted with ethyl acetate (80 ml) and washed with water (100 ml), 1 N HCl (100 ml×2) and dilute brine (100 ml×3) and dried over anhydrous magnesium sulfate, and then the solvent was distilled off. The residue was purified by silica gel chromatography (eluent: ethyl acetate/hexane=1/4) and then crystallized from diisopropyl ether to yield ethyl 6-[N-(2-ethoxycarbonylphenyl)sulfamoyl]-1-cyclohexene-1-carboxylate (Compound 21; 0.44 g) as colorless crystals.

$^1$H-NMR ($d_6$-DMSO) δ: 1.12 (3H, t, J=7.2 Hz), 1.35 (3H, t, J=7.2 Hz), 1.62–1.84 (2H, m), 1.92–2.35 (4H, m), 3.85–4.10 (2H, m), 4.35 (2H, q, J=7.2 Hz), 4.50 (1H, d, J=4.2 Hz), 7.15–7.23 (2H, m), 7.60–7.72 (2H, m), 8.01 (1H, d, J=8.0 Hz), 10.42 (1H, s).

% Calculated for $C_{18}H_{23}NO_6S$: C, 56.68; H, 6.08; N, 3.67.

% Found: C, 56.56; H, 6.05; N, 3.68.

Example 19

To a solution of ethyl 6-[N-(2,4-difluorophenyl)sulfamoyl]-1-cyclohexene-1-carboxylate (Compound 3, 300 mg) obtained in Example 3 in methanol (6 ml), concentrated sulfuric acid (0.4 ml) was added and the mixture was stirred under reflux for 8 days. The reaction mixture was concentrated under reduced pressure and diluted with ethyl acetate (30 ml) and washed with water (30 ml). The ethyl acetate layer was washed with water (30 ml×2) and dried over anhydrous magnesium sulfate and the solvent was distilled off under reduced pressure. The residue was purified by silica gel chromatography (eluent: ethyl acetate/hexane=1/5→ethyl acetate/hexane=1/2) and then crystallized from diisopropyl ether to yield methyl 6-[N-(2,4-difluorophenyl)sulfamoyl]-1-cyclohexene-1-carboxylate (Compound 22; 95 mg) as colorless powdery crystals.

$^1$H-NMR ($d_6$-DMSO) δ: 1.58–1.82 (2H, m), 1.98–2.42 (4H, m), 3.56 (3H, s), 4.30 (1H, d, J=4.6 Hz), 7.05–7.15 (2H, m), 7.28–7.55 (2H, m), 9.85 (1H, s).

% Calculated for $C_{14}H_{15}NO_4S$: C, 50.75; H, 4.56; N, 4.23.

% Found: C, 50.79; H, 4.49; N, 4.07.

Example 20

To a solution of ethyl 6-[N-(2,4-difluorophenyl)sulfamoyl]-1-cyclohexene-1-carboxylate (Compound 3, 300 mg) obtained in Example 3 in 1-propanol (6 ml), concentrated sulfuric acid (0.3 ml) was added and the mixture was stirred under reflux for 50 hours. The reaction mixture was concentrated under reduced pressure and diluted with ethyl acetate (30 ml) and washed with water (30 ml). The ethyl acetate layer was washed with water (30 ml×2) and dried over anhydrous magnesium sulfate and the solvent was distilled off under reduced pressure. The residue was subjected to silica gel chromatography (eluent: ethyl acetate/hexane=1/5) and desired fractions were concentrated under reduced pressure. The residue was purified by column chromatography on octadecylsilica (ODS) (eluent: methanol/water=4/1) and then crystallized from diisopropyl ether to yield propyl 6-[N-(2,4-difluorophenyl)sulfamoyl]-1-cyclohexene-1-carboxylate (Compound 23, 60 mg) as colorless crystals.

$^1$H-NMR (d$_6$-DMSO) δ: 0.79 (3H, t, J=7.4 Hz), 1.38–1.82 (4H, m), 2.02–2.45 (4H, m), 3.91 (2H, t, J=6.4 Hz), 4.27 (1H, d, J=4.8 Hz), 7.05–7.12 (2H, m), 7.28–7.53 (2H, m), 9.86 (1H, s).

% Calculated for C$_{16}$H$_{19}$F$_2$NO$_4$S: C, 53.47; H, 5.33; N, 3.90.

% Found: C, 53.01; H, 5.34; N, 3.63.

Example 21

To a solution of ethyl 6-[N-(4-chloro-2-fluorophenyl)sulfamoyl]-1-cyclohexene-1-carboxylate obtained in Example 1 (Compound 1, 250 mg) in methanol (5 ml), concentrated sulfuric acid (0.2 ml) was added and the mixture was stirred under reflux for 8 days hours. The reaction mixture was concentrated under reduced pressure and diluted with ethyl acetate (30 ml) and washed with water (30 ml). The ethyl acetate layer was washed with water (30 ml×2) and dried over anhydrous magnesium sulfate and the solvent was distilled off under reduced pressure. The residue was ,subjected to silica gel chromatography (eluent: ethyl acetate/hexane=1/4) and desired fractions were concentrated under reduced pressure. The residue was purified by an ODS column chromatography (eluent: methanol/water=4/1) and then crystallized from diisopropyl ether to yield methyl 6-[N-(4-chloro-2-fluorophenyl)sulfamoyl]-1-cyclohexene-1-carboxylate (Compound 24, 58 mg) as colorless prism-like crystals.

$^1$H-NMR (d$_6$-DMSO) δ: 1.58–1.82 (2H, m), 1.98–2.44 (4H, m), 3.56 (3H, s), 4.34 (1H, br), 7.14 (1H, br), 7.25–7.50 (3H, m), 10.04 (1H, brs).

% Calculated for C$_{14}$H$_{15}$ClFNO$_4$S: C, 48.35; H, 4.35; N, 4.03.

% Found: C, 48.27; H, 4.43; N, 4.08.

Example 22

To a solution of ethyl 6-[N-(2,4-difluorophenyl)sulfamoyl]-1-cyclohexene-1-carboxylate obtained in Example 3 (Compound 3, 200 mg) in 2-propanol (4 ml), concentrated sulfuric acid (0.2 ml) was added and the mixture was stirred under reflux for 10 days hours. The reaction mixture was concentrated under reduced pressure and diluted with ethyl acetate (30 ml) and washed with water (30 ml). The ethyl acetate layer was washed with dilute brine (30 ml×2) and dried over anhydrous magnesium sulfate and the solvent was distilled off under reduced pressure. The residue was purified by silica gel chromatography (eluent: ethyl acetate/hexane=1/4) and then crystallized from diisopropyl ether to yield isopropyl 6-[N-(2,4-difluorophenyl)sulfamoyl]-1-cyclohexene-1-carboxylate (Compound 25, 20 mg) as white powdery crystals.

$^1$H-NMR (d$_6$-DMSO) δ: 1.04 (3H, d, J=6.4 Hz), 1.09 (3H, d, J=6.4 Hz), 1.58–1.82 (2H, m), 2.02–2.45 (4H, m), 4.25 (1H, d, J=4.8 Hz), 4.83 (1H, quintet, J=6.4 Hz), 7.05–7.15 (2H, m), 7.30–7.54 (2H, m), 9.86 (1H, s).

% Calculated for C$_{16}$H$_{19}$F$_2$NO$_4$S: C, 53.47; H, 5.33; N, 3.90.

% Found: C, 53.67; H, 5.09; N, 3.77.

Example 23

Ethyl 2-sulfo-1-cyclohexene-1-carboxylate (1.0 g) obtained in Reference Example 1 was dissolved in thionyl chloride (3 ml) and heated under reflux for 9 hours and then the reaction mixture was evaporated under reduced pressure to dryness. The procedure involving an addition of hexane (10 ml) followed by evaporation under reduced pressure to dryness was repeated three times to yield ethyl 2-chlorosulfonyl-1-cyclohexene-1-carboxylate. This was combined with ethyl acetate (12 ml) and the resultant mixture was added to a mixture consisting of methyl anthranylate (0.65 g), triethylamine (0.60 ml) and ethyl acetate (6 ml) with ice-cooling, and then stirred with ice-cooling for 30 minutes and then at room temperature for 24 hours. The reaction mixture was diluted with ethyl acetate (50 ml) and washed with water (50 ml). The ethyl acetate layer was washed with 0.1 N HCl (50 ml×2) and saturated brine (50 ml) and dried over anhydrous sodium sulfate, and then the solvent was distilled off. The residue was purified by flash column chromatography (eluent: ethyl acetate/hexane=1/5) and then crystallized from diisopropyl ether to yield ethyl 6-[N-(2-methoxycarbonylphenyl)sulfamoyl]-1-cyclohexene-1-carboxylate (Compound 26; 190 mg) as pale yellow powdery crystals.

$^1$H-NMR (d$_6$-DMSO) δ: 1.21 (3H, t, J=7.0 Hz), 1.68–2.36 (6H, m), 3.90 (3H, s), 3.93–4.07 (2H, m), 4.50 (1H, d, J=4.4 Hz), 7.15–7.23 (2H, m), 7.61–7.69 (2H, m), 8.0 (1H, d, J=8.8 Hz), 10.39 (1H, 5).

% Calculated for C$_{17}$H$_{21}$NO$_6$S: C, 55.57; H, 5.76; N, 3.81.

% Found C, 55.62; H, 5.76; N, 3.78.

Example 24

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate which was then reacted with 2-fluoro-4-methylaniline (0.54 g) to yield ethyl 6-[N-(2-fluoro-4-methylphenyl)sulfamoyl]-1-cyclohexene-1-carboxylate (Compound 27; 223 mg) as colorless powdery crystals.

$^1$H-NMR (d$_6$-DMSO) δ: 1.08 (3H, t, J=7.0 Hz), 1.62–1.80 (2H, m), 2.00–2.43 (4H, m), 2.29 (3H, s), 4.01 (2H, q, J=7.0 Hz), 4.27 (1H, d, J=5.0 Hz), 6.97–7.11 (3H, m), 7.33 (1H, t, J=8.4 Hz), 9.71 (1H, s).

% Calculated for C$_{16}$H$_{20}$FNO$_4$S: C, 56.29; H, 5.90; N, 4.10.

% Found: C, 56.26; H, 5.80; N, 4.03.

Example 25

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate which was then reacted with o-chloroaniline (0.55 g) to yield ethyl 6-[N-(2-chlorophenyl)sulfamoyl]-1-cyclohexene-1-carboxylate (Compound 28; 0.28 g) as white crystals.

¹H-NMR (d₆-DMSO) δ: 1.05 (3H, t, J=7.0 Hz), 1.55–1.84 (2H, m), 1.99–2.58 (4H, m), 4.00 (2H, q, J=7.0 Hz), 4.30 (1H, d, J=5.2 Hz), 7.11 (1H, br), 7.19–7.39 (2H, m), 7.48–7.56 (2H, m), 9.66 (1H, s).

% Calculated for $C_{15}H_{18}ClNO_4S$: C, 52.40; H, 5.28; N, 4.07.

% Found: C, 52.39; H, 5.28; N, 4.19.

Example 26

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate and reacted with 2-chloro-4-fluoroaniline (0.62 g) to yield ethyl 6-[N-(2-chloro-4-fluorophenyl)sulfamoyl]-1-cyclohexene-1-carboxylate (Compound 29; 0.35 g) as white crystals.

¹H-NMR (d₆-DMSO) δ: 1.05 (3H, t, J=7.0 Hz), 1.52–1.83 (2H, m), 1.98–2.46 (4H, m), 4.00 (2H, q, J=7.0 Hz), 4.29 (1H, d, J=4.8 Hz), 7.10 (1H, br), 7.20–7.30 (1H, m), 7.49–7.58 (2H, m), 9.80 (1H, s).

% Calculated for $C_{15}H_{17}ClFNO_4S$: C, 49.79; H, 4.74; N, 3.87.

% Found: C, 49.74; H, 4.76; N, 3.98.

Example 27

By the procedure similar to that employed in Example 23, ethyl 2-sulfo-1-cyclohexene-1-carboxylate (1.0 g) obtained in Reference Example 1 was derivatized to ethyl 2-chlorosulfonyl-1-cyclohexene-1-carboxylate which was then reacted with p-chloroaniline (0.54 g) to yield ethyl 6-[N-(4-chlorophenyl)sulfamoyl]-1-cyclohexene-1-carboxylate (Compound 30; 0.24 g) as white crystals.

¹H-NMR (d₆-DMSO) δ: 1.15 (3H, t, J=7.0 Hz), 1.51–1.78 (2H, m), 1.95–2.20 (4H, m), 3.96–4.13 (2H, m), 4.32 (1H, d, J=4.0 Hz), 7.13 (1H, t, J=4.0 Hz), 7.20–7.24 (2H, m), 7.34–7.39 (2H, m), 10.17 (1H, s).

% Calculated for $C_{15}H_{18}ClNO_4S$: C, 52.40; H, 5.28; N, 4.07.

% Found: C, 52.33; H, 5.11; N, 3.87.

Example 28

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate which was then reacted with 2,3,4-trifluoroaniline (0.63 g) to yield ethyl 6-[N-(2,3,4-trifluorophenyl)sulfamoyl]-1-cyclohexene-1-carboxylate (Compound 31; 0.36 g) as white crystals.

¹H-NMR (d₆-DMSO) δ: 1.11 (3H, t, J=7.0 Hz), 1.54–1.86 (2H, m), 1.95–2.48 (4H, m), 4.03 (2H, q, J=7.0 Hz), 4.34 (1H, d, J=4.4 Hz), 7.13 (1H, br), 7.29–7.35 (2H, m), 10.15 (1H, s).

% Calculated for $C_{15}H_{16}F_3NO_4S$: C, 49.58; H, 4.44; N, 3.85.

% Found C, 49.51; H, 4.35; N, 3.76.

Example 29

To a solution of ethyl 6-[N-(2,4-difluorophenyl)sulfamoyl]-1-cyclohexene-1-carboxylate obtained in Example 3 (Compound 3, 200 mg) in isobutyl alcohol (4 ml), a concentrated sulfuric acid (0.2 ml) was added and the mixture was stirred at 80 to 85° C. for 7 days. After cooling, the reaction mixture was diluted with ethyl acetate (80 ml) and washed with water (50 ml). The ethyl acetate layer was washed with 5% aqueous solution of sodium bicarbonate (50 ml) and water (50 ml×2), dried over anhydrous magnesium sulfate and then evaporated under reduced pressure to dryness. The residue was purified by silica gel chromatography (eluent: ethyl acetate/hexane=1/4) and then crystallized from diisopropyl ether to yield isobutyl 6-[N-(2,4-difluorophenyl)sulfamoyl]-1-cyclohexene-1-carboxylate (Compound 32; 35 mg) as white crystals.

¹H-NMR (d₆-DMSO) δ: 0.80 (6H, d, J=6.8 Hz), 1.58–1.84 (2H, m), 2.00–2.47 (4H, m), 3.35–3.45 (1H, m), 3.75 (2H, d, J=6.8 Hz), 4.27 (1H, d, J=4.8 Hz), 7.03–7.13 (2H, m), 7.27–7.53 (2H, m), 9.85 (1H, s).

% Calculated for $C_{17}H_{21}F_2NO_4S$: C, 54.68; H, 5.67; N, 3.75.

% Found: C, 54.64; H, 5.49; N, 3.78.

Example 30

To a solution of ethyl 6-[N-(2,4difluorophenyl)sulfamoyl]-1-cyclohexene-1-carboxylate obtained in Example 3 (Compound 3, 180 mg) in 1-butanol (5 ml), a concentrated sulfuric acid (0.12 ml) was added and the mixture was stirred at 80 to 85° C. for 7 days. After cooling, the reaction mixture was diluted with ethyl acetate (60 ml) and washed with water (60 ml). The ethyl acetate layer was washed with water (60 ml×5), dried over anhydrous magnesium sulfate and then evaporated under reduced pressure to dryness. The residue was purified by silica gel chromatography (eluent: ethyl acetate/hexane=1/4) and then crystallized from diisopropyl ether to yield butyl 6-[N-(2,4-difluorophenyl)sulfamoyl]-1-cyclohexene-1-carboxylate (Compound 33, 52 mg) as white crystals.

¹H-NMR (d₆-DMSO) δ: 0.83 (3H, t, J=7 Hz), 1.18–1.82 (6H, m), 2.00–2.42 (4H, m), 3.95 (2H, br), 4.24 (1H, d, J=4.4 Hz), 7.09 (2H, br), 7.30–7.49 (2H, m), 9.86 (1H, brs).

% Calculated for $C_{17}H_{21}F_2NO_4S$: C, 54.68; H, 5.67; N, 3.75.

% Found: C, 54.64; H, 5.48; N, 4.05.

Example 31

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate which was then reacted with 4-bromo-2-fluoroaniline (0.81 g) to yield ethyl 6-[N-(4-bromo-2-fluorophenyl)sulfamoyl]-1-cyclohexene-1-carboxylate (Compound 34; 0.23 g) as a white crystals.

¹H-NMR (d₆-DMSO) δ: 1.10 (3H, t, J=7.0 Hz), 1.54–1.83 (2H, m), 1.92–2.46 (4H, m), 4.02 (2H, q, J=7.0 Hz), 4.32 (1H, d, J=4.4 Hz), 7.12 (1H, t, J=4.2 Hz), 7.35–7.48 (2H, m), 7.56–7.63 (1H, m), 10.04 (1H, s).

% Calculated for $C_{15}H_{17}BrFNO_4S$: C, 44.35; H, 4.22; N, 3.45.

% Found: C, 44.40; H, 4.25; N, 3.76.

Example 32

By the procedure similar to that employed in Example 23, ethyl 2-sulfo-1-cyclohexene-1-carboxylate (1.0 g) obtained in Reference Example 1 was derivatized to ethyl 2-chlorosulfonyl-1-cyclohexene-1-carboxylate which was then reacted with 2,4-dichloroaniline (0.69 g) to yield ethyl 6-[N-(2,4-dichlorophenyl)sulfamoyl]-1-cyclohexene-1-carboxylate (Compound 35; 0.24 g) as a white crystals.

¹H-NMR (d₆-DMSO) δ: 1.07 (3H, t, J=7.0 Hz), 1.54–1.82 (2H, m), 1.95–2.45 (4H, m), 4.01 (2H, q, J=7.0 Hz), 4.32 (1H, d, J=4.8 Hz), 7.12 (1H, br), 7.40–7.67 (3H, m), 9.81 (1H, brs).

% Calculated for $C_{15}H_{17}Cl_2NO_4S$: C, 47.63; H, 4.53; N, 3.70.

% Found: C, 47.67; H, 4.59; N, 3.89.

Example 33

2-Acetoaminophene (0.29 g) was dissolved in ethyl acetate (2.4 ml) and the resultant solution was admixed with triethylamine (0.46 ml) with ice-cooling, and then a solution of ethyl 2-chlorosulfonyl-1-cyclohexene-1-carboxylate (0.42 g) obtained in Reference Example 2 in ethyl acetate (4.8 ml) was added dropwise. The reaction mixture was stirred under a nitrogen stream at 0° C. for 30 minutes and then at room temperature for 20 hours. The reaction mixture was diluted with ethyl acetate and washed successively with water (40 ml), hydrochloric acid (40 ml), water (40 ml×2) and then saturated brine (40 ml). The ethyl acetate layer was dried over magnesium sulfate and the solvent was distilled off under reduced pressure. The residue was purified by column chromatography on silica gel (eluent: ethyl acetate/hexane=1:4). A desired fraction was concentrated and the residue was crystallized from a mixture of ethyl acetate and hexane to yield ethyl 6-[N-(2-acetoxyphenyl)sulfamoyl]-1-cyclohexene-1-carboxylate (Compound 36; 0.25 g) as white crystals.

¹H-NMR (d₆-DMSO) δ: 1.12 (3H, t, J=7.0 Hz), 1.58–1.83 (2H, m), 1.90–2.40 (4H, m), 2.68 (3H, s), 3.88–4.06 (2H, m), 4.48 (1H, d, J=4.4 Hz), 7.17–7.26 (2H, m), 7.65–7.71 (2H, m), 8.09–8.13 (1H, m), 11.31 (1H, s).

% Calculated for $C_{17}H_{21}NO_5S$: C, 58.10; H, 6.02; N, 3.99.

% Found: C, 58.12; H, 5.93; N, 4.10.

Example 34

By the procedure similar to that employed in Example 23, ethyl 2-sulfo-1-cyclohexene-1-carboxylate (1.0 g) obtained in Reference Example 1 was derivatized to ethyl 2-chlorosulfonyl-1-cyclohexene-1-carboxylate which was then reacted with m-chloroaniline (0.54 g) to yield ethyl 6-[N-(3-chlorophenyl)sulfamoyl]-1-cyclohexene-1carboxylate (Compound 37; 0.15 g) as white crystals.

¹H-NMR (d₆-DMSO) δ: 1.16 (3H, t, J=7.0 Hz), 1.54–1.81 (2H, m), 1.94–2.38 (4H, m), 4.00–4.15 (2H, m), 4.36 (1H, d, J=4.4 Hz), 7.07 (1H, br), 7.11–7.37 (4H, m), 10.29 (1H, s).

% Calculated for $C_{15}H_{18}ClNO_4S$: C, 52.40; H, 5.28; N, 4.07.

% Found: C, 52.44; H, 5.21; N, 4.32.

Example 35

By the procedure similar to that employed in Example 33, ethyl 2-chlorosulfonyl-1-cyclohexene-1-carboxylate (0.42 g) obtained in Reference Example 2 was reacted with 2,3-dichloroaniline (0.35 g) to yield ethyl 6-[N-(2,3-dichlorophenyl)sulfamoyl]-1-cyclohexene-1-carboxylate (Compound 38; 0.23 g) as white crystals.

¹H-NMR (d₆-DMSO) δ1.08 (3H, t, J=7.0 Hz), 1.55–1.86 (2H, m), 1.97–2.46 (4H, m), 4.01 (2H, q, J=7.0 Hz), 4.36 (1H, d, J=4.8 Hz), 7.13 (1H, br), 7.32–7.56 (3H, m), 9.87 (1H, s).

% Calculated for $C_{15}H_{17}Cl_2NO_4S$: C, 47.63; H, 4.53; N, 3.70.

% Found: C, 47.43; H, 4.33; N, 4.02.

Example 36

By the procedure similar to that employed in Example 23, ethyl 2-sulfo-1-cyclohexene-1-carboxylate (1.0 g) obtained in Reference Example 1 was derived to ethyl 2-chlorosulfonyl-1-cyclohexene-1-carboxylate which was then reacted with o-ethylaniline (0.52 g) to yield ethyl 6-[N-(2-ethylphenyl)sulfamoyl]-1-cyclohexene-1-carboxylate (Compound 39; 0.20 g) as white crystals.

¹H-NMR (d₆-DMSO) δ: 1.06 (3H, t, J=7.0 Hz), 1.16 (3H, t, J=7.6 Hz), 1.52–1.86 (2H, m), 1.99–2.50 (4H, m), 2.72 (2H, q, J=7.6 Hz), 4.01 (2H, q, J=7.0 Hz), 4.39 (1H, d, J=4.8 Hz), 7.10 (1H, br), 7.16–7.38 (4H, m), 9.18 (1H, s).

% Calculated for $C_{17}H_{23}NO_4S$: C, 60.51; H, 6.87; N, 4.15.

% Found: C, 60.15; H, 6.70; N, 4.10.

Example 37

By the procedure similar to that employed in Example 33, ethyl 2-chlorosulfonyl-1-cyclohexene-1-carboxylate (0.42 g) obtained in Reference Example 2 was reacted with 4-(2H-1,2,3-triazol-2-yl)aniline (0.35 g) to yield ethyl 6-[N-[4-(2H-1,2,3-triazol-2-yl)phenyl]sulfamoyl]-1-cyclohexene-1-carboxylate (Compound 40; 0.48 g) as white crystals.

¹H-NMR (d₆-DMSO)δ: 1.15 (3H, t, J=7.0 Hz), 1.55–1.80 (2H, m), 2.02–2.44 (4H, m), 4.00–4.15 (2H, m), 4.38 (1H, d, J=4.4 Hz), 7.15 (1H, br), 7.39 (2H, d, J=9.2 Hz), 7.96 (2H, d, J=9.2 Hz), 8.08 (2H, s), 10.29 (1H, s).

% Calculated for $C_{17}H_{20}N_4O_4S$: C, 54.24; H, 5.36; N, 14.88

% Found: C, 54.38; H, 5.10; N, 15.01.

Example 38

By the procedure similar to that employed in Example 33, ethyl 2-chlorosulfonyl-1-cyclohexene-1-carboxylate (0.41 g) obtained in Reference Example 2 was reacted with 2,5-dichloroaniline (0.34 g) to yield ethyl 6-[N-(2,5-dichlorophenyl)sulfamoyl]-1-cyclohexene-1-carboxylate (Compound 41; 0.21 g) as white crystals.

¹H-NMR (d₆-DMSO)δ: 1.10 (3H, t, J=7.0Hz), 1.57–1.85 (2H, m), 1.96–2.45 (4H, m), 4.04 (2H, q, J=7.0 Hz), 4.36 (1H, d, J=4.4 Hz), 7.15 (1H, br), 7.25–7.31 (1H, m), 7.51–7.59 (2H, m), 9.90 (1H, s).

% Calculated for $C_{15}H_{17}Cl_2NO_4S$: C, 47.63; H, 4.53; N, 3.70

% Found: C, 47.75; H, 4.66; N, 3.80.

Example 39

By the procedure similar to that employed in Example 33, ethyl 2-chlorosulfonyl-1-cyclohexene-1-carboxylate (0.40 g) obtained in Reference Example 2 was reacted with 2-trifluoromethoxyaniline (0.37 g) to yield ethyl 6-[N-(2-trifluoromethoxyphenyl)sulfamoyl]-1-cyclohexene-1-carboxylate (Compound 42; 316 mg) as colorless powdery crystals.

¹H-NMR (d₆-DMSO)δ: 1.10 (3H, t, J=7.0 Hz), 1.54–1.80 (2H, m), 2.00–2.51 (4H, m), 4.04 (2H, q, J=7.0 Hz), 4.38 (1H, d, J=5.2 Hz), 7.13–7.40 (4H, m), 7.59–7.64 (1H, m), 10.02 (1H, s).

% Calculated for $C_{16}H_{18}F_3NO_5S$: C, 48.85; H, 4.61; N, 3.56

Found: C, 48.92; H, 4.62; N, 3.81.

Example 40

By the procedure similar to that employed in Example 33, ethyl 2-chlorosulfonyl-1-cyclohexene-1-carboxylate (0.40 g) obtained in Reference Example 2 was reacted with 2,4,5-trifluoroaniline (0.31 g) to yield ethyl 6-[N-(2,4,5-trifluorophenyl)sulfamoyl]-1-cyclohexene-1-carboxylate (Compound 43; 0.30 g) as white crystals.

$^1$H-NMR (d$_6$-DMSO)δ: 1.13 (3H, t, J=7.0 Hz), 1.55–1.85 (2H, m), 1.96–2.48 (4H, m), 4.05 (2H, q, J=7.0 Hz), 4.35 (1H, d, J=4.4 Hz), 7.14 (1H, br), 7.47–7.71 (2H, m), 10.17 (1H, s).

% Calculated for C$_{15}$H$_{16}$F$_3$NO$_4$S: C, 49.58; H, 4.44; N, 3.85

% Found: C, 49.83; H, 4.32; N, 4.01.

Example 41

By the procedure similar to that employed in Example 33, ethyl 2-chlorosulfonyl-1-cyclohexene-1-carboxylate (0.41 g) obtained in Reference Example 2 was reacted with 4-(2H-tetrazol-2-yl)aniline (0.34 g) to yield ethyl 6-[N-[4-(2H-tetrazol-2-yl)phenyl]sulfamoyl]-1-cyclohexene-1-carboxylate (Compound 44; 0.45 g) as white crystals.

$^1$H-NMR (d$_6$-DMSO)δ: 1.15 (3H, t, J=7.0 Hz), 1.57–1.85 (2H, m), 1.97–2.45 (4H, m), 3.98–4.14 (2H, m), 4.42 (1H, d, J=4.4 Hz), 7.17 (1H, br), 7.46 (2H, d, J=9.2 Hz), 8.04 (2H, d, J=9.2 Hz), 9.20 (1H, s), 10.50 (1H, s).

% Calculated for C$_{16}$H$_{19}$N$_5$O$_4$S: C, 50.92; H, 5.07; N, 18.56

% Found: C, 51.05; H, 5.24; N, 18.50.

Example 42

By the procedure similar to that employed in Example 33, ethyl 2-chlorosulfonyl-1-cyclohexene-1-carboxylate (0.42 g) obtained in Reference Example 2 was reacted with 2-chloro-4-methylaniline (0.31 g) to yield ethyl 6-[N-(2-chloro-4-methylphenyl)sulfamoyl]-1-cyclohexene-1-carboxylate (Compound 45; 0.27 g) as white crystals.

$^1$H-NMR (d$_6$-DMSO)δ: 1.06 (3H, t, J=7.0 Hz), 1.51–1.83 (2H, m), 1.99–2.46 (4H, m), 2.29 (3H, s), 4.00 (2H, q, J=7.0 Hz), 4.29 (1H, d, J=5.4 Hz), 7.08 (1H, br), 7.12–7.16 (1H, m), 7.33–7.41 (2H, m), 9.53 (1H, s).

% Calculated for C$_{16}$H$_{20}$ClNO$_4$S: C, 53.70; H, 5.63; N, 3.91

% Found: C, 53.67; H, 5.61; N, 3.97.

Example 43

By the procedure similar to that employed in Example 33, ethyl 2-chlorosulfonyl-1-cyclohexene-1-carboxylate (0.41 g) obtained in Reference Example 2 was reacted with 4-fluoro-2-methylaniline (0.26 g) to yield ethyl 6-[N-(4-fluoro-2-methylphenyl)sulfamoyl]-1-cyclohexene-1-carboxylate (Compound 46; 0.36 g) as white crystals.

$^1$H-NMR (d$_6$-DMSO)δ: 1.06 (3H, t, J=7.0 Hz), 1.56–1.84 (2H, m), 2.00–2.46 (4H, m), 2.31 (3H, s), 4.01 (2H, q, J=7.0 Hz), 4.30 (1H, d, J=5.0 Hz), 6.96–7.13 (3H, m), 7.32–7.39 (1H, m), 9.24 (1H, s).

% Calculated for C$_{16}$H$_{20}$FNO$_4$S: C, 56.29; H, 5.90; N, 4.10

% Found C, 56.33; H, 5.90; N, 3.93.

Example 44

By the procedure similar to that employed in Example 33, ethyl 2-chlorosulfonyl-1-cyclohexene-1-carboxylate (0.41 g) obtained in Reference Example 2 was reacted with 2,6-dichloroaniline (0.34 g) to yield ethyl 6-[N-(2,6-dichlorophenyl)sulfamoyl]-1-cyclohexene-1-carboxylate (Compound 47; 0.05 g) as white crystals.

$^1$H-NMR (d$_6$-DMSO)δ: 1.03 (3H, t, J=7.0 Hz), 1.55–1.90 (2H, m), 2.03–2.64 (4H, m), 3.94–4.04 (2H, m), 4.65 (1H, d, J=5.6 Hz), 7.06 (1H, br), 7.32–7.40 (1H, m), 7.54–7.58 (2H, m), 9.77 (1H, s).

% Calculated for C$_{15}$H$_{17}$Cl$_2$NO$_4$S: C, 47.63; H, 4.53; N, 3.70

% Found: C, 47.76; H, 4.49; N, 3.54.

Example 45

By the procedure similar to that employed in Example 33, ethyl 2-chlorosulfonyl-1-cyclohexene-1-carboxylate (0.40 g) obtained in Reference Example 2 was reacted with 4-(1H-tetrazol-1-yl)aniline (0.33 g) to yield ethyl 6-[N-[4-(1H-tetrazol-1-yl)phenyl]sulfamoyl]-1-cyclohexene-1-carboxylate (Compound 48; 0.45 g) as white crystals.

$^1$H-NMR (d$_6$-DMSO)δ: 1.17 (3H, t, J=7.0 Hz), 1.56–1.83 (2H, m), 1.98–2.46 (4H, m), 3.99–4.16 (2H, m), 4.41 (1H, d, J=4.2 Hz), 7.17 (1H, br), 7.42 (2H, d, J=9.0 Hz), 7.85 (2H, d, J=9.0 Hz), 10.01 (1H, s), 10.45 (1H, s).

% Calculated for C$_{16}$H$_{19}$N$_5$O$_4$S: C, 50.92; H, 5.07; N, 18.56

% Found: C, 50.86; H, 5.12; N, 18.47.

Example 46

By the procedure similar to that employed in Example 33, ethyl 2-chlorosulfonyl-1-cyclohexene-1-carboxylate (0.39 g) obtained in Reference Example 2 was reacted with 4-(1H-1,2,3-triazol-1-yl)aniline (0.36 g) to yield ethyl 6-[N-[4-(1H-1,2,3-triazol-1-yl)phenyl]sulfamoyl]-1-cyclohexene-1-carboxylate (Compound 49; 0.41 g) as white crystals.

$^1$H-NMR (d$_6$-DMSO)δ: 1.17 (3H, t, J=7.0 Hz), 1.57–1.82 (2H, m), 1.98–2.41 (4H, m), 4.02–4.12 (2H, m), 4.40 (1H, d, J=4.6 Hz), 7.16 (1H, br), 7.40 (2H, d, J=8.8 Hz), 7.84 (2H, d, J=8.8 Hz), 7.93 (1H, s), 8.73 (1H, s), 10.34 (1H, s).

% Calculated for C$_{17}$H$_{20}$N$_4$O$_4$S: C, 54.24; H, 5.36; N, 14.88

% Found: C, 54.35; H, 5.37; N, 14.96.

Example 47

By the procedure similar to that employed in Example 33, ethyl 2-chlorosulfonyl-1-cyclohexene-1-carboxylate (0.37 g) obtained in Reference Example 2 was reacted with 2-trifluoromethylaniline (0.31 g) to yield ethyl 6-[N-(2-trifluoromethylphenyl)sulfamoyl]-1-cyclohexene-1-carboxylate (Compound 50; 0.17 g) as colorless oil.

$^1$H-NMR (d$_6$-DMSO)δ: 1.08 (3H, t, J=7.0 Hz), 1.54–1.87 (2H, m), 1.99–2.42 (4H, m), 4.03 (2H, q, J=7.0 Hz), 4.49 (1H, d, J=5.0 Hz), 7.15 (1H, br), 7.44–7.52 (1H, m), 7.64–7.70 (3H, m), 9.53 (1H, s).

MS(m/z); 378 (MH$^+$)

Example 48

By the procedure similar to that employed in Example 33, ethyl 2-chlorosulfonyl-1-cyclohexene-1-carboxylate (0.41 g) obtained in Reference Example 2 was reacted with methyl p-aminobenzoate (0.32 g) to yield ethyl 6-(N-(4-methoxycarbonylphenyl)sulfamoyl]-1-cyclohexene-1-carboxylate (Compound 51; 0.46 g) as white crystals.

¹H-NMR (d₆-DMSO)δ: 1.14 (3H, t, J=7.0 Hz), 1.56–1.85 (2H, m), 1.99–2.40 (4H, m), 3.83 (3H, s), 3.96–4.13 (2H, m), 4.42 (1H, d, J=2.2 Hz), 7.17 (1H, br), 7.31 (2H, d, J=8.8 Hz), 7.90 (2H, d, J=8.8 Hz), 10.54 (1H, s).

% Calculated for $C_{17}H_{21}NO_6S$: C, 55.57; H, 5.76; N, 3.81

% Found: C, 55.69; H, 5.61; N, 3.97.

Example 49

To a solution of sodium 6-[N-(2,4-difluorophenyl)sulfamoyl]-1-cyclohexene-1-carboxylate (80 mg) obtained in Reference Example 12 in N,N-dimethylformamide (1 ml), benzylbromide (50 mg) was added with ice-cooling, and the mixture was stirred at 0° C. for 4 hours and then at room temperature for 17 hours. The reaction mixture was poured onto water (20 ml) and extracted with ethyl acetate (20 ml). The ethyl acetate layer was washed with water (20 ml×2) and dried over anhydrous magnesium sulfate and the solvent was distilled off under reduced pressure. The residue was purified by chromatography on silica gel (eluent: ethyl acetate/hexane=1/4) and crystallized from diisopropyl ether to yield benzyl 6-[N-(2,4-difluorophenyl)sulfamoyl]-1-cyclohexene-1-carboxylate (Compound 52, 14 mg) as white powdery crystals.

¹H-NMR (d₆-DMSO)δ: 1.55–1.83 (2H, m), 1.98–2.44 (4H, m), 4.30 (1H, d, J=4.2 Hz), 5.00 (1H, d, J=13 Hz), 5.11 (1H, d, J=13 Hz), 6.93–7.04 (1H, m), 7.17 (1H, t, J=4 Hz), 7.24–7.51 (7H, m), 9.88 (1H, s).

% Calculated for $C_{20}H_{19}F_2NO_4S$: C, 58.96; H, 4.70; N, 3.44

% Found: C, 58.67; H, 4.70; N, 3.49.

Example 50

By the procedure similar to that employed in Example 33, ethyl 2-chlorosulfonyl-1-cyclohexene-1-carboxylate (0.4 g) obtained in Reference Example 2 was reacted with 4-[2,3-bis(t-butoxycarbonyl)guanidinomethyl]aniline (0.71 g) to yield ethyl 6-[N-[4-[2,3-bis(t-butoxycarbonyl)guanidinomethyl]phenyl]sulfamoyl]-1-cyclohexene-1-carboxylate (Compound 53; 492 mg) as a white powder.

¹H-NMR (d₆-DMSO)δ: 1.15 (3H, t, J=6.8 Hz), 1.40 (9H, s), 1.48 (9H, m), 1.50–1.64 (2H, m), 2.13–2.32 (4H, m), 3.97–4.19 (2H, m), 4.32 (1H, d, J=4.0 Hz), 4.46 (2H, d, J=5.4 Hz), 7.11 (1H, t, J=4.0 Hz), 7.21 (2H, d, J=9.2 Hz), 7.26 (2H, d, J=9.2 Hz), 8.60 (1H, t, J=5.4 Hz), 10.01 (1H, s), 11.52 (1H, s).

% Calculated for $C_{27}H_{40}N_4O_8S$: C, 55.84; H, 6.94; N, 9.65

% Found C, 55.52; H, 6.95; N, 9.42.

Example 51

By the procedure similar to that employed in Example 33, ethyl 2-chlorosulfonyl-1-cyclohexene-1-carboxylate (0.40 g) obtained in Reference Example 2 was reacted with methyl 3-chloro-4-aminobenzoate methylester (0.39 g) to yield ethyl 6-[N-(2-chloro-4-methoxycarbonylphenyl)sulfamoyl]-1-cyclohexene-1-carboxylate (Compound 54; 0.20 g) as white crystals.

¹H-NMR (d₆-DMSO)δ: 1.10 (3H, t, J=7.0 Hz), 1.56–1.85 (2H, m), 1.99–2.43 (4H, m), 3.86 (3H, s), 4.02 (2H, q, J=7.0 Hz), 4.44 (1H, d, J=4.0 Hz), 7.18 (1H, br), 7.71 (1H, d, J=8.4 Hz), 7.88 (1H, dd, J=8.4 Hz, 1.8 Hz), 7.97 (1H, J, J=1.8 Hz), 9.96 (1H, s).

% Calculated for $C_{17}H_{20}ClNO_6S$: C, 50.81; H, 5.02; N, 3.49

% Found: C, 50.79; H, 4.98; N, 3.45.

Example 52

By the procedure similar to that employed in Example 33, ethyl 2-chlorosulfonyl-1-cyclohexene-1-carboxylate (0.41 g) obtained in Reference Example 2 was reacted with 4-amino-3-chlorobenzonitrile (0.32 g) to yield ethyl 6-[N-(2-chloro-4-cyanophenyl)sulfamoyl]-1-cyclohexene-1-carboxylate (Compound 55; 0.16 g) as white crystals.

¹H-NMR (d₆-DMSO)δ: 1.12 (3H, t, J=7.0 Hz), 1.56–1.84 (2H, m), 1.95–2.42 (4H, m), 4.03 (2H, q, J=7.0 Hz), 4.46 (1H, d, J=4.8 Hz), 7.20 (1H, br), 7.70–7.84 (2H, m), 8.07 (1H, br), 10.09 (1H, s).

% Calculated for $C_{16}H_{17}ClN_2O_4S$: C, 52.10; H. 4.65; N, 7.60

% Found: C, 52.15; H, 4.62; N, 7.46.

Example 53

To a solution of sodium 6-[N-(2,4-difluorophenyl)sulfamoyl]-1-cyclohexene-1-carboxylate (100 mg) obtained in Reference Example 12 in N,N-dimethylformamide (2 ml), 2-bromoethanol (81 mg) was added with ice-cooling, and the mixture was stirred at room temperature for 72 hours. The reaction mixture was poured onto water (30 ml) and extracted with ethyl acetate (30 ml). The ethyl acetate layer was washed with 5% aqueous solution of sodium bicarbonate (30 ml) and saturated brine (30 ml) and dried over anhydrous magnesium sulfate and the solvent was distilled off under reduced pressure. The residue was purified by chromatography on silica gel (eluent: ethyl acetate/hexane=1/1) and crystallized from diisopropyl ether to yield 2-hydroxyethyl 6-[N-(2,4-difluorophenyl)sulfamoyl]-1-cyclohexene-1-carboxylate (Compound 56, 35 mg) as white powdery crystals.

¹H-NMR (d₆-DMSO)δ: 1.58–1.81 (2H, m), 2.00–2.42 (4H, m), 3.51 (2H, br), 4.00 (2H, t, J=5.0 Hz), 4.34 (1H, d, J=4.4 Hz), 4.77 (1H, br), 7.02–7.20 (2H, m), 7.26–7.37 (1H, m), 7.44–7.56 (1H, m), 9.82 (1H, br).

% Calculated for $C_{15}H_{17}F_2NO_5S$: C, 49.86; H, 4.74; N, 3.88

% Found: C, 49.65; H, 4.79; N, 3.94.

Example 54

By the procedure similar to that employed in Example 33, ethyl 2-chlorosulfonyl-1-cyclohexene-1-carboxylate (0.40 g) obtained in Reference Example 2 was reacted with 2-chloro-4-(1H-1,2,4-triazol-1-yl)aniline (0.37 g) to yield ethyl 6-[N-[2-fluoro-4-(IH-1,2,4-triazol-1-yl)phenyl)sulfamoyl]-1-cyclohexene-1-carboxylate (Compound 57; 0.33 g) as white crystals.

¹H-NMR (d₆-DMSO)δ: 1.08 (3H, t, J=7.0 Hz), 1.50–1.69 (2H, m), 1.86–2.44 (4H, m), 4.00 (2H, q, J=7.0 Hz), 4.32 (1H, d, J=4.4 Hz), 7.10 (1H, br), 7.38–7.47 (1H, m), 7.60 (1H, dd, J=9.2 Hz, 3.0 Hz), 7.70 (1H, dd, J=9.2 Hz, 5.4 Hz), 8.30 (1H, s), 8.99 (1H, s), 9.64 (1H, s).

% Calculated for $C_{17}H_{19}FN_4O_4S$: C, 51.77; H, 4.86; N, 14.20

% Found: C, 51.51; H, 5.01; N, 14.06.

Example 55

A solution of, ethyl 2-chlorosulfonyl-1-cyclopentene-1-carboxylate (0.14 g) obtained in Reference Example 3 in ethyl acetate (2 ml) was added to a mixture of 2,4-difluoroaniline (0.1 g), triethylamine (0.17ml) andethyl acetate (2ml) with ice-cooling, and the mixture was stirred at room temperature for 5 hours. The reaction mixture was diluted with ethyl acetate (30 ml) and washed with water (30 ml). The ethyl acetate layer was washed with 0.5 N HCl (30 ml×2) and saturated brine (30 ml) and dried over anhydrous sodium sulfate and then the solvent was distilled off. The residue was subjected to flash column chromatography on silica gel (eluent: ethyl acetate/hexane=1/5) and the solvent in the first effluent was distilled off to yield ethyl 2-[N-(2, 4-difluorophenyl)sulfamoyl]-1-cyclopentene-1-carboxylate (Compound 66, 16.2mg) as a brown oil. After distilling the solvent in the second effluent off, the residue was crystallized from diisopropyl ether to yield ethyl 5-[N-(2,4-difluorophenyl)sulfamoyl]-1-cyclopentene-1-carboxylate (Compound 58, 22.8 mg) as colorless powdery crystals.

Compound 58: $^1$H-NMR (d$_6$-DMSO)δ: 1.14 (3H, t, J=7.0 Hz), 2.26–2.74 (4H, m), 4.06 (2H, q, J=7.0 Hz), 4.50 (1H, d, J=8.0 Hz), 7.02–7.13 (2H, m), 7.24–7.52 (2H, m), 9.79 (1H, s).

% Calculated for $C_{14}H_{15}F_2NO_4S$: C, 50.75; H, 4.56; N, 4.23

% Found: C, 50.64; H, 4.51; N, 4.15.

Compound 66: $^1$H-NMR (CDCl$_3$)δ: 1.34 (3H, t, J=7.0 Hz), 1.93 (2H, quintet, J=7.6 Hz), 2.69–2.88 (4H, m), 4.32 (2H, q, J=7.0 Hz), 6.79–6.93 (2H, m), 7.50–7.62 (1H, m), 7.96 (1H, s).

Example 56

To a solution of sodium 6-[N-(2,4-difluorophenyl) sulfamoyl]-1-cyclohexene-1-carboxylate (112 mg) obtained in Reference Example 12 in N,N-dimethylformamide (2 ml), t-butyl bromoacetate (98 mg) was added with ice-cooling, and the mixture was stirred at room temperature for 43 hours. The reaction mixture was poured onto water (30 ml) and extracted with ethyl acetate (30 ml). The ethyl acetate layer was washed with water (30 ml) and dried over anhydrous magnesium sulfate and the solvent was distilled off under reduced pressure. The residue was purified by chromatography on silica gel (eluent: ethyl acetate/hexane=1/3) to yield t-butyl [6-[N-(2,4-difluorophenyl)sulfamoyl]-1-cyclohexen-1-yl]carbonyloxyacetate (Compound 59, 118 mg) as white powdery crystals.

$^1$H-NMR (d$_6$-DMSO)δ: 1.40 (9H, s), 1.59–1.85 (2H, m), 2.01–2.46 (4H, m), 4.30 (1H, d, J=5.0 Hz), 4.50 (2H, s), 7.04–7.14 (1H, m), 7.21–7.54 (3H, m), 9.84 (1H, s).

Example 57

To a solution of t-butyl [6-[N-(2,4-difluorophenyl) sulfamoyl]-1-cyclohexen-1-yl]carbonyloxyacetate (Compound 59, 80 mg) obtained in Example 56 in ethyl acetate (4 ml), a 4N solution of hydrogen chloride in ethyl acetate (5 ml) was added with ice-cooling and the mixture was stirred at room temperature for 70 hours. The reaction mixture was evaporated under reduced pressure to dryness and the residue was purified by ODS column chromatography (eluent: methanol/water=3/2) to yield [6-[N-(2,4-difluorophenyl)sulfamoyl]-1-cyclohexen-1-yl] carbonyloxyacetic acid (Compound 60, 25 mg) as white powdery crystals.

$^1$H-NMR (d$_6$-DMSO)δ: 1.60–1.82 (2H, m), 1.98–2.42 (4H, m), 4.32 (1H, d, J=4.4 Hz), 4.52 (2H, s), 7.03–7.13 (1H, m), 7.21–7.54 (3H, m), 10.02 (1H, br), 13.0 (1H, br).

SIMS: 375 (M$^+$).

Example 58

A solution of ethyl 2-chlorosulfonyl-1-cycloheptene-1-carboxylate (0.56 g) obtained in Reference Example 4 in ethyl acetate (3.5 ml) was added to a mixture of 2,4-difluoroaniline (0.35 g), triethylamine (0.42 ml) and ethyl acetate (2 ml) with ice-cooling, and the mixture was stirred at room temperature for 7 hours. The reaction mixture was diluted with ethyl acetate (30 ml) and washed with water (30 ml). The ethyl acetate layer was washed with 0.5 N HCl (30 ml×2) and saturated brine (30 ml) and dried over anhydrous sodium sulfate and then the solvent was distilled off. The residue was subjected to flash column chromatography on silica gel (eluent: ethyl acetate/hexane=1/8) and ODS column chromatography (eluent: acetonitrile/water=6/4) and then crystallized from hexane to yield ethyl 7-[N-(2,4-difluorophenyl)sulfamoyl]-1-cycloheptene-1-carboxylate (Compound 61, 25.7 mg) as colorless powdery crystals.

$^1$H-NMR (d$_6$-DMSO)δ: 1.12 (3H, t, J=7.0 Hz), 1.60–1.90 (3H, m), 2.02–2.73 (5H, m), 4.03 (2H, q, J=7.0 Hz), 4.74 (1H, t, J=4.0 Hz), 7.07 (1H, t, J=9.0 Hz), 7.26–7.35 (1H, m), 7.42–7.54 (2H, m), 9.84 (1H, s).

% Calculated for $C_{16}H_{19}F_2NO_4S$: C, 53.47; H, 5.33; N, 3.90

% Found: C, 53.52; H, 5.09; N, 3.93.

Example 59

By the procedure similar to that employed in Example 33, ethyl 2-chlorosulfonyl-1-cyclohexene-1-carboxylate (0.30 g) obtained in Reference Example 2 was reacted with t-butyl N-(4-amino-3-chlorobenzoyl)glycinate (0.41 g) to yield ethyl 6-[N-[2-chloro-4-(N-t-butoxycarbonylmethylcarbamoyl)phenyl]sulfamoyl]-1-cyclohexene-1-carboxylate (Compound 62; 0.18 g) as white crystals.

$^1$H-NMR (d$_6$-DMSO)δ: 1.10 (3H, t, J=7.0 Hz), 1.42 (9H, s), 1.55–1.86 (2H, m), 1.98–2.46 (4H, m), 3.90 (2H, d, J=5.8 Hz), 4.03 (2H, q, J=7.0 Hz), 4.41 (1H, d, J=4.2 Hz), 7.16 (1H, br), 7.65 (1H, d, J=8.4 Hz), 7.83 (1H, dd, J=8.4 Hz, 1.8 Hz), 7.98 (1H, d, J=1.8 Hz), 8.95 (1H, br), 9.89 (1H, s).

% Calculated for $C_{22}H_{29}Cl\,N_2O_7S$: C, 49.58; H, 4.44; N, 3.85

% Found: C, 49.51; H, 4.35; N, 3.76.

Example 60

Ethyl 6-[N-[2-chloro-4-(N-t-butoxycarbonylmethylcarbamoyl)phenyl]sulfamoyl]-1-cyclohexene-1-carboxylate (23 mg) was dissolved in ethyl acetate (0.5 ml) and then admixed with a 4N solution of hydrogen chloride in ethyl acetate (1.8 ml) and the mixture was stirred at room temperature for 51 hours. The reaction mixture was diluted with ethyl acetate and then washed twice with saturated brine. The ethyl acetate layer was dried over magnesium sulfate and the solvent was distilled off under reduced pressure. The residue was purified by column chromatography on silica gel (eluent: ethyl acetate/hexane= 11:14) to yield ethyl 6-[N-[2-chloro-4-(N-ethoxycarbonylmethylcarbamoyl)phenyl]sulfamoyl]-1-cyclohexene-1-carboxylate (Compound 63; 18 mg) as a colorless oil.

$^1$H-NMR (d$_6$-DMSO)δ: 1.10 (3H, t, J=7.0 Hz), 1.21 (3H, t, J=7.0 Hz), 1.57–1.84 (2H, m), 1.91–2.38 (4H, m), 3.98–4.08 (4H, m), 4.12 (2H, q, J=7.0 Hz), 4.41 (1H, d, J=4.4 Hz), 7.16 (1H, br), 7.66 (1H, d, J=8.5 Hz), 7.83 (1H, dd, J=8.5 Hz, 1.8 Hz), 7.99 (1H, d, J=1.8 Hz), 9.04 (1H, br), 9.89 (1H, s).

Example 61

By the procedure similar to that employed in Example 55, ethyl 2-chlorosulfonyl-1-cyclopentene-1-carboxylate (0.39 g) obtained in Reference Example 3 was reacted with 2-chloro-4-fluoroaniline (0.31 g) to yield ethyl 5-[N-(2-chloro-4-fluorophenyl)sulfamoyl]-1-cyclopentene-1-carboxylate (Compound 64, 134 mg) as pale yellow powdery crystals.

$^1$H-NMR (d$_6$-DMSO)δ: 1.15 (3H, t, J=7.0 Hz), 2.22–2.74 (4H, m), 4.07 (2H, q, J=7.0 Hz), 4.50 (1H, d, J=8.0 Hz), 7.10 (1H, s), 7.18–7.28 (1H, m), 7.47–7.56 (2H, m), 9.70 (1H, s).

% Calculated for C$_{14}$H$_{15}$ClFNO$_4$S: C, 48.35; H, 4.35; N, 4.03

% Found: C, 48.42; H, 4.07; N, 4.04.

Example 62

By the procedure similar to that employed in Example 33, ethyl 2-chlorosulfonyl-1-cyclohexene-1-carboxylate (0.41 g) obtained in Reference Example 2 was reacted with 4-(2,2,3,3,3-pentafluoropropoxy)aniline (0.87 g) to yield 2-[4-(2,2,3,3,3-pentafluoropropoxy)phenyl]-4,5,6,7-tetrahydro-1,2-benzisothiazol-3(2H)-one 1,1-dioxide (Compound 69; 0.09 g) as white crystals.

$^1$H-NMR (d$_6$-DMSO)δ: 1.69–1.91 (4H, m), 2.38–2.54 (4H, m), 4.92 (2H, t, J=7.4 Hz), 7.26 (2H, d, J=7.2 Hz), 7.38 (2H, d, J=7.2 Hz).

% Calculated for C$_{16}$H$_{14}$F$_5$NO$_4$S: C, 46.72; H, 3.43; N, 3.41

% Found: C, 46.79; H, 3.38; N, 3.29.

Example 63

By the procedure similar to that employed in Example 58, ethyl 2-chlorosulfonyl-1-cycloheptene-1-carboxylate (0.38 g) obtained in Reference Example 4 was reacted with 2-chloro-4-fluoroaniline (0.27 g) to yield ethyl 7-[N-(2-chloro-4-fluorophenyl)sulfamoyl]-1-cycloheptene-1-carboxylate (Compound 65, 19 mg) as pale yellow powdery crystals.

$^1$H-NMR (d$_6$-DMSO)δ: 1.23 (3H, t, J=7.0 Hz), 1.19–1.38 (1H, m), 1.67–1.81 (3H, m), 2.02–2.15 (1H, m), 2.15–2.76 (3H, m), 4.05 (2H, q, J=7.0 Hz), 4.80 (1H, t, J=4.6 Hz), 7.17–7.27 (1H, m), 7.44–7.59 (3H, m), 9.59 (1H, s).

% Calculated for C$_{16}$H$_{19}$ClFNO$_4$S: C, 51.13; H, 5.10; N, 3.73

% Found: C, 51.16; H, 5.19; N, 3.89.

Example 64

To a solution of N-methylmorpholine (41 mg) in N,N-dimethylformamide (1.5 ml), a solution of 6-[N-(2,4-difluorophenyl)sulfamoyl]-1-cyclohexene-1-carboxylic acid (64 mg) obtained in Reference Example 12 in N,N-dimethylformamide (1 ml) was added with ice-cooling. To this mixture, a solution of 1-hydroxybenzotriazole (41 mg) in N,N-dimethylformamide (0.5 ml) and dicyclohexylcarbodiimide (52 mg) were added and the mixture was stirred with ice-cooling for 1 hour and then at room temperature for 16 hours. The reaction mixture was combined with ethyl acetate (20 ml) and the insolubles were filtered off. The filtrate was washed successively with a 10% aqueous solution of phosphoric acid (20 ml), water (20 ml), a 5% aqueous solution of sodium bicarbonate (20 ml), water (20 ml) and then saturated brine (20 ml) and dried over anhydrous magnesium sulfate and the solvent was distilled off under reduced pressure. The residue was combined with ethyl acetate (3 ml) and the insolubles were filtered off. The filtrate was concentrated under reduced pressure and the residue was purified by chromatography on silica gel (eluent: ethyl acetate/hexane=1/2) and crystallized from diisopropyl ether to yield 2-(2,4-difluorophenyl)-5,6,7,7a-tetrahydro-1,2-benzoisothiazol-3(2H)-one 1,1-dioxide (Compound 70, 25 mg) as white powdery crystals.

$^1$H-NMR (d$_6$-DMSO)δ: 1.59–1.82 (2H, m), 1.98–2.06 (1H, m), 2.37–2.46 (3H, m), 4.84–4.91 (1H, m), 7.17–7.37 (2H, m), 7.49–7.65 (2H, m).

SIMS: 300 (MH$^+$)

Example 65

By the procedure similar to that employed in Example 33, ethyl 2-chlorosulfonyl-1-cyclohexene-1-carboxylate (11.8 g) obtained in Reference Example 2 was reacted with 2-chloro-4-fluoroaniline (8.84 g) to yield ethyl 6-[N-(2-chloro-4-fluorophenyl)sulfamoyl]-1-cyclohexene-1-carboxylate (Compound 29, 11.3g) as white crystals. This substance was identical physicochemically with Compound 29 obtained in Example 26.

Example 66

Ethyl 6-(N-(2-chloro-4-fluorophenyl)sulfamoyl]-1-cyclohexene-1-carboxylate (Compound 29, 2.01 g) obtained in Example 65 was resolved by high pressure liquid chromatography (CHIRALPAK AD; eluent: hexane/ethanol=9/1) into two optical isomers to yield 1-ethyl 6-[N-(2-chloro-4-fluorophenyl)sulfamoyl]-1-cyclohexene-1-carboxylate (Compound 71, 979 mg) and d-ethyl 6-[N-(2-chloro-4-fluorophenyl)sulfamoyl]-1-cyclohexene-1-carboxylate (Compound 72, 959 mg) as an oil, respectively.

Compound 71 (833 mg) was crystallized from a mixture of diisopropyl ether and hexane to obtain colorless prism-like crystals (681 mg) of Compound 71.

$^1$H-NMR (d$_6$-DMSO)δ: 1.05 (3H, t, J=7.0 Hz), 1.55–1.84 (2H, m), 1.96–2.43 (4H, m), 4.00 (2H, q, J=7.0 Hz), 4.29 (1H, d, J=5.0 Hz), 7.10 (1H, br), 7.20–7.30 (1H, m), 7.50–7.58 (2H, m), 9.73 (1H, s).

% Calculated for C$_{15}$H$_{17}$ClFNO$_4$S: C, 49.79; H, 4.74; N, 3.87

% Found: C, 49.55; H, 4.46; N, 4.08.

[α]$^{20}_D$ –111.0° (c=1.0, in methanol)

Compound 72 (817 mg) was crystallized from a mixture of diisopropyl ether and hexane to obtain colorless prism-like crystals (634 mg) of Compound 72.

$^1$H-NMR (d$_6$-DMSO)δ: 1.05 (3H, t, J=7.0 Hz), 1.56–1.83 (2H, m), 2.01–2.43 (4H, m), 4.00 (2H, q, J=7.0 Hz), 4.30 (1H, d, J=5.0 Hz), 7.10 (1H, br), 7.20–7.30 (1H; m), 7.50–7.58 (2H, m), 9.74 (1H, s).

% Calculated for C$_{15}$H$_{17}$ClFNO$_4$S: C, 49.79; H, 4.74; N, 3.87

% Found C, 49.67; H, 4.72; N, 3.85.

[α]$^{20}_D$ +111.0° (c=1.0, in methanol)

Example 67

By the procedure similar to that employed in Example 33, ethyl 2-chlorosulfonyl-1-cyclohexene-1-carboxylate (0.43 g) obtained in Reference Example 2 was reacted with 2-bromo-4-fluoroaniline (0.42 g) to yield ethyl 6-[N-(2-bromo-4-fluorophenyl)sulfamoyl]-1-cyclohexene-1-carboxylate (Compound 73; 0.36 g) as white crystals.

$^1$H-NMR (d$_6$-DMSO)δ: 1.05 (3H, t, J=7.0 Hz), 1.55–1.86 (2H, m), 1.99–2.45 (4H, m), 4.00 (2H, q, J=7.0 Hz), 4.33 (1H, d, J=5.2 Hz), 7.09 (1H, br), 7.24–7.34 (1H, m), 7.50–7.68 (2H, m), 9.64 (1H, s).

% Calculated for C$_{15}$H$_{17}$BrFNO$_4$S: C, 44.35; H, 4.22; N, 3.45

% Found: C, 44.27; H, 4.16; N, 3.73.

Example 68

By the procedure similar to that employed in Example 33, ethyl 2-chlorosulfonyl-1-cyclohexene-1-carboxylate (0.43 g) obtained in Reference Example 2 was reacted with 4-bromo-2-chloroaniline (0.45 g) to yield ethyl 6-[N-(4-bromo-2-chlorophenyl)sulfamoyl]-1-cyclohexene-1-carboxylate (Compound 74; 0.23 g) as white crystals.

$^1$H-NMR (d$_6$-DMSO)δ: 1.08 (3H, t, J=7.2 Hz), 1.45–1.83 (2H, m), 1.96–2.42 (4H, m), 4.01 (2H, q, J=7.2 Hz), 4.32 (1H, d, J=5.2 Hz), 7.12 (1H, br), 7.45–7.57 (2H, m), 7.76–7.78 (1H, m), 9.80 (1H, s).

% Calculated for C$_{15}$H$_{17}$BrClNO$_4$S: C, 42.62; H, 4.05; N, 3.31

% Found: C, 42.49; H, 3.99; N, 3.60.

Example 69

Ethyl 2-chlorosulfonyl-5-phenyl-1-cyclohexene-1-carboxylate (0.5 g) obtained in Reference Example 14 was added to a mixture of 2,4-difluoroaniline (0.26 g), triethylamine (0.42 ml) and ethyl acetate (3 ml) with ice-cooling, and the mixture was stirred at room temperature for 7 hours. The reaction mixture was diluted with ethyl acetate (30 ml) and washed with water (30 ml). The ethyl acetate layer was washed with 0.5 N HCl (30 ml) and saturated brine (30 ml) and dried over anhydrous sodium sulfate and then the solvent was distilled off. The residue was subjected to flash column chromatography on silica gel (eluent: ethyl acetate/hexane=1/10) and ODS flash column chromatography (eluent: methanol/water/acetic acid=7/3/0.02) to yield a more polar diastereomer (Compound 75, 56 mg, colorless powdery crystals) and a less polar diastereomer (Compound 76, 84 mg, colorless powdery crystals) of ethyl 6-[N-(2,4-difluorophenyl)sulfamoyl]-3-phenyl-1-cyclohexene-1-carboxylate.

More polar diastereomer (Compound 75): $^1$H-NMR (d$_6$-DMSO)δ: 1.08 (3H, t, J=7.2 Hz), 1.90–2.57 (4H, m), 3.54–3.70 (1H, m), 4.04 (2H, q, J=7.2 Hz), 4.36 (1H, brs), 6.96–7.59 (9H, m), 9.98 (1H, s).

% Calculated for C$_{21}$H$_{21}$F$_2$NO$_4$S: C, 59.85; H, 5.02; N, 3.32

% Found: C, 59.86; H, 5.03; N, 3.21.

Less polar diastereomer (Compound 76): $^1$H-NMR (CDCl$_3$)δ: 1.09 (3H, t, J=7.4 Hz), 1.55–1.61 (1H, m), 1.81–1.99 (1H, m), 2.28–2.34 (1H, m), 2.49–2.59 (1H, m), 3.72–3.84 (1H, m), 4.05 (2H, q, J=7.4 Hz), 4.43 (1H, d, J=5.0 Hz), 7.03–7.57 (9H, m), 9.94 (1H, s).

% Calculated for C$_{21}$H$_{21}$F$_2$NO$_4$S: C, 59.85; H, 5.02; N, 3.32

% Found: C, 59.96; H, 5.17; N, 3.17.

Example 70

By the procedure similar to that employed in Example 69, ethyl 2-chlorosulfonyl-5-phenyl-1-cyclohexene-1-carboxylate (0.5 g) obtained in Reference Example 14 was reacted with 2-chloro-4-fluoroaniline (0.29 g) to yield a more polar diastereomer (Compound 77, 89 mg, colorless powdery crystals) and a less polar diastereomer (Compound 78, 51 mg, colorless powdery crystals) of ethyl 6-[N-(2-chloro-4-fluorophenyl)sulfamoyl]-3-phenyl-1-cyclohexene-1-carboxylate.

More polar diastereomer (Compound 77): $^1$H-NMR (d$_6$-DMSO)δ: 1.06 (3H, t, J=7.0 Hz), 1.88–2.26 (3H, m), 2.49–2.63 (1H, m), 3.58–3.67 (1H, m), 4.04 (2H, q, J=7.0 Hz), 4.0 (1H, d, J=3.6 Hz), 6.97 (1H, d, J=2.6 Hz), 7.22–7.41 (6H, m), 7.51–7.63 (2H, m), 9.85 (1H, s).

% Calculated for C$_{21}$H$_{21}$ClFNO$_4$S: C, 57.60; H, 4.83; N, 3.20

% Found: C, 57.60; H, 4.87; N, 3.06.

Less polar diastereomer (Compound 78): $^1$H-NMR (CDCl$_3$)δ: 1.08 (3H, t, J=7.2 Hz), 1.54–1.63 (1H, m), 1.81–1.98 (1H, m), 2.30–2.65 (2H, m), 3.77–3.79 (1H, m), 4.05 (2H, q, J=7.2 Hz), 4.44 (1H, d, J=4.8 Hz), 7.05–7.61 (9H, m), 9.83 (1H, s).

% Calculated for C$_{21}$H$_{21}$ClFNO$_4$S: C, 57.60; H, 4.83; N, 3.20

% Found C, 57.57; H, 4.86; N, 3.07.

Example 71

2,4-Difluoroaniline (0.39 g) was dissolved in ethyl acetate (5ml) and the resultant solution was admixed with triethylamine (0.65 ml) with ice-cooling, and then treated dropwise with a solution of ethyl 5-t-butyl-2-chlorosulfonyl-1-cyclohexene-1-carboxylate (0.72 g) obtained in Reference Example 16 in ethyl acetate (9 ml). The reaction mixture was stirred under nitrogen flow at 0° C. for 30 minutes then at room temperature for 46 hours. The reaction mixture was diluted with ethyl acetate, and washed successively with water (80 ml), 0.5 N HCl (80 ml), water (80 ml×2) and saturated brine (80 ml). The ethyl acetate layer was dried over magnesium sulfate and the solvent was distilled off under reduced pressure. The residue was subjected to column chromatography on silica gel (eluent: ethyl acetate/hexane=1/7→1/6) and desired fractions were concentrated under reduced pressure. The residue was subjected to medium-pressure ODS chromatography (eluent: methanol/water=6/4) and then to high pressure liquid chromatography (YMC-Pack, ODS, eluent: acetonitrile/water=55/45→60/40) to isolate a more polar compound and a less polar compound separately. Each desired fraction was concentrated under reduced pressure and the residue was extracted with ethyl acetate and then washed with water and saturated brine. The ethyl acetate layer was dried over magnesium sulfate and the residue was crystallized from a mixture of ethyl acetate and hexane to yield a more polar diastereomer (Compound 79; 0.08 g) and a less polar diastereomer (Compound 80; 0.03) of ethyl 6-[N-(2,4-difluorophenyl)sulfamoyl]-3-t-butyl-1-cyclohexene-1-carboxylate each as white crystals.

More polar diastereomer (Compound 79): $^1$H-NMR (d$_6$-DMSO)δ: 0.91 (9H, s), 1.10 (3H, t, J=7.2 Hz), 1.35–1.51 (1H, m), 1.90–2.30 (4H, m), 4.04 (2H, q, J=7.2 Hz), 4.40 (1H, d, J=4.6 Hz), 7.02–7.14 (1H, m), 7.13 (1H, br), 7.41–7.53 (2H, m), 9.85 (1H, s).

% Calculated for C$_{19}$H$_{25}$F$_2$NO$_4$S: C, 56.84; H, 6.28; N, 3.49

% Found: C, 56.77; H, 6.04; N, 3.64.

Less polar diastereomer (Compound 80): $^1$H-NMR (d$_6$-DMSO)δ: 0.93 (9H, s), 1.07 (3H, t, J=7.0 Hz), 1.58–2.43 (5H, m), 4.02 (2H, q, J=7.0 Hz), 4.24 (1H, d, J=4.8 Hz), 7.03–7.12 (1H, m), 7.11 (1H, br), 7.27–7.55 (2H, m), 9.86 (1H, s).

% Calculated for C$_{17}$H$_{21}$F$_2$NO$_4$S: C, 56.84; H, 6.28; N, 3.49

% Found: C, 56.75; H, 6.15; N, 3.66.

Example 72

By the procedure similar to that employed in Example 71, ethyl 5-t-butyl-2-chlorosulfonyl-1-cyclohexene-1-carboxylate (0.74 g) obtained in Reference Example 16 was reacted with 2-chloro-4-fluoroaniline (0.45 g) to yield a more polar diastereomer (Compound 81; 0.04 g) and a less polar diastereomer (Compound 82; 0.02 g) of ethyl 6-[N-(2-chloro-4-fluorophenyl)sulfamoyl]-3-t-butyl-1-cyclohexene-1-carboxylate each as white crystals.

More polar diastereomer (Compound 81): $^1$H-NMR ($d_6$-DMSO)δ: 0.91 (9H, s), 1.08 (3H, t, J=7.0 Hz), 1.38–1.53 (1H, m), 1.92–2.31 (4H, m), 4.04 (2H, q, J=7.0 Hz), 4.41 (1H, d, J=6.6 Hz), 7.14 (1H, br), 7.19–7.27 (1H, m), 7.48–7.57 (2H, m), 9.73 (1H, s).

% Calculated for $C_{19}H_{25}ClFNO_4S$: C, 54.60; H, 6.03; N, 3.35

% Found: C, 54.35; H, 5.89; N, 3.51.

Less polar diastereomer (Compound 82): $^1$H-NMR ($d_6$-DMSO)δ: 0.92 (9H, s), 1.05 (3H, t, J=7.0 Hz), 1.59–2.55 (5H, m), 4.00 (2H, q, J=7.0 Hz), 4.26 (1H, d, J=4.6 Hz), 7.10 (1H, br), 7.20–7.30 (1H, m), 7.49–7.58 (2H, m), 9.73 (1H, s).

% Calculated for $C_{19}H_{25}ClFNO_4S$: C, 54.60; H, 6.03; N, 3.35

% Found: C, 54.42; H, 5.99; N, 3.38.

Example 73

2,4-Difluoroaniline (1.51 g) was dissolved in ethyl acetate (33 ml) and the resultant solution was admixed with triethylamine (2.51 ml) with ice-cooling, and then treated dropwise with a solution of ethyl 2-chlorosulfonyl-5,5-dimethyl-1-cyclohexene-1-carboxylate (2.53 g) obtained in Reference Example 18 in ethyl acetate (17 ml). The reaction mixture was stirred under nitrogen flow at 0° C. for 30 minutes then at room temperature for 64.5 hours. The reaction mixture was diluted with ethyl acetate, and washed successively with water (120 ml), 0.5 N HCl (120 ml), water (120 ml×2) and saturated brine (120 ml). The ethyl acetate layer was dried over magnesium sulfate and the solvent was distilled off under reduced pressure. The residue was purified by column chromatography on silica gel (eluent: ethyl acetate/hexane= 1/9→1/7). A desired fraction was concentrated under reduced pressure, and the residue was crystallized from a mixture of ethyl acetate and diisopropyl ether to yield ethyl 6-[N-(2,4-difluorophenyl)sulfamoyl]-3,3-dimethyl-1-cyclohexene-1-carboxylate (Compound 83; 0.83 g) as white crystals.

$^1$H-NMR ($d_6$-DMSO)δ: 0.99 (3H, s), 1.08 (3H, t, J-7.0 Hz), 1.08 (3H, s), 1.39–1.45 (1H, m), 1.88–2.12 (2H, m), 2.30–2.37 (1H, m), 4.01 (2H, q, J=7.0 Hz), 4.23 (1H, d, J=4.4 Hz), 6.79 (1H, s5, 7.04–7.08 (1H, m), 7.12–7.36 (1H, m), 7.42–7.54 (1H, m), 9.88 (1H, s).

% Calculated for $C_{17}H_{21}F_2No_4S$: C, 54.68; H, 5.67; N, 3.75

% Found: C, 54.59; H, 5.72; N, 3.72.

Example 74

By the procedure similar to that employed in Example 73, ethyl 2-chlorosulfonyl-5,5-dimethyl-1-cyclohexene-1-carboxylate (0.62 g) obtained in Reference Example 18 was reacted with 2-chloro-4-fluoroaniline (0.42 g) to yield ethyl 6-[N-(2-chloro-4-fluorophenyl)sulfamoyl]-3,3-dimethyl-1-cyclohexene-1-carboxylate (Compound 84; 0.13 g) as white crystals.

$^1$H-NMR ($d_6$-DMSO)δ: 0.99 (3H, s), 1.05 (3H, t, J=7.0 Hz), 1.08 (3H, s), 1.40–1.45 (1H, m), 1.90–2.11 (2H, m), 2.36–2.43 (1H, m), 4.00 (2H, q, J=7.0 Hz), 4.24 (1H, d, J=4.4 Hz), 6.79 (1H, s), 7.20–7.30 (1H, m), 7.50–7.57 (2H, m), 9.77 (1H, s).

% Calculated for $C_{17}H_{21}ClFNO_4S$: C, 52.37; H, 5.43; N, 3.59

% Found: C, 52.30; H, 5.28; N, 3.62.

Example 75

To a solution -of ethyl 6-(N-(2,4-difluorophenyl)sulfamoyl]-1-cyclohexene-1-carboxylate (100 mg) obtained in Example 3 in chlorobenzene (2 ml), N-bromosuccinimide (56.7 mg) and 2,2'-azobisisobutyronitrile (0.5 mg) were added and the mixture was stirred at 90° C. for 7 hours. The reaction mixture was combined with an ice-water (20 ml), extracted with ethyl acetate (20 ml), washed with saturated brine (20 ml) and dried over anhydrous sodium sulfate. The solvent was distilled off and the resultant residue was purified by flash column chromatography on silica gel (eluent: ethyl acetate/hexane=1/20→ethyl acetate/hexane= 1/10) and crystallized from hexane to yield ethyl 3-bromo-6-[N-(2,4-difluorophenyl)sulfamoyl]-1-cyclohexene-1-carboxylate (Compound 85, 27 mg) as colorless powdery crystals.

$^1$H-NMR ($d_6$-DMSO)δ: 1.04 (3H, t, J=7.0 Hz), 2.03–2.20 (2H, m), 2.42–2.77 (2H, m), 4.05 (2H, q, J=7.0 Hz), 4.42 (1H, d, J=5.4 Hz), 5.32 (1H, t, J=4.0 Hz), 7.07 (1H, d, J=4.8 Hz), 7.06–7.16 (1H, m), 7.31–7.55 (2H, m), 10.07 (1H, s).

% Calculated for $C_{15}H_{16}BrF_2NO_4S$: C, 42.46; H, 3.80; N, 3.30

% Found: C, 42.4.

While typical examples of an inventive compound are shown in Table 1 to Table 5, which are not intended to restrict the inventive compounds.

TABLE 1

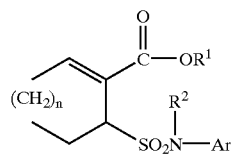

| Compound No. | R$^1$ | R$^2$ | Ar | n |
|---|---|---|---|---|
| 1 | C$_2$H$_5$ | H | 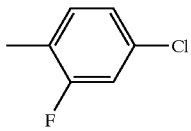 | 2 |

TABLE 1-continued
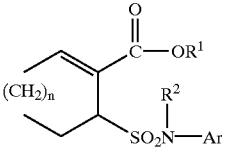
| Compound No. | R¹ | R² | Ar | n |
|---|---|---|---|---|
| 2 | $C_2H_5$ | $CH_3$ | 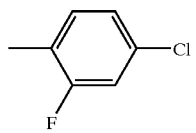 | 2 |
| 3 | $C_2H_5$ | H | 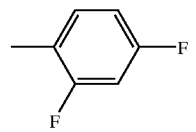 | 2 |
| 4 | $C_2H_5$ | H | 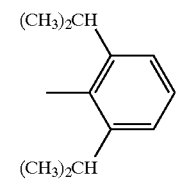 | 2 |
| 5 | $C_2H_5$ | H | 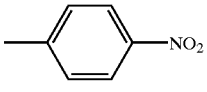 | 2 |
| 6 | $C_2H_5$ | H | 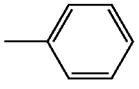 | 2 |
| 10 | $C_2H_5$ | H | 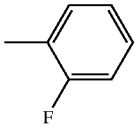 | 2 |
| 11 | $C_2H_5$ | H | 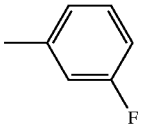 | 2 |
| 12 | $C_2H_5$ | H | 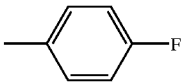 | 2 |
| 13 | $C_2H_5$ | H | 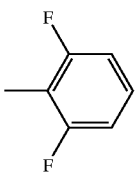 | 2 |
| 14 | $C_2H_5$ | H | 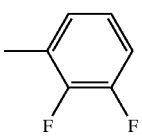 | 2 |

TABLE 1-continued
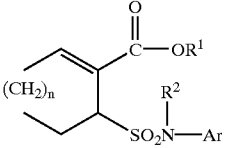
| Compound No. | R¹ | R² | Ar | n |
|---|---|---|---|---|
| 15 | $C_2H_5$ | H | 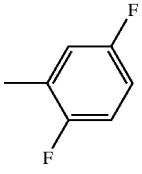 | 2 |
| 16 | $C_2H_5$ | H | 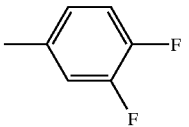 | 2 |
| 17 | $C_2H_5$ | H | 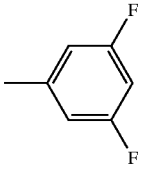 | 2 |
| 19 (l-体) | $C_2H_5$ | H | 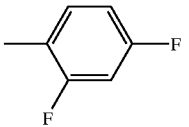 | 2 |
| 20 (d-体) | $C_2H_5$ | H | 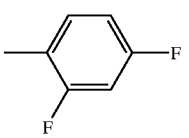 | 2 |
| 21 | $C_2H_5$ | H | 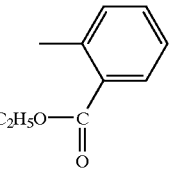 | 2 |
| 22 | $CH_3$ | H | 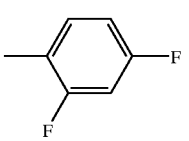 | 2 |
| 23 | $(CH_2)_2CH_3$ | H | 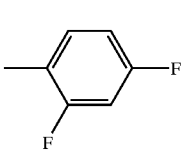 | 2 |

TABLE 1-continued
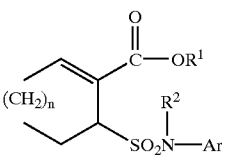
| Compound No. | R¹ | R² | Ar | n |
|---|---|---|---|---|
| 24 | CH₃ | H | 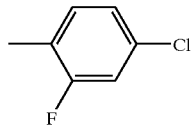 | 2 |
| 25 | CH(CH₃)₂ | H | 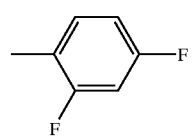 | 2 |
| 26 | C₂H₅ | H | 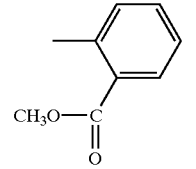 | 2 |
| 27 | C₂H₅ | H | 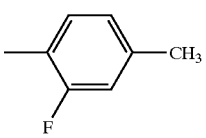 | 2 |
| 28 | C₂H₅ | H | 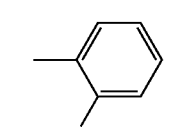 | 2 |
| 29 | C₂H₅ | H | 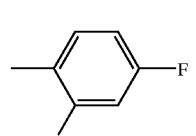 | 2 |
| 30 | C₂H₅ | H | 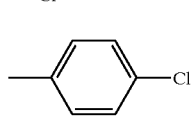 | 2 |
| 31 | C₂H₅ | H | 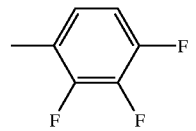 | 2 |
| 32 | CH₂CH(CH₃)₂ | H | 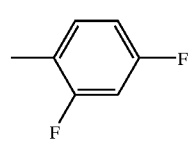 | 2 |

TABLE 1-continued

[Structure: ethyl group and (CH₂)ₙ group attached to a carbon bearing C(=O)OR¹, connected to CH-CH₂ bearing SO₂N(R²)-Ar]

| Compound No. | R¹ | R² | Ar | n |
|---|---|---|---|---|
| 33 | (CH₂)₃CH₃ | H | 2,4-difluorophenyl (2,5-substituted with F, F) | 2 |
| 34 | C₂H₅ | H | 4-bromo-2-fluorophenyl | 2 |
| 35 | C₂H₅ | H | 2,4-dichlorophenyl | 2 |
| 36 | C₂H₅ | H | 2-acetylphenyl (CH₃-C(=O)-) | 2 |
| 37 | C₂H₅ | H | 3-chlorophenyl | 2 |
| 38 | C₂H₅ | H | 2,3-dichlorophenyl | 2 |
| 39 | C₂H₅ | H | 2-ethylphenyl (C₂H₅) | 2 |
| 40 | C₂H₅ | H | 4-(2H-1,2,3-triazol-2-yl)phenyl | 2 |
| 41 | C₂H₅ | H | 2,5-dichlorophenyl | 2 |

TABLE 1-continued
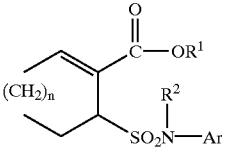
| Compound No. | R¹ | R² | Ar | n |
|---|---|---|---|---|
| 42 | C₂H₅ | H | 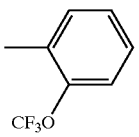 | 2 |
| 43 | C₂H₅ | H | 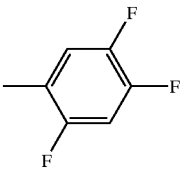 | 2 |
| 44 | C₂H₅ | H | 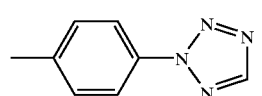 | 2 |
| 45 | C₂H₅ | H | 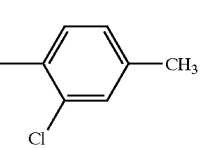 | 2 |
| 46 | C₂H₅ | H | 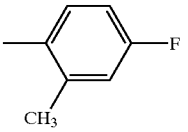 | 2 |
| 47 | C₂H₅ | H | 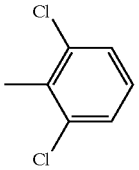 | 2 |
| 48 | C₂H₅ | H | 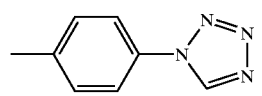 | 2 |
| 49 | C₂H₅ | H | 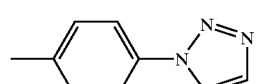 | 2 |
| 50 | C₂H₅ | H | 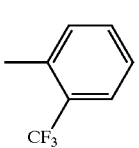 | 2 |
| 51 | C₂H₅ | H | 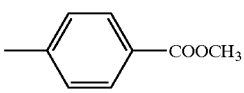 | 2 |

TABLE 1-continued
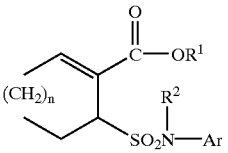
| Compound No. | R¹ | R² | Ar | n |
|---|---|---|---|---|
| 52 | CH₂–C₆H₅ | H | 2,4-difluoro-methylphenyl | 2 |
| 53 | C₂H₅ | H | 4-methylbenzyl-NH-C(=N-COOC(CH₃)₃)-NH-COOC(CH₃)₃ | 2 |
| 54 | C₂H₅ | H | 4-methyl-3-chloro-phenyl-COOCH₃ | 2 |
| 55 | C₂H₅ | H | 4-methyl-3-chloro-phenyl-CN | 2 |
| 56 | (CH₂)₂OH | H | 2,4-difluoro-methylphenyl | 2 |
| 57 | C₂H₅ | H | 4-methyl-3-fluoro-phenyl-(1,2,4-triazol-1-yl) | 2 |
| 58 | C₂H₅ | H | 2,4-difluoro-methylphenyl | 1 |
| 59 | CH₂COOC(CH₃)₃ | H | 2,4-difluoro-methylphenyl | 2 |
| 60 | CH₂COOH | H | 2,4-difluoro-methylphenyl | 2 |

TABLE 1-continued
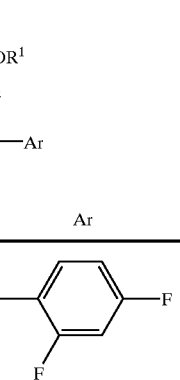
| Compound No. | R¹ | R² | Ar | n |
|---|---|---|---|---|
| 61 | $C_2H_5$ | H | 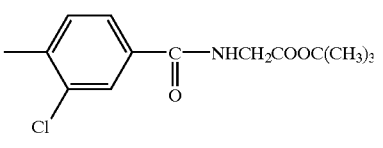 | 3 |
| 62 | $C_2H_5$ | H | 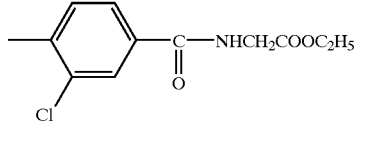 | 2 |
| 63 | $C_2H_5$ | H | 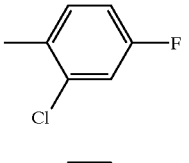 | 2 |
| 64 | $C_2H_5$ | H | 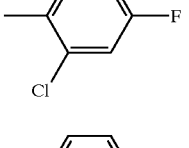 | 1 |
| 65 | $C_2H_5$ | H | 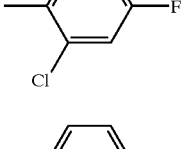 | 3 |
| 71 (l-type) | $C_2H_5$ | H | 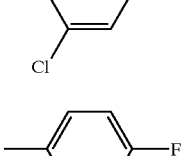 | 2 |
| 72 (d-type) | $C_2H_5$ | H | 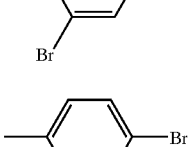 | 2 |
| 73 | $C_2H_5$ | H |  | 2 |
| 74 | $C_2H_5$ | H |  | 2 |

TABLE 2

Structure: ethyl-substituted acrylate with (CH$_2$)$_n$ ring and SO$_2$NH—Ar group, CO—OR$^1$

| Compound No. | R$^1$ | Ar | n |
|---|---|---|---|
| 7 | C$_2$H$_5$ | phenyl | 2 |
| 8 | C$_2$H$_5$ | 4-OCH$_3$-phenyl | 2 |
| 9 | C$_2$H$_5$ | 2-F,4-Cl-phenyl | 2 |
| 18 | C$_2$H$_5$ | 4-F-phenyl | 2 |
| 66 | C$_2$H$_5$ | 2,4-diF-phenyl | 1 |

TABLE 3

Structure: benzisothiazolone fused with cyclohexene ring (N—Ar, SO$_2$)

| Compound No. | Ar |
|---|---|
| 67 | 4-OCH$_3$-phenyl |
| 68 | 4-F-phenyl |
| 69 | 4-OCH$_2$CF$_2$CF$_3$-phenyl |

TABLE 3-continued

| Compound No. | Ar |
|---|---|
| 70 | 2,4-diF-phenyl |

TABLE 4

Structure: cyclohexene with R* substituent, CO—OR$^1$, and SO$_2$N(R$^2$)—Ar group

| Compound No. | R$^1$ | R$^2$ | R* | Ar |
|---|---|---|---|---|
| 75 (more polar diastereomer) | C$_2$H$_5$ | H | | 2,4-diF-phenyl |
| 76 (less polar diastereomer) | C$_2$H$_5$ | H | | 2,4-diF-phenyl |
| 77 (more polar diastereomer) | C$_2$H$_5$ | H | | 2-Cl,4-F-phenyl |
| 78 (less polar diastereomer) | C$_2$H$_5$ | H | | 2-Cl,4-F-phenyl |
| 79 (more polar diastereomer) | C$_2$H$_5$ | H | C(CH$_3$)$_3$ | 2,4-diF-phenyl |
| 80 (less polar diastereomer) | C$_2$H$_5$ | H | C(CH$_3$)$_3$ | 2,4-diF-phenyl |

TABLE 4-continued

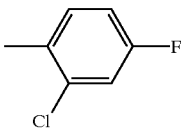

| Compound No. | R¹ | R² | R* | Ar |
|---|---|---|---|---|
| 81 (more polar diastereomer) | $C_2H_5$ | H | $C(CH_3)_3$ | 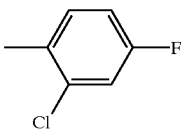 3-Cl, 4-F phenyl |
| 82 (less polar diastereomer) | $C_2H_5$ | H | $C(CH_3)_3$ | 3-Cl, 4-F phenyl |
| 85 | $C_2H_5$ | H | Br | 3-F, 4-F phenyl |

TABLE 5

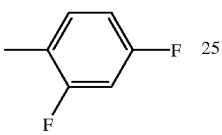

| Compound No. | Ar |
|---|---|
| 83 | 3-F, 4-F phenyl |
| 84 | 3-Cl, 4-F phenyl |

Experiment 1 NO Production-inhibiting Effect

Mouse macrophage cell line RAW264.7 was used as an iNOS-inducible cell and a test compound was examined for its % inhibition of NO production. The test compound was dissolved at 10 mM in N,N-dimethylformamide and diluted with an RPMI-1640 medium at the concentration of 0.1 mM. The concentration was further adjusted using the medium so that a final concentration ranging from 10 $\mu$M to 10 nM could be obtained by a 10-fold serial dilution and the test compound was added to a culture medium. On the day before the experiment, the cell was adjusted at $5 \times 10^5$/ml in an RPMI-1640 medium supplemented with 10% inactivated fetal calf serum and inoculated to a 96-well microplate at $1 \times 10^5$ cells/0.2 ml per well. After incubating at 37° C. under an atmosphere of 5% $CO_2$/95% air overnight, the test compound adjusted as described above was added and then LPS and interferon gamma were added at the final concentrations of 5 ng/ml and 1 U/ml, respectively. After further incubating overnight, culture supernatants were examined for the concentration of nitrite ion (stable metabolite of NO) which was used as an index for the NO production. The nitrite ion concentration was determined by adding 25 $\mu$l of 20 $\mu$g/ml of 2,3-diaminonaphthalene (DAN) to 50 $\mu$l of the culture supernatant, followed by incubating at room temperature for 10 minutes, followed by adding 25 $\mu$l of 0.5 N NaOH, followed by determining a fluorescence at 450 nm (excitation wavelength: 365 nm). The results are shown in Table 6. An $IC_{50}$ represents the concentration of the test compound which inhibits 50% of the NO production.

TABLE 6

| Compound No. | $IC_{50}$ ($\mu$M) |
|---|---|
| 1 | 0.12–0.32 |
| 2 | 1.1 |
| 3 | 0.013–0.039 |
| 4 | 2.6 |
| 5 | 3.7 |
| 6 | 0.59 |
| 7 | 4.0 |
| 8 | 4.8 |
| 9 | 4.1 |
| 10 | 0.058 |
| 11 | 0.31 |
| 12 | 0.18 |
| 13 | 0.46 |
| 14 | 0.59 |
| 15 | 0.28 |
| 16 | 0.18 |
| 17 | 2.6 |
| 18 | 4.4 |
| 19 | 2.0 |
| 20 | 0.005 |
| 21 | 2.4 |
| 22 | 0.18 |
| 23 | 0.027 |
| 24 | 0.78 |
| 25 | 0.32 |
| 26 | 3.3 |
| 27 | 0.25 |
| 28 | 0.029 |
| 29 | 0.0093 |
| 30 | 0.54 |
| 31 | 0.23 |
| 32 | 0.23 |
| 33 | 0.26 |
| 34 | 0.35 |
| 35 | 0.082 |
| 36 | 1.5 |
| 37 | 0.13 |
| 38 | 0.041 |
| 39 | 0.32 |
| 40 | 2.5 |
| 41 | 0.24 |
| 42 | 1.1 |
| 43 | 0.073 |
| 44 | 3.7 |
| 45 | 0.027 |
| 46 | 0.054 |
| 47 | 0.048 |
| 48 | 3.8 |
| 49 | 5.6 |
| 50 | 2.0 |
| 51 | 4.0 |
| 52 | 4.3 |
| 53 | 2.4 |
| 54 | 2.3 |
| 55 | 3.3 |
| 56 | 1.0 |
| 57 | 4.6 |
| 58 | 0.39 |
| 59 | 0.54 |

TABLE 6-continued

| Compound No. | IC$_{50}$ ($\mu$M) |
|---|---|
| 60 | 7.9 |
| 61 | 2.8 |
| 62 | 3.8 |
| 63 | 8.4 |
| 64 | 0.25 |
| 65 | 0.32 |
| 66 | 8.1 |
| 67 | 6.0 |
| 68 | 5.1 |
| 69 | 6.8 |
| 70 | 0.35 |

In Table 6, Compounds 1 and 9 were tested 7 and 9 times, respectively, and the minimum and the maximum of the IC$_{50}$ were indicated.

Any of the test compounds exhibited a potent inhibitory effect on the NO production by RAW264.7 cell, revealing that an inventive oxazole derivative had an excellent NO production-inhibiting effect.

Experiment 2 Cytokine Production-inhibiting Effect

Using mouse macrophage cell line RAW264.7, a test compound was examined for its % inhibition of a cytokine production. The test compound was dissolved at 10 mM in N,N-dimethylformamide and dilutedwith an RPMI-1640 medium at the concentration of 0.1 mM. The concentration was further adjusted using the medium so that a final concentration ranging from 10 $\mu$M to 10 nM could be obtained by a 10-fold serial dilution and the test compound was added to a culture medium. On the day before the experiment, the cell was adjusted at 5×10$^5$/ml in an RPMI-1640 medium supplemented with 10% inactivated fetal calf serum and inoculated to a 96-well microplate at 1×10$^5$ cells/0.2 ml per well. After incubating at 37° C. under an atmosphere of 5% CO$_2$/95% air overnight, the test compound adjusted as described above was added and then LPS and interferon-gamma were added at the final concentrations of 5 ng/ml and 1 U/ml, respectively. After further incubating overnight, culture supernatants were examined for the concentrations of TNF-α and IL-6. IL-1α was determined using 1.0 $\mu$g/ml of LPS in the absence of interferon gamma under otherwise similar conditions. Each cytokine was determined using an assay kit manufactured by Amersham. The results are shown in Table 7. An IC$_{50}$ represents the concentration of the test compound which inhibits 50% of the cytokine production.

TABLE 7

| Compound | IC$_{50}$ ($\mu$M) | | |
|---|---|---|---|
| No. | TNF-α | IL-1α | IL-6 |
| 1 | 0.20 | 0.39 | 0.061 |
|  | 0.53 |  | 0.014 |

In Table 7, TNF-α and IL-6 were tested twice and each IC$_{50}$ was indicated.

Experiment 3 Effect on Increase in Blood Nitric Oxide Level

When NO is produced in vivo as a result of a defense mechanism against infection or immune abnormality, it is readily metabolized to nitrous acid or nitric acid, resulting in an increase in blood nitric oxide concentration (NOx). Accordingly, an experimental animal was used to examine the effect of test compounds on the increase in the blood NOx level.

Famale BALB/c mice (6 weeks old) were purchased and acclimatized for 1 week and assigned to the groups in each of which 6 to 8 animals were included. In a treatment group, 30 mg/kg of a test compound suspended in a 0.5% aqueous solution of methyl cellulose was given orally. In a control group, the vehicle was given similarly. After 1 hour, LPS (10 mg/kg) was given intraperitoneally to each animals in the treatment and control groups, and the blood was taken 6 hours after the LPS administration and examined for the serum concentration of nitrite ion+nitrate ion. The nitrate ion was converted into the nitrite ion using a nitrate reductase, and the measured values, which was obtained by the fluorescent method using DAN described above, were represented as the total nitrite ion concentration. A% inhibition in a treatment group when compared with the control group is shown in Table 8.

TABLE 8

| Compound No. | Inhibition % of NO in blood |
|---|---|
| 1 | 76 |
| 3 | 90 |

Experiment 4 Effect on Increase in Blood Cytokine Level

As a result of a defense mechanism against an infection or an immune abnormality, various in vivo cytokines are produced. Accordingly, an experimental animal model was used to examine the effect of a test compound on the increase in the blood cytokine level.

Female BALB/c mice (6 weeks old) were purchased and acclimatized for 1 week and assigned to the groups in each of which 6 to 8 animals were included. In a treatment group, 30 mg/kg of a test compound suspended in a 0.5% aqueous solution of methyl cellulose was given orally. In a control group, the vehicle was given similarly. After 1 hour, LPS (10 mg/kg) was given intraperitoneally to each animal in the treatment and control groups, and the blood was taken 1 hour after the LPS administration and examined for the serum concentrations of TNF-α. IL-1α, IL-1β and IL-6 concentrations were determined using the serum from the blood taken 6 hours after the LPS administration. A% inhibition in a treatment group when compared with the control group is shown in Table 9. Each cytokine was determined using an assay kit manufactured by Amersham.

TABLE 9

| Compound | Inhibition % of cytokine in blood | | | |
|---|---|---|---|---|
| No. | TNF-α | IL-1α | IL-1β | IL-6 |
| 1 | 98 | 97 | 73 | 89 |

As evident from Tables 6 to 9, Compound (Ie) has an excellent inhibitory effect on NO production, inhibitory effect on cytokine production, inhibitory effect on the increase of nitric oxide concentration in blood and inhibitory effect on the increase of cytokine concentration.

The compound numbers in Tables 6 to 9 correspond to the compound numbers in Tables 1 to 5.

Industrial Applicability

An inventive Compound (Iaa) and Compound (Ie) have nitric oxide (NO) production-inhibiting effect and cytokine production-inhibiting effect, and are useful as a prophylactic and therapeutic agent against the diseases including cardiac diseases, autoimmune diseases, inflammatory diseases, central nervous system diseases, infectious diseases, sepsis, septic shock and the like.

What is claimed is:

1. A compound represented by the formula:

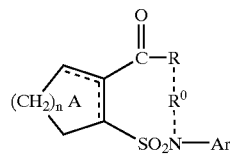
(Iaa)

wherein R represents an aliphatic hydrocarbon group optionally having substituents, an aromatic hydrocarbon group optionally having substituents, a heterocyclic group optionally having substituents, a group represented by the formula: $OR^1$ wherein $R^1$ represents a hydrogen atom or an aliphatic hydrocarbon group optionally having substituents or a group represented by the formula:

wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, ring A is a cycloalkene substituted by 1 to 4 substituents selected from
(i) an aliphatic hydrocarbon group optionally having substituents,
(ii) an aromatic hydrocarbon group optionally having substituents,
(iii) a group represented by the formula: $OR^1$ wherein $R^1$ represents the same meaning as mentioned above and
(iv) a halogen atom, Ar represents an aromatic hydrocarbon group optionally having substituents, a group represented by the formula:

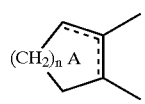

represents a group represented by the formula:

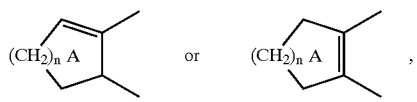

and n is an integer of 1 to 4, or a salt thereof.

2. A compound represented by the formula:

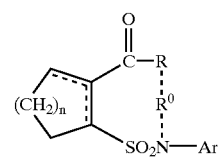
(Ia)

wherein R represents an aliphatic hydrocarbon group optionally having substituents, an aromatic hydrocarbon group optionally having substituents, a heterocyclic group optionally having substituents, a group represented by the formula: $OR^1$ wherein $R^1$ represents a hydrogen atom or an aliphatic hydrocarbon group optionally having substituents or a group represented by the formula:

wherein $R^{1b}$ represents a hydrogen atom or an aliphatic hydrocarbon group optionally having substituents, $R^{1c}$ is, same with or different from $R^{1b}$, a hydrogen atom or an aliphatic hydrocarbon group optionally having substituents, $R^0$ represents a hydrogen atom or an aliphatic hydrocarbon group, Ar represents an aromatic hydrocarbon group optionally having substituents, a group represented by the formula:

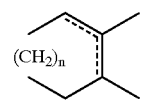

represents a group represented by the formula:

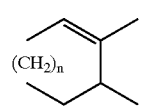 or 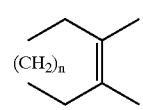, and n is an integer of 1 to 4, provided that when n is 1 or 2 and R is $OR^1$ wherein $R^1$ is a hydrogen atom or an ethyl group, $R^0$ is a methyl group and Ar is a phenyl group a group represented by the formula:

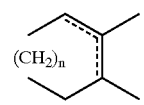

is a group represented by the formula:

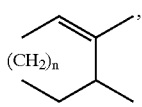

or a salt thereof.

3. A compound as claimed in claim 2, wherein the compound represented by the formula (Ia) is a compound represented by the formula:

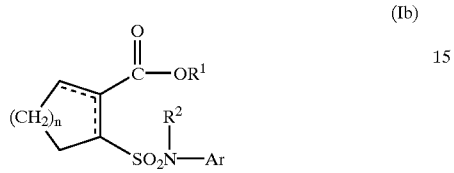

wherein $R^2$ represents a hydrogen atom or an aliphatic hydrocarbon group, $R^1$, Ar, n and the group represented by the formula:

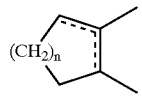

represent the same meanings as defined in claim 2, provided that when n is 1 or 2, Ar is a phenyl group, $R^1$ is a hydrogen atom or an ethyl group and $R^2$ is a methyl group, the group represented by the formula:

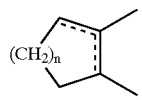

is a group represented by the formula:

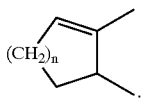

4. A compound as claimed in claim 1, wherein the compound represented by the formula (Iaa) is a compound represented by the formula:

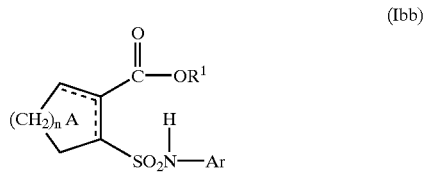

wherein each symbols represents the same meaning as defined in claim 1.

5. A compound as claimed in claim 4, wherein the ring A is a cycloalkene substituted by lower alkyl, phenyl or halogen, $R^1$ is a lower alkyl group, Ar is a phenyl group optionally having substituents, and n is 2.

6. A compound as claimed in claim 3, wherein $R^1$ is a lower alkyl group optionally having substituents.

7. A compound as claimed in claim 3, wherein $R^1$ is an ethyl group.

8. A compound as claimed in claim 3, wherein $R^2$ is a hydrogen atom or a lower alkyl group.

9. A compound as claimed in claim 3, wherein $R^2$ is a hydrogen atom.

10. A compound as claimed in claim 3, wherein Ar is a phenyl group optionally having substituents.

11. A compound as claimed in claim 3, wherein Ar is a phenyl group substituted by halogen or/and lower alkyl.

12. A compound as claimed in claim 3, wherein Ar is a group represented by the formula:

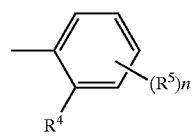

wherein $R^4$ and $R^5$ are same or different and represents a halogen atom or a lower alkyl group, and n is an integer of 0 to 2.

13. A compound as claimed in claim 3, wherein the halogen atom is a fluoro atom or a chloro atom.

14. A compound as claimed in claim 3, wherein the group represented by the formula:

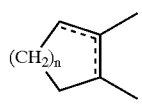

is a group represented by the formula:

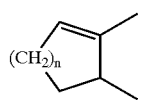

wherein n is the same meaning as defined in claim 2.

15. A compound as claimed in claim 3, wherein n is 1 to 3.

16. A compound as claimed in claim 3, wherein $R^1$ is a lower alkyl-group optionally having substituents, $R^2$ is a hydrogen atom or a-lower alkyl group, Ar is a phenyl group optionally having substituents, n is 1, 2 or 3.

17. A compound as claimed in claim 3, wherein $R^1$ is a lower alkyl group optionally having substituents, $R^2$ is a hydrogen atom, Ar is a phenyl group substituted by a halogen atom, n is 2.

18. A compound as claimed in claim 2, wherein the compound represented by the formula (Ia) is a compound represented by the formula:

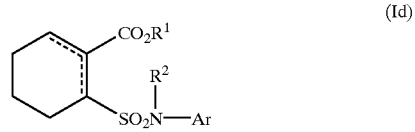

wherein R¹, R² and Ar represent the same meanings as defined in claim 3, a group represented by the formula:

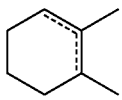

represents a group represented by the formula:

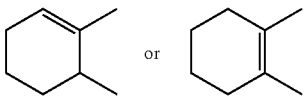

provided that when Ar is a phenyl group, R¹ is a hydrogen atom or an ethyl group and R² is a methyl group, the group represented by the formula:

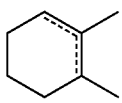

is a group represented by the formula:

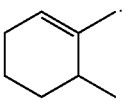

19. D-ethyl 6-[N-(2,4-difluorophenyl)sulfamoyl]-1-cyclohexene-1-carboxylate or a salt thereof.

20. Ethyl 6-[N-(2,4-chlorophenyl)sulfamoyl]-1-cyclohexene-1-carboxylate or a salt thereof.

21. Ethyl 6-[N-(2-chloro-4-methylphenyl)sulfamoyl]-1-cyclohexene-1-carboxylate or a salt thereof.

22. D-ethyl 6-[N-(2-chloro-4-fluorophenyl)sulfamoyl]-1-cyclohexene-1-carboxylate or a salt thereof.

23. A method for producing a compound as claimed in claim 3 which comprises reacting a compound represented by the formula:

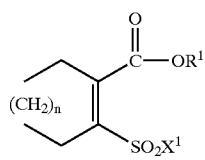

(IIa)

wherein R¹ and n represent the same meanings as defined in claim 3 and X¹ represents a leaving group, or a salt thereof with a compound represented by the formula:

(IIIa)

wherein each symbols represents the same meaning as claimed in claim 3, or a salt thereof.

24. A method for producing a compound as claimed in claim 20 which comprises reacting a compound represented by the formula:

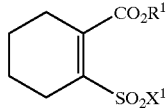

(IIc)

wherein R¹ represents the same meanings as defined in claim 20 and X¹ represents a leaving group, or a salt thereof with a compound represented by the formula:

(IIIa)

wherein each symbols represents the same meaning as claimed in claim 20, or a salt thereof.

25. A pharmaceutical composition comprising a compound represented by the formula:

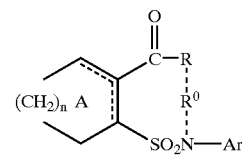

(Iaa)

wherein R represents an aliphatic hydrocarbon group optionally having substituents, an aromatic hydrocarbon group optionally having substituents, a heterocyclic group optionally having substituents, a group represented by the formula: OR¹ wherein R¹ represents a hydrogen atom or an aliphatic hydrocarbon group optionally having substituents or a group represented by the formula:

wherein R¹ᵇ represents a hydrogen atom or an aliphatic hydrocarbon group optionally having substituents, R¹ᶜ is, same with or different from R¹ᵇ, a hydrogen atom or an aliphatic hydrocarbon group optionally having substituents, R⁰ represents a hydrogen atom or an aliphatic hydrocarbon group, ring A is a cycloalkene substituted by 1 to 4 substituents selected from
 (i) an aliphatic hydrocarbon group optionally having substituents,
 (ii) an aromatic hydrocarbon group optionally having substituents,
 (iii) a group represented by the formula: OR¹ wherein R¹ represents the same meaning as mentioned above and
 (iv) a halogen atom, Ar represents an aromatic hydrocarbon group optionally having substituents, a group represented by the formula:

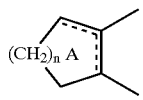

represents a group represented by the formula:

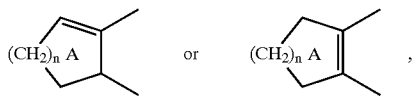

and n is an integer of 1 to 4, or a salt thereof and a pharmacologically acceptable carrier, diluent or excipient.

26. A pharmaceutical composition comprising a compound represented by the formula:

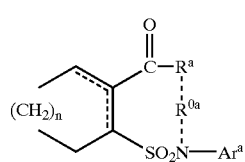

(Ie)

wherein $R^a$ represents an aliphatic hydrocarbon group optionally having substituents, an aromatic hydrocarbon group optionally having substituents, a heterocyclic group optionally having substituents, a group represented by the formula: $OR^{1a}$
wherein $R^{1a}$ represents a hydrogen atom or an aliphatic hydrocarbon group optionally having substituents or a group represented by the formula:

wherein $R^{1a}$ represents the same meaning as defined above,
$R^{1b}$ is, same with or different from $R^{1a}$, a hydrogen atom or an aliphatic hydrocarbon group optionally having substituents,
$R^{0a}$ represents a hydrogen atom or an aliphatic hydrocarbon group,
$Ar^a$ represents an aromatic hydrocarbon group optionally having substituents, a group represented by the formula:

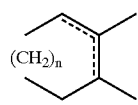

represents a group represented by the formula:

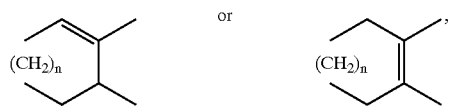

n represents an integer of 1 to 4,
or a salt thereof
and a pharmacologically acceptable carrier, diluent or excipient.

27. A pharmaceutical composition of claim 26 wherein said compound is represented by the formula:

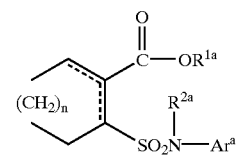

(If)

wherein $R^{2a}$ represents a hydrogen atom or an aliphatic hydrocarbon group, $R^{1a}$, $Ar^a$, n and the group represented by the formula:

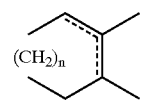

represent the same meanings as defined in claim 26, or a salt thereof.

28. A pharmaceutical composition of claim 27 wherein said compound is represented by the formula:

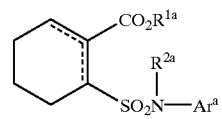

(Ig)

wherein $R^{1a}$, $R^{2a}$ and $Ar^a$ represent the same meaning as defined in claim 27 and the group represented by the formula:

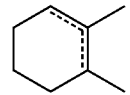

is a group represented by the formula:

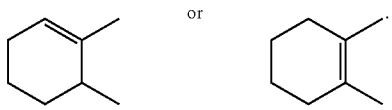

29. The pharmaceutical composition as claimed in any one of claims 25 to 28 which is an agent for inhibiting nitric oxide and/or cytokine production.

30. The pharmaceutical composition as claimed in 29 which is an agent for preventing or treating cardiac disease, autoimmune disease or septick shock.

31. A method for inhibiting nitric oxide, cytokine production or nitric oxide and cytokine production in mammals which comprises administering to a subject in need thereof an effective amount of a compound of claim 1.

32. A method for preventing or treating cardiac disease, autoimmune disease or septic shock in mammals which comprises administering to a subject in need thereof an effective amount of a compound of claim 1.

33. A pro-drug of the compound as claimed in claim 1 or 2.

34. A pharmaceutical composition which contains the pro-drug as claimed in claim 33.

* * * * *